(12) United States Patent
Nakashima et al.

(10) Patent No.: US 8,236,789 B2
(45) Date of Patent: Aug. 7, 2012

(54) 1-ADAMANTYL AZETIDIN-2-ONE DERIVATIVES AND DRUGS CONTAINING SAME

(75) Inventors: Hisashi Nakashima, Tokyo (JP); Takahiro Mori, Tokyo (JP); Ryoko Mori, legal representative, Kasuga (JP); Takaaki Araki, Tokyo (JP); Takahisa Ogamino, Tokyo (JP); Kazutoyo Abe, Tokyo (JP); Tadaaki Ohgiya, Tokyo (JP)

(73) Assignee: Kowa Company, Ltd., Nagoya-shi (JP)

( * ) Notice: Subject to any disclaimer, the term of this patent is extended or adjusted under 35 U.S.C. 154(b) by 412 days.

(21) Appl. No.: 12/550,206

(22) Filed: Aug. 28, 2009

(65) Prior Publication Data

US 2010/0075943 A1 Mar. 25, 2010

Related U.S. Application Data

(60) Provisional application No. 61/093,026, filed on Aug. 29, 2008, provisional application No. 61/155,674, filed on Feb. 26, 2009.

(51) Int. Cl.
| | |
|---|---|
| C07D 205/08 | (2006.01) |
| C07D 227/087 | (2006.01) |
| A61K 31/397 | (2006.01) |
| A61K 31/4427 | (2006.01) |
| A61K 31/443 | (2006.01) |
| A61K 31/4725 | (2006.01) |
| A61P 3/10 | (2006.01) |
| A61P 3/04 | (2006.01) |
| A61P 9/12 | (2006.01) |
| A61P 3/06 | (2006.01) |

(52) U.S. Cl. .................... 514/210.02; 540/200
(58) Field of Classification Search ............ 540/200; 514/210.02
See application file for complete search history.

(56) References Cited

FOREIGN PATENT DOCUMENTS

| GB | 2143819 A | 2/1985 |
|---|---|---|
| JP | 48-15926 B | 5/1973 |
| JP | 2007-536337 A | 12/2007 |
| JP | 2008-519765 A | 6/2008 |
| JP | 2008-526858 A | 7/2008 |
| JP | 2008-526874 A | 7/2008 |
| WO | 95/29909 A1 | 11/1995 |
| WO | 2004/037251 A1 | 5/2004 |
| WO | 2004/112779 A1 | 12/2004 |
| WO | 2005/046685 A1 | 5/2005 |
| WO | 2005/108368 A1 | 11/2005 |
| WO | 2005110992 A1 | 11/2005 |
| WO | 2006/000371 A2 | 1/2006 |
| WO | 2006/010546 A2 | 2/2006 |
| WO | 2006/040329 A1 | 4/2006 |
| WO | 2006/049952 A1 | 5/2006 |
| WO | 2006/051662 A1 | 5/2006 |
| WO | 2006/053024 A2 | 5/2006 |
| WO | 2006/055752 A2 | 5/2006 |
| WO | 2006/132197 A1 | 12/2006 |
| WO | 2006/132436 A1 | 12/2006 |
| WO | 2006/134467 A1 | 12/2006 |
| WO | 2007/003521 A2 | 1/2007 |
| WO | 2007/007688 A1 | 1/2007 |
| WO | 2007/029021 A1 | 3/2007 |
| WO | 2007/068330 A1 | 6/2007 |
| WO | 2007/107550 A1 | 9/2007 |
| WO | 2010/023931 A1 | 3/2010 |

OTHER PUBLICATIONS

Quinkert, Helvetica Chimica Acta (1997), 80(6), 1683-1772.*
Notification of Transmittal of Translation of the International Preliminary Report on Patentability (Form PCT/IB/338) of International Application No. PCT/JP2009/004189 mailed Apr. 21, 2011 with Forms PCT/IB/373 and PCT/ISA/237.
Istvan Lengyel, et al. "About the Reaction of 2, 3-Dibromo-2-Methyl-N-(1-Adamantyl)-Propanamide with a Sodium Tert-Butoxide. A Competition Experiment". Synthetic Communications, 2011, 31(16), pp. 2499-2506.
Shu-Ming Lu, et al. "Carbonylative Ring Expansion of Aziridines to b-Lactams with Rhodium-Complexed Dendrimers on a Resin". JOC Note, Apr. 21, 2004, pp. 3558-3561.
Howard Alper, et al. "Regiospecific Synthesis of a-Methylene-b-Lactams by a Homogeneous Palladium Catalyzed Ring Expansion-Carbonylation Reaction". Tetrahedron Letters, vol. 28, No. 28, pp. 3237-3240.

(Continued)

*Primary Examiner* — Mark Berch
(74) *Attorney, Agent, or Firm* — Westerman, Hattori, Daniels & Adrian, LLP

(57) ABSTRACT

It is to provide a novel compound useful for preventing and/or treating diseases that involves 11β-hydroxysteroid dehydrogenase 1, particularly diabetes, insulin resistance, diabetes complication, obesity, dyslipidemia, hypertension, fatty liver, or metabolic syndrome. It is an 1-adamantyl azetidin-2-one derivative represented by the following general formula (1) or salt thereof, or their solvate.

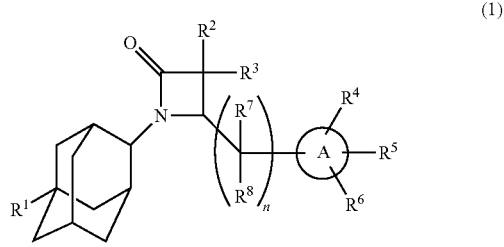

(1)

[wherein A ring represents $C_{6-10}$ aryl group, 5- to 14-membered heteroaryl group, $R^1$ is a hydrogen atom, halogen atom, $C_{1-6}$ alkoxycarbonyl group, hydroxyl group, carboxyl group or carbamoyl group; $R^2$ and $R^3$ are the same or different and are a $C_{1-6}$ alkyl group; $R^4$, $R^5$, and $R^6$ are same or different, and are a hydrogen atom, halogen atom, $C_{1-6}$ alkyl group, $C_{1-6}$ alkoxy group, $C_{6-10}$ aryl group, or $R^4$ and $R^5$, or $R^5$ and $R^6$ may together form a $C_{1-3}$ alkylenedioxy group, $R^7$ and $R^8$ are the same of different and represent a hydrogen atom or $C_{1-6}$ alkyl group, or may together form a $C_{3-6}$ cyclic hydrocarbon group, n represents an integer of 0 or 1].

3 Claims, No Drawings

OTHER PUBLICATIONS

Robert S Lindsay, et al. "Subcutaneous Adipose 11b-Hydroxysteroid Dehydrogenase Type 1 Activity and Messenger Ribonucleic Acid Levels Are Associated with Adiposity and Insulinemia in Pima Indians and Caucasians". Journal of Clinical Endocrinology and Metabolism, 88, pp. 2738-2744.

A. Commercon, et al. "Synthese de Methylene-3 Azetidinones-2 Par Transfert de Phase Solide/Liquide et Preparation de Leurs Analogues Thioxo". in French, Tetrahedron Letters, vol. 24, No. 35, pp. 3725-3728.

"Molecular Pathology of Metabolic Syndrome", Glucocorticoid effect and metabolic syndrome, Topics, vol. 30, No. 9, 2004.(w/partial English translation).

John W. Clader, et al. "2-Azetidinone Cholesterol Absorption Inhibitors: Structure-Activity Relationships on the Heterocyclic Nucleus". Journal of Medicinal Chemistry, 1996, Vol. 39, No. 19, pp. 3684-3693.

Yuri Kotelevsev, et al. "11b-Hydroxysteroid Dehydrogenase Type 1 Knockout Mice Show Attenuated Glucocorticoid-Inducible Responses and Resist Hyperglycemia on Obesity or Stress". PNAS, 1997, vol. 94, pp. 14924-14929.

Istvan Lengyel, et al. "About the Reaction of 2, 3-Dibromo-2-Methyl-N-(1-Adamantyl)-Propanamide with a Sodium Tert-Butoxide. A Competition Experiment". Synthetic Communications, 2001, 31(16), pp. 2499-2506.

Shu-Ming Lu, et al. "Carbonylative Ring Expansion of Aziridines to b-Lactams with Rhodium-Complexed Dendrimers on a Resin". J. Org. Chem., 69, Apr. 21, 2004, pp. 3558-3561.

Serge Calet, et al. "Enantiospecific and Stereospecific Rhodium (I)-Catalyzed Carbonylation and Ring Expansion of Aziridines. Asymmetric Synthesis of b-Lactams and the Kinetic Resolution of Aziridines". J. Am. Chem. Soc., 1989, vol. 111, No. 3, pp. 931-934.

I J Bujalska, et al. "Expression Profiling of 11 b-Hydroxysteroid Dehydrogenase Type-1 and Glucocorticoid-Target Genes in Subcutaneous and Omental Human Preadipocytes". Journal of Molecular Endocrinology, (2006), 37, pp. 327-340.

Nicholas M Morton, et al. "Improved Lipid and Lipoprotein Profile, Hepatic Insulin Sensitivity, and Glucose Tolerance in 11b-Hydroxysteroid Dehydrogenase Type 1 Null Mice". Journal of Biological Chemistry, issue of Nov. 2, 2001, vol. 276, No. 44, pp. 41293-41300.

Tsutomu Tomita, et al. "Metabolic Syndrome". Clinician, 2004, vol. 30, No. 9, pp. 1782-1787 (w/partial English translation).

Dominique Roberto, et al. "Novel Catalytic and Stolchiometric Approaches to Azetidine-2, 4-diones from a-Lactams Using Rhodium and Cobalt Complexes, Respectively". Organometallics, 1984, 3, pp. 1767-1769.

Howard Alper, et al. "Regiospecific Metal-Catalyzed Ring Expansion of Aziridines to b-Lactams". Journal of American Chemical Society, 1983, 105, pp. 6737-6738.

Howard Alper, et al. "Regiospecific Synthesis of a-Methylene-b-Lactams by a Homogeneous Palladium Catalyzed Ring Expansion-Carbonylation Reaction". Tetrahedron Letters, vol. 28, No. 28, pp. 3237-3240, 1987.

Robert S Lindsay, et al. "Subcutaneous Adipose 11b-Hydroxysteroid Dehydrogenase Type 1 Activity and Messenger Ribonucleic Acid Levels Are Associated with Adiposity and Insulinemia in Pima Indians and Caucasians". Journal of Clinical Endocrinology and Metabolism, 88, pp. 2738-2744, Jun. 2003.

A. Commercon, et al. "Synthese de Methylene-3 Azetidinones-2 Par Transfert de Phase Solide/Liquide et Preparation de Leurs Analogues Thioxo". In French, Tetrahedron Letters, vol. 24, No. 35, pp. 3725-3728,1983.

Erach R Talaty, et al. "Thermal Decomposition of a-Lactams: a New Ring Expansion of an a-Lactam to a b-Lactam System". J.C.S. Chem. Comm. 1973.R, pp. 48-49.

Hiroaki Masuzaki, et al. "Transgenic Amplification of Glucocorticoid Action in Adipose Tissue Causes High Blood Pressure in Mice". Journal of Clinical Investigation. Jul. 2003, vol. 112, No. 1, pp. 83-90.

Hiroaki Masuzaki, et al. "A Transgenic Model of Visceral Obesity and the Metabolic Syndrome". Science, Dec. 7, 2001, vol. 294, pp. 2166-2170.

Jeremy W Tomlinson, et al. "11 b-Hydroxysteroid Dehydrogenase Type 1: A Tissue-Specific Regulator of Glucocorticoid Response". Endocrine Reviews, Oct. 2004, 25, pp. 831-866.

* cited by examiner

1-ADAMANTYL AZETIDIN-2-ONE DERIVATIVES AND DRUGS CONTAINING SAME

TECHNICAL FIELD

The present invention relates to a novel 1-adamantyl azetidin-2-one derivative having an 11β-hydroxy steroid dehydrogenase 1-inhibitory activity and a medicine comprising the same.

BACKGROUND ART

11β-hydroxysteroid dehydrogenase (hereinafter, abbreviated as 11β-HSD)1 is an enzyme that converts in cells an inactive form of glucocorticoid (cortisone or 11-dehydrocorticosterone) into an active form of glucocorticoid (cortisol or 11β-corticosterone), and is found to be expressed on the liver, central nerves and the like as well as subcutaneous fat and visceral fat (non-patent documents 1 and 2). Meanwhile, in cells, enzyme 11β-HSD2 is also present that converts an active form of glucocorticoid into an inactivated form. An active form of glucocorticoid is converted in cells from inactive precursor by the action of 11β-HSD1, thereby exercises its effect. Glucocorticoid has been reported to be involved in adipocyte differentiation and to inhibit glycolipid metabolism that is helped by insulin (non-patent document 3). 11β-HSD1 activity and expression level in adipose tissues positively correlate with body-mass index (BMI) or insulin resistance (non-patent document 4). Further, it is reported that a transgenic mouse over-expressing 11β-HSD1 specifically in adipose tissues exhibits a phenotype comprising a combination of major factors of metabolic syndrome, such as visceral fat accumulation, insulin resistance, dyslipidemia, hypertension and fatty liver (non-patent documents 5 and 6). By contrast, it is reported that, in an 11β-HSD1 knockout mouse, an inactive form cannot be converted to an active form and as a result, the induction of the group of gluconeogenic enzymes attributable to the burden of high-fat food does not occur in the liver, which acts suppressively on hyperglycaemia due to obesity (non-patent document 7). It is also reported that decreased blood triglyceride, elevated HDL cholesterol, and improved insulin resistance were observed (non-patent document 8). From these findings, active form of glucocorticoid produced excessively by 11β-HSD1 is considered to cause the onset of a metabolic disease such as diabetes, insulin resistance, diabetes complication, obesity, dyslipidemia (hyperlipidemia), hypertension, and fatty liver, or a metabolic syndrome pathology which comprises a series of these metabolic diseases. Therefore, a selective inhibitor of 11β-HSD1 is believed to be useful for treating or preventing the above pathologies.

Heretofore, many compounds have been reported for the purpose of inhibiting 11β-HSD1 activity. The examples of reported compounds include compounds having a spiro structure (patent documents 1 to 4), adamantane derivative (patent document 5), sulfonamide derivative (patent document 6), pyrazole derivative (patent document 7), isooxazole derivative (patent document 8), triazole derivative (patent document 9), tetrazole derivative (patent document 10), pyridine derivative (patent document 11), pyrimidine derivative (patent document 12), piperidine derivative (patent document 13), pyridazine derivative (patent document 14), pyrrolidine derivative (patent document 15), thiazole derivative (patent document 16), thiophene derivative (patent document 17), lactam derivative (patent document 18) and the like.

On the other hand, a compound having an adamantyl group on the nitrogen atom (1-adamantyl azetidin-2-one derivative) has been reported. Examples include a compound having action of inhibiting cholesterol absorption (non-patent document 9); a compound having an action of enhancing release of neurotransmitter (patent document 19); and a compound having an antiviral action (patent document 20). Further, 1-adamantyl azetidin-2-one derivative has been reported as a subject of reaction and synthesis studies (non-patent document 10, non-patent document 11, non-patent document 12, non-patent document 13, patent document 21, non-patent document 14, non-patent document 15, non-patent document 16, non-patent document 17). Such are the reports on a compound having 1-adamantyl azetidin-2-one derivative skeleton, and most of them are reported as a compound not having substituent on the 4th position of azetidin-2-one ring, which is different from the 1-adamantyl azetidin-2-one derivative of the present invention. As for the compound which is the closest to the Compound of the present invention (compound No. 79 in the non-patent document 9), the substituent of the 3rd position of azetidin-2-one ring is different from the 1-adamantyl azetidin-2-one derivative of the present invention. Further, there is no description nor suggestion that 1-adamantyl azetidin-2-one derivative inhibits 11β-HSD1 activity, and it has not been known at all that azetidin-2-one skeleton compound is useful as an agent for preventing and/or treating diabetes, insulin resistance, diabetes complication, obesity, dyslipidemia, hypertension, fatty liver, or metabolic syndrome.

PRIOR ART DOCUMENT

Non-Patent Document

Non-patent Document 1: J. Mol. Endocrinol., 37:327-340 (2006)
Non-patent Document 2: Endcr. Rev., 25:831-866 (2004)
Non-patent Document 3: Rinsho-i, vol. 30, No. 9, 1782-1787 (2004)
Non-patent Document 4: J. Clin. Endocrinol. Metab., 88:2738-2744 (2003)
Non-patent Document 5: Science 294: 2166-2170 (2001)
Non-patent Document 6: J. Clin. Invest. 112:83-90 (2003)
Non-patent Document 7: Proc. Natl. Acad. Sci. USA 94:14924-14929 (1997)
Non-patent Document 8: J. Biol. Chem., 276 41293-41301 (2001)
Non-patent Document 9: J. Med. Chem., 39:3684-3693 (1996)
Non-patent Document 10: J. Org. Chem., 69:3558-3561 (2004)
Non-patent Document 11: Syn. Commun., 31:2499-2506 (2001)
Non-patent Document 12: J. Am. Chem. Soc., 111:931-934 (1989)
Non-patent Document 13: Tetrahedron Lett., 28:3237-3240 (1987)
Non-patent Document 14: Organometallics, 3:1767-1769 (1984)
Non-patent Document 15: J. Am. Chem. Soc., 105:6737-6738 (1983)
Non-patent Document 16: Tetrahedron Lett., 24:3725-3728 (1983)
Non-patent Document 17: J. Chem. Soc., Chem. Commun., (2):48-49 (1973)

Patent Document

Patent Document 1: WO2005/310992
Patent Document 2: WO2006/040329
Patent Document 3: WO2006/053024
Patent Document 4: WO2006/055752
Patent Document 5: WO2005/108368
Patent Document 6: WO2006/134467
Patent Document 7: WO2006/132436
Patent Document 8: WO2006/132197
Patent Document 9: WO2007/007688
Patent Document 10: WO2007/029021
Patent Document 11: WO2006/010546
Patent Document 12: WO2006/000371
Patent Document 13: WO2005/046685
Patent Document 14: WO2007/003521
Patent Document 15: WO2004/037251
Patent Document 16: WO2006/051662
Patent Document 17: WO2004/112779
Patent Document 18: WO2006/049952
Patent Document 19: WO95/29909
Patent Document 20: Japanese Patent Publication No. 48-15926
Patent Document 21: UK Patent Application No. GB2143819

DISCLOSURE OF THE INVENTION

Object to be Solved by the Invention

The object of the present invention is to provide a novel compound that inhibits 11β-HSD1 selectively, and is useful as a medicine.

Means to Solve the Object

The present inventors made a keen study to find a compound that selectively inhibits 11β-HSD1. Consequently, the present inventors have found that a compound having 1-adamantyl azetidin-2-one skeleton represented by the following formula (1) is a compound that inhibits 11β-HSD1 selectively and thus completed the present invention. More specifically, the present invention relates to

[1] an 1-adamantyl azetidin-2-one derivative represented by the following general formula (1) or salt thereof, or their solvate:

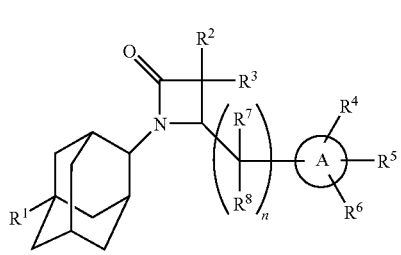

(1)

[wherein A ring represents $C_{6-10}$ aryl group, 5- to 14-membered heteroaryl group, $R^1$ is a hydrogen atom, halogen atom, $C_{1-6}$ alkoxycarbonyl group, mono($C_{1-8}$ alkyl)aminocarbonyl group that may substituted with the following group B, di($C_{1-8}$ alkyl) aminocarbonyl group, $C_{3-6}$ cycloalkyl aminocarbonyl group, $C_{2-6}$ alkanoyl group, formyl group, hydroxyl group, carboxyl group or carbamoyl group; $R^2$ and $R^3$ are the same or different and are a $C_{1-6}$ alkyl group; $R^4$, $R^5$, and $R^6$ are same or different, and are a hydrogen atom, halogen atom, $C_{1-6}$ alkyl group, halo $C_{1-6}$ alkyl group, $C_{1-6}$ alkoxy group, halo $C_{1-6}$ alkoxy group, $C_{1-6}$ alkylthio group, $C_{1-6}$ alkylsulfinyl group, $C_{1-6}$ alkylsulfonyl group, amino group, $C_{6-10}$ aryl group, mono($C_{1-8}$ alkyl)amino group, di($C_{1-8}$ alkyl)amino group, $C_{2-6}$ alkanoylamino group or formylamino group, or $R^4$ and $R^5$, or $R^5$ and $R^6$ may together form a $C_{1-3}$ alkylenedioxy group, $R^7$ and $R^8$ are the same or different and represent a hydrogen atom or $C_{1-6}$ alkyl group, or may together form a $C_{3-6}$ cyclic hydrocarbon group, and n represents an integer of 0 or 1;

Group B: $C_{6-10}$ aryl group, carboxyl group or $C_{1-6}$ alkoxycarbonyl group);

[2] the 1-adamantyl azetidin-2-one derivative or salt thereof, or their solvate according to [1], wherein the compound represented by the formula (I) is a compound selected from the group consisting of:

1-(adamantan-2-yl)-3,3-dimethyl-4-phenylazetidin-2-one,
1-(adamantan-2-yl)-3,3-dimethyl-4-(2,3-dichlorophenyl)azetidin-2-one,
trans-1-(5-chloroadamantan-2-yl)-3,3-dimethyl-4-(2,3-dichlorophenyl)azetidin-2-one,
cis-1-(5-chloroadamantan-2-yl)-3,3-dimethyl-4-(2,3-dichlorophenyl)azetidin-2-one,
trans-1-(5-chloroadamantan-2-yl)-3,3-dimethyl-4-(naphthalen-1-yl)azetidin-2-one,
cis-1-(5-chloroadamantan-2-yl)-3,3-dimethyl-4-(naphthalen-1-yl)azetidin-2-one,
methyl trans-4-[2-(2,3-dichlorophenyl)-3,3-dimethyl-4-oxoazetidin-1-yl]-1-adamantane carboxylate,
trans-4-[2-(2,3-dichlorophenyl)-3,3-dimethyl-4-oxoazetidin-1-yl]-1-adamantane carboxylic acid,
trans-4-[2-(2,3-dichlorophenyl)-3,3-dimethyl-4-oxoazetidin-1-yl]-1-adamantane carboxyamide,
methyl trans-4-[2-(naphthalen-1-yl)-3,3-dimethyl-4-oxoazetidin-1-yl]-1-adamantane carboxylate,
trans-4-[2-(naphthalen-1-yl)-3,3-dimethyl-4-oxoazetidin-1-yl]-1-adamantane carboxylic acid,
trans-4-[2-(naphthalen-1-yl)-3,3-dimethyl-4-oxoazetidin-1-yl]-1-adamantane carboxyamide,
methyl trans-4-[2-(benzo[d][1,3]dioxol-4-yl)-3,3-dimethyl-4-oxoazetidin-1-yl]-1-adamantane carboxylate,
trans-4-[2-(benzo[d][1,3]dioxol-4-yl)-3,3-dimethyl-4-oxoazetidin-1-yl]-1-adamantane carboxylic acid,
trans-4-[2-(benzo[d][1,3]dioxol-4-yl)-3,3-dimethyl-4-oxoazetidin-1-yl]-1-adamantane carboxyamide,
trans-4-[2-(isoquinolin-5-yl)-3,3-dimethyl-4-oxoazetidin-1-yl]-1-adamantane carboxyamide,
trans-4-[2-(quinolin-5-yl)-3,3-dimethyl-4-oxoazetidin-1-yl]-1-adamantane carboxylic acid,
methyl trans-4-[2-(quinolin-8-yl)-3,3-dimethyl-4-oxoazetidin-1-yl]-1-adamantane carboxylate,
trans-4-[2-(quinolin-8-yl)-3,3-dimethyl-4-oxoazetidin-1-yl]-1-adamantane carboxylic acid,
trans-4-[2-(quinolin-8-yl)-3,3-dimethyl-4-oxoazetidin-1-yl]-1-adamantane carboxyamide,
1-(adamantan-2-yl)-3,3-dimethyl-4-(2,3-dimethoxyphenyl)azetidin-2-one,
1-(adamantan-2-yl)-3,3-dimethyl-4-(4-chlorophenyl)azetidin-2-one,
1-(adamantan-2-yl)-3,3-dimethyl-4-(4-methoxyphenyl)azetidin-2-one,
1-(adamantan-2-yl)-3,3-dimethyl-4-(2,3-difluorophenyl)azetidin-2-one,
1-(adamantan-2-yl)-3,3-dimethyl-4-(3-chloro-2-fluorophenyl)azetidin-2-one,
1-(adamantan-2-yl)-3,3-dimethyl-4-(3,4-dichlorophenyl)azetidin-2-one, 1-(adamantan-2-yl)-3,3-dimethyl-4-(3,4-difluorophenyl)
 azetidin-2-one,
1-(adamantan-2-yl)-3,3-dimethyl-4-(2-fluoro-3-trifluorom-
 ethylphenyl)azetidin-2-one,
1-(adamantan-2-yl)-3,3-dimethyl-4-(3-chloro-4-fluorophe-
 nyl)azetidin-2-one,
1-(adamantan-2-yl)-3,3-dimethyl-4-(2-chloro-3-trifluorom-
 ethylphenyl)azetidin-2-one,
1-(adamantan-2-yl)-3,3-dimethyl-4-(3,5-dichlorophenyl)
 azetidin-2-one,
1-(adamantan-2-yl)-3,3-dimethyl-4-(4-fluoro-3-trifluorom-
 ethylphenyl)azetidin-2-one,
1-(adamantan-2-yl)-3,3-dimethyl-4-(2-methoxyphenyl)aze-
 tidin-2-one,
1-(adamantan-2-yl)-3,3-dimethyl-4-(3-methoxyphenyl)aze-
 tidin-2-one,
1-(adamantan-2-yl)-3,3-dimethyl-4-(2,3,5-trifluorophenyl)
 azetidin-2-one,
1-(adamantan-2-yl)-3,3-dimethyl-4-(3,4,5-trifluorophenyl)
 azetidin-2-one,
1-(adamantan-2-yl)-3,3-dimethyl-4-(4-isopropylphenyl)
 azetidin-2-one,
1-(adamantan-2-yl)-3,3-dimethyl-4-(4-t-butylphenyl)azeti-
 din-2-one,
1-(adamantan-2-yl)-3,3-dimethyl-4-(2-fluorophenyl)azeti-
 din-2-one,
1-(adamantan-2-yl)-3,3-dimethyl-4-(2-fluoro-4-methox-
 yphenyl)azetidin-2-one,
1-(adamantan-2-yl)-3,3-dimethyl-4-(2-trifluoromethylphe-
 nyl)azetidin-2-one,
1-(adamantan-2-yl)-3,3-dimethyl-4-(4-trifluoromethox-
 yphenyl)azetidin-2-one,
1-(adamantan-2-yl)-3,3-dimethyl-4-(4-bromophenyl)azeti-
 din-2-one,
1-(adamantan-2-yl)-3,3-dimethyl-4-(2-chlorophenyl)azeti-
 din-2-one,
1-(adamantan-2-yl)-3,3-dimethyl-4-(naphthalen-1-yl)azeti-
 din-2-one,
trans-1-(5-hydroxyadamantan-2-yl)-3,3-dimethyl-4-(2,3-
 dichlorophenyl)azetidin-2-one,
trans-1-(5-hydroxyadamantan-2-yl)-3,3-dimethyl-4-(naph-
 thalen-1-yl)azetidin-2-one,
trans-1-(5-hydroxyadamantan-2-yl)-3,3-dimethyl-4-(4-
 methoxynaphthalen-1-yl)azetidin-2-one,
methyl trans-4-[2-(quinolin-4-yl)-3,3-dimethyl-4-oxoazeti-
 din-1-yl]-1-adamantane carboxylate,
trans-4-[2-(quinolin-4-yl)-3,3-dimethyl-4-oxoazetidin-1-
 yl]-1-adamantane carboxylic acid,
trans-4-[2-(quinolin-4-yl)-3,3-dimethyl-4-oxoazetidin-1-
 yl]-1-adamantane carboxyamide,
trans-1-(5-fluoroadamantan-2-yl)-3,3-dimethyl-4-(2,3-
 dichlorophenyl)azetidin-2-one,
1-(adamantan-2-yl)-3,3-dimethyl-4-(3-chlorophenyl)azeti-
 din-2-one,
1-(adamantan-2-yl)-3,3-dimethyl-4-[3,5-bis(trifluorom-
 ethyl)phenyl]azetidin-2-one,
1-(adamantan-2-yl)-3,3-dimethyl-4-[4-(methylthio)phenyl]
 azetidin-2-one,
1-(adamantan-2-yl)-3,3-dimethyl-4-(4-methoxy-2-meth-
 ylphenyl)azetidin-2-one,
trans-4-[2-(benzo[d][1,3]dioxol-4-yl)-3,3-dimethyl-4-
 oxoazetidin-1-yl]-N-methyl-1-adamantane carboxya-
 mide,
trans-4-[2-(benzo[d][1,3]dioxol-4-yl)-3,3-dimethyl-4-
 oxoazetidin-1-yl]-N-ethyl-1-adamantane carboxyamide,
trans-4-[2-(benzo[d][1,3]dioxol-4-yl)-3,3-dimethyl-4-
 oxoazetidin-1-yl]-N-propyl-1-adamantane carboxyamide,
trans-4-[2-(benzo[d][1,3]dioxol-4-yl)-3,3-dimethyl-4-
 oxoazetidin-1-yl]-N-hexyl-1-adamantane carboxyamide,
trans-4-[2-(benzo[d][1,3]dioxol-4-yl)-3,3-dimethyl-4-
 oxoazetidin-1-yl]-N-octyl-1-adamantane carboxyamide,
trans-4-[2-(benzo[d][1,3]dioxol-4-yl)-3,3-dimethyl-4-
 oxoazetidin-1-yl]-N-cyclopropyl-1-adamantane car-
 boxyamide,
trans-4-[2-(benzo[d][1,3]dioxol-4-yl)-3,3-dimethyl-4-
 oxoazetidin-1-yl]-N-cyclohexyl-1-adamantane carboxya-
 mide,
trans-4-[2-(benzo[d][1,3]dioxol-4-yl)-3,3-dimethyl-4-
 oxoazetidin-1-yl]-N-benzyl-1-adamantane carboxyamide,
methyl trans-2-[4-(2-(benzo[d][1,3]dioxol-4-yl)-3,3-dim-
 ethyl-4-oxoazetidin-1-yl)-1-adamantane carboxyamide]
 acetate,
trans-2-[4-(2-(benzo[d][1,3]dioxol-4-yl)-3,3-dimethyl-4-
 oxoazetidin-1-yl)-1-adamantane carboxyamide]acetic
 acid,
1-(adamantan-2-yl)-4-(2,5-dihydrobenzo[b]oxepin-9-yl)-3,
 3-dimethylazetidin-2-one,
1-(adamantan-2-yl)-3,3-dimethyl-4-(benzo[b]oxepan-9-yl)
 azetidin-2-one,
4-benzyl-1-(adamantan-2-yl)-3,3-dimethylazetidin-2-one,
4-[1-(4-chlorophenyl)cyclopropyl]-1-(adamantan-2-yl)-3,3-
 dimethylazetidin-2-one,
1-(adamantan-2-yl)-3,3-dimethyl-4-(1-phenylcyclopropyl)
 azetidin-2-one,
1-(adamantan-2-yl)-4-[1-(4-methoxyphenyl)cyclopropyl]-3,
 3-dimethylazetidin-2-one,
1-(adamantan-2-yl)-3,3-dimethyl-4-(1-p-tolylcyclopropyl)
 azetidin-2-one,
4-[1-(benzo[d][1,3]dioxol-5-yl)cyclopropyl]-1-(adamantan-
 2-yl)-3,3-dimethylazetidin-2-one,
4-[1-(4-bromophenyl)cyclopropyl]-1-(adamantan-2-yl)-3,3-
 dimethylazetidin-2-one,
1-(adamantan-2-yl)-3,3-dimethyl-4-[1-(pyridin-2-yl)cyclo-
 propyl]azetidin-2-one,
4-[1-(2-chlorophenyl)cyclopropyl]-1-(adamantan-2-yl)-3,3-
 dimethylazetidin-2-one,
4-[1-(3-chlorophenyl)cyclopropyl]-1-(adamantan-2-yl)-3,3-
 dimethylazetidin-2-one,
4-[1-(biphenyl-4-yl)cyclopropyl]-1-(adamantan-2-yl)-3,3-
 dimethylazetidin-2-one,
methyl trans-4-{2-[1-(pyridin-2-yl)cyclopropyl]-3,3-dim-
 ethyl-4-oxoazetidin-1-yl}-1-adamantane carboxylate,
trans-4-{2-[1-(pyridin-2-yl)cyclopropyl]-3,3-dimethyl-4-
 oxoazetidin-1-yl}-1-adamantane carboxylic acid, and
trans-4-{2-[1-(pyridin-2-yl)cyclopropyl]-3,3-dimethyl-4-
 oxoazetidin-1-yl}-1-adamantane carboxyamide;

[3] a pharmaceutical composition consisting of the 1-ada-
mantyl azetidin-2-one derivative or salt thereof, or their sol-
vate according to [1] or [2], and a pharmaceutically accept-
able carrier;

[4] an inhibitor of 11β-hydroxysteroid dehydrogenase 1,
comprising the 1-adamantyl azetidin-2-one derivative or salt
thereof, or their solvate according to [1] or [2] as an active
ingredient;

[5] an agent for preventing and/or treating diabetes, insulin
resistance, diabetes complication, obesity, dyslipidemia,
hypertension, fatty liver, or metabolic syndrome, which agent
comprises the 1-adamantyl azetidin-2-one derivative or salt
thereof, or their solvate according to [1] or [2] as an active
ingredient;

[6] use of the 1-adamantyl azetidin-2-one derivative or salt
thereof, or their solvate according to [1] or [2] for producing
a formulation for inhibiting 11β-hydroxysteroid dehydroge-
nase 1;

[7] use of the 1-adamantyl azetidin-2-one derivative or salt thereof, or their solvate according to [1] or [2] for producing a formulation for preventing and/or treating diabetes, insulin resistance, diabetes complication, obesity, dyslipidemia, hypertension, fatty liver, or metabolic syndrome;

[8] a method for inhibiting 11β-hydroxysteroid dehydrogenase 1, which method comprises administering an effective amount of the 1-adamantyl azetidin-2-one derivative or salt thereof, or their solvate according to [1] or [2];

[9] a method for preventing and/or treating diabetes, insulin resistance, diabetes complication, obesity, dyslipidemia, hypertension, fatty liver, or metabolic syndrome, which method comprises administering an effective amount of the 1-adamantyl azetidin-2-one derivative or salt thereof, or their solvate according to [1] or [2].

Effect of the Invention

A 1-adamantyl azetidin-2-one derivative or salt thereof, or their solvate of the present invention shows a superior inhibitory effect of 11β-hydroxysteroid dehydrogenase 1, and is useful as an agent for preventing or treating a disease that involves 11β-hydroxysteroid dehydrogenase 1 (in particular, diabetes, insulin resistance, diabetes complication, obesity, dyslipidemia, hypertension, fatty liver, or metabolic syndrome).

BEST MODE OF CARRYING OUT THE INVENTION

The present invention will be explained in detail herein below.
(1-adamantyl azetidin-2-one derivative represented by the general formula (1))

Herein, a "halogen atom" represents a halogeno group, and examples include a fluorine atom, chlorine atom, bromine atom and iodine atom.

Herein, "alkyl" may be straight-chained or branched-chained. Therefore, examples of "$C_{1-8}$ alkyl group" include a methyl group, ethyl group, propyl group, isopropyl group, butyl group, isobutyl group, sec-butyl group, tert-butyl group, pentyl group, isopentyl group, neopentyl group, hexyl group, isohexyl group, heptyl group and octyl group.

Herein, examples of "$C_{1-6}$ alkyl group" include a methyl group, ethyl group, propyl group, isopropyl group, butyl group, isobutyl group, sec-butyl group, tert-butyl group, pentyl group, isopenthyl group, neopentyl group, hexyl group and isohexyl group.

Herein, "haloalkyl" is an alkyl group substituted with one to the maximum number of substitutable halogen atoms, which is the same or different. Therefore, examples of "halo $C_{1-6}$ alkyl group" specifically include monofluoromethyl group, difluoromethyl group, trifluoromethyl group, monochloromethyl group, monobromomethyl group, monoiodomethyl group, and 2,2,2-trifluoroethyl group.

Herein, "alkoxy" may be straight-chained or branched-chained. Therefore, examples of "$C_{1-6}$ alkoxy group" include a methoxy group, ethoxy group, propoxy group, isopropoxy group, butoxy group, isobutoxy group, sec-butoxy group, tert-butoxy group, pentoxy group, isopentoxy group, neopentoxy group, hexyloxy group, and isohexyloxy group.

Herein, "haloalkoxy" means an alkoxy group substituted with one to the maximum number of substitutable halogen atoms, which is the same or different. Therefore, examples of "halo $C_{1-6}$ alkoxy group" specifically include a monofluoromethoxy group, difluoromethoxy group, trifluoromethoxy group, monochloromethoxy group, monobromomethoxy group, monoiodomethoxy group, and 2,2,2-trifluoroethoxy group.

Herein, "aryl" means a monocyclic or condensed ring aromatic hydrocarbon ring. Therefore, examples of "$C_{6-10}$ aryl group" include a phenyl group, naphthyl group and azulenyl group.

Herein, "5- to 14-membered heteroaryl group" means a 5- to 14-membered monocyclic aromatic heterocyclic group or condensed aromatic heterocyclic group containing 1 to 4 heteroatoms selected from a nitrogen atom, oxygen atom and sulfur atom in addition to a carbon atom as atoms constituting the ring. Examples of monocyclic aromatic heterocyclic group include a 2-furyl group, 3-furyl group, 2-thienyl group, 3-thienyl group, pyrrol-1-yl group, pyrrol-2-yl group, pyrrol-3-yl group, pyridin-2-yl group, pyridin-3-yl group, pyridin-4-yl group, pyrazin-2-yl group, pyrimidin-2-yl group, pyrimidin-4-yl group, pyrimidin-5-yl group, pyridazin-3-yl group, pyridazin-4-yl group, imidazol-1-yl group, imidazol-2-yl group, imidazol-4-yl group, pyrazol-1-yl group, pyrazol-3-yl group, pyrazol-4-yl group, thiazol-2-yl group, thiazol-4-yl group, thiazol-5-yl group, oxazol-2-yl-group, oxazol-4-yl group, oxazol-5-yl group, isooxazol-3-yl group, isooxazol-4-yl group, isooxazol-5-yl group, 1,3,4-thiadiazol-2-yl group, 1,2,3-triazol-1-yl group, 1,2,3-triazol-4-yl group, 1,2,4-triazol-1-yl group, group, 1,2,4-triazol-4-yl group, tetrazol-1-yl group, and tetrazol-5-yl group. Examples of condensed aromatic heterocyclic group include a benzofuran-2-yl group, benzofuran-3-yl group, benzofuran-4-yl group, benzofuran-5-yl group, benzofuran-6-yl group, benzofuran-7-yl group, benzothiophen-2-yl group, benzothiophen-3-yl group, benzothiophen-4-yl group, benzothiophen-5-yl group, benzothiophen-6-yl group, benzothiophen-7-yl group, quinoxalin-2-yl group, quinoxalin-5-yl group, quinoxalin-6-yl group, indol-1-yl group, indol-2-yl group, indol-3-yl group, indol-4-yl group, indol-5-yl group, indol-6-yl group, indol-7-yl group, isoindol-1-yl group, isoindol-2-yl group, isoindol-4-yl group, isoindol-5-yl group, isobenzofuran-1-yl group, isobenzofuran-4-yl group, isobenzofuran-5-yl group, chromen-2-yl group, chromen-3-yl group, chromen-4-yl group, chromen-5-yl group, chromen-6-yl group, chromen-7-yl group, chromen-8-yl group, benzoimidazol-1-yl group, benzoimidazol-2-yl group, benzoimidazol-4-yl group, benzoimidazol-5-yl group, benzothiazol-2-yl group, benzothiazol-4-yl group, benzothiazol-5-yl group, benzooxazol-2-yl group, benzooxazol-4-yl group, benzooxazol-5-yl group, quinolin-2-yl group, quinolin-3-yl group, quinolin-4-yl group, quinolin-5-yl group, quinolin-6-yl group, quinolin-7-yl group, quinolin-8-yl group, isoquinolin-1-yl group, isoquinolin-3-yl group, isoquinolin-4-yl group, isoquinolin-5-yl group, isoquinolin-6-yl group, isoquinolin-7-yl group, isoquinolin-8-yl group, 2,5-dihydrobenzo[b]oxepin-9-yl group, and benzo[b]oxepan-9-yl group.

Herein, "alkoxycarbonyl group" means a group wherein a straight-chained or branched-chained alkoxy group is bound to a carbonyl group (CO). Therefore, "$C_{1-6}$ alkoxycarbonyl group" is a group wherein an $C_{1-6}$ alkoxy group and carbonyl group are bound, and examples include a methoxycarbonyl group, ethoxycarbonyl group, propoxycarbonyl group, isopropoxycarbonyl group, butoxycarbonyl group, isobutoxycarbonyl group, sec-butoxycarbonyl group, tert-butoxycarbonyl group, pentoxycarbonyl group, isopentoxycarbonyl group, neopentoxycarbonyl group, hexyloxycarbonyl group and isohexyloxycarbonyl group.

Herein, "alkylthio" means a group wherein a straight-chained or branched-chained alkyl group is bound to a sulfur atom. Therefore, examples of "$C_{1-6}$ alkylthio group" include a methylthio group, ethylthio group, propylthio group, isopropylthio group, butylthio group, isobutylthio group, sec-butylthio group, tert-butylthio group, pentylthio group, isopentylthio group, neopentylthio group, hexylthio group and isohexylthio group.

Herein, "alkylsulfinyl" means a group wherein a straight-chained or branched-chained alkyl group is bound to a sulfinyl group (SO). Therefore, examples of "$C_{1-6}$ alkylsulfinyl group" include a methylsulfinyl group, ethylsulfinyl group, propylsulfinyl group, isopropylsulfinyl group, butylsulfinyl group, isobutylsulfinyl group, sec-butylsulfinyl group, tert-butylsulfinyl group, pentylsulfinyl group, isopentylsulfinyl group, neopentylsulfinyl group, hexylsulfinyl group and isohexylsulfinyl group.

Herein, "alkylsulfonyl" means a group wherein a straight-chained or branched-chained alkyl group is bound to a sulfonyl group ($SO_2$). Therefore, examples of "$C_{1-6}$ alkylsulfonyl group" include a methylsulfonyl group, ethylsulfonyl group, propylsulfonyl group, isopropylsulfonyl group, butylsulfonyl group, isobutylsulfonyl group, sec-butylsulfonyl group, tert-butyl sulfonyl group, pentylsulfonyl group, isopentylsulfonyl group, neopentylsulfonyl group, hexylsulfonyl group and isohexylsulfonyl group.

Herein, "alkanoyl" means a group wherein an oxo group is bound to the 1st position of an alkyl group. Therefore, examples of "$C_{2-6}$ alkanoyl group" include an acetyl group, propionyl group, butyryl group, isobutyryl group, valeryl group, isovaleryl group, pivaloyl group and hexanoyl group.

Herein, "monoalkylamino" means a group wherein one alkyl group is bound to a nitrogen atom of an amino group. Therefore, examples of "mono($C_{1-8}$ alkyl)amino group" include a methylamino group, ethylamino group, propylamino group, isopropylamino group, butylamino group, sec-butylamino group, tert-butylamino group, pentylamino group, isopentylamino group, neopentylamino group, 1-methylbutylamino group, 1-ethylpropylamino group, hexylamino group, isohexylamino group, 3-methylpentylamino group, 2-methylpentylamino group, 1-methylpentylamino group, 3,3-dimethylbutylamino group, 2,2-dimethylbutylamino group, 1,1-dimethylbutylamino group, 1,2-dimethylbutylamino group, 1,3-dimethylbutylamino group, 2,3-dimethylbutylamino group, 1-ethylbutylamino group, 2-ethylbutylamino group, heptylamino group and octylamino group.

Herein, "dialkylamino" means a group wherein 2 same or different alkyl groups are bound to a nitrogen atom. Therefore, examples of "di($C_{1-8}$ alkyl)amino group" include a dimethylamino group, methylethylamino group, diethylamino group, methylpropylamino group, ethylpropylamino group, dipropylamino group, methylisopropylamino group, ethylisopropylamino group, diisopropylamino group, methylbutylamino group, ethylbutylamino group, propylbutylamino group, dibutylamino group, di-sec-butylamino group, di-tert-butylamino group, dipentylamino group, dihexylamino group, diheptylamino group and dioctylamino group.

Herein, "monoalkylaminocarbonyl group" means a group wherein a monoalkylamino group is bound to a carbonyl group (CO). Therefore, examples of "mono($C_{1-8}$ alkyl)aminocarbonyl group" include a methylaminocarbonyl group, ethylaminocarbonyl group, propylaminocarbonyl group, isopropylaminocarbonyl group, butylaminocarbonyl group, sec-butylaminocarbonyl group, tert-butylaminocarbonyl group, pentylaminocarbonyl group, isopentylaminocarbonyl group, neopentylaminocarbonyl group, 1-methylbutylaminocarbonyl group, 1-ethylpropylaminocarbonyl group, hexylaminocarbonyl group, isohexylaminocarbonyl group, 3-methylpentylaminocarbonyl group, 2-methylpentylaminocarbonyl group, 1-methylpentylaminocarbonyl group, 3,3-dimethylbutylaminocarbonyl group, 2,2-dimethylbutylaminocarbonyl group, 1,1-dimethylbutylaminocarbonyl group, 1,2-dimethylbutylaminocarbonyl group, 1,3-dimethylbutylaminocarbonyl group, 2,3-dimethylbutylaminocarbonyl group, 1-ethylbutylaminocarbonyl group, 2-ethylbutylaminocarbonyl group, heptylaminocarbonyl group and octylaminocarbonyl group.

Herein, "dialkylaminocarbonyl group" means a group wherein a dialkylamino group is bound to a carbonyl group (CO). Therefore, examples of di($C_{1-6}$ alkyl)aminocarbonyl group include a dimethylaminocarbonyl group, methylethylaminocarbonyl group, diethylaminocarbonyl group, methylpropylaminocarbonyl group, ethylpropylaminocarbonyl group, dipropylaminocarbonyl group, methylisopropylaminocarbonyl group, ethylisopropylaminocarbonyl group, diisopropylaminocarbonyl group, methylbutylaminocarbonyl group, ethylbutylaminocarbonyl group, propylbutylaminocarbonyl group, dibutylaminocarbonyl group, di-sec-butylaminocarbonyl group, di-tert-butylaminocarbonyl group, dipentylaminocarbonyl group, dihexylaminocarbonyl group, diheptylaminocarbonyl group and dioctylaminocarbonyl group.

Herein, "cycloalkyl" means a saturated alkyl group having a cyclic moiety. Therefore, "$C_{3-6}$ cycloalkylaminocarbonyl group" is a group wherein $C_{3-6}$ cycloalkylamino group and a carbonyl group are hound, and examples include a cyclopropylaminocarbonyl group, cyclobutylaminocarbonyl group, cyclopentylaminocarbonyl group, cyclohexylaminocarbonyl group, cyclopropylmethylaminocarbonyl group, cyclopropylethylaminocarbonyl group, cyclobutylmethylaminocarbonyl group and cyclopentylmethylaminocarbonyl group.

Herein, examples of "$C_{2-6}$ alkanoylamino group" include an acetylamino group, propionylamino group, butyrylamino group, isobutyrylamino group, valerylamino group, isovalerylamino group, pivaloylamino group and hexanoylamino group.

Herein, examples of "$C_{1-3}$ alkylenedioxy group" include a methylenedioxy group, ethylenedioxy group, 1,3-propylenedioxy group and 2,2-propylenedioxy group.

Herein, examples of "$C_{3-6}$ cyclic hydrocarbon group" include a 1,1-cyclopropylene group, 1,1-cycloputylene group, 1,1-cyclopentylene group and 1,1-cyclohexylene group.

In general formula (1), $C_{6-10}$ aryl group of A ring is preferably a phenyl group or naphthyl group (1-naphthyl group, etc.).

In general formula (1), 5- to 14-membered heteroaryl group of A ring is preferably a quinolinyl group (quinolin-4-yl group, quinolin-5-yl group, quinolin-8-yl group, etc.), isoquinolinyl group (isoquinolin-5-yl group, etc.), pyridinyl group (pyridin-2-yl group, etc.), 2,5-dihydrobenzo[b]oxepin-9-yl group, or benzo[b]oxepan-9-yl group.

In general formula (1), halogen atom in $R^1$ is preferably a chlorine atom.

In general formula (1), $C_{1-6}$ alkoxycarbonyl group in $R^1$ is preferably a methoxycarbonyl group.

In general formula (1), mono($C_{1-8}$ alkyl)aminocarbonyl group in $R^1$ is preferably a methylaminocarbonyl group, ethylaminocarbonyl group, n-propylaminocarbonyl group, n-hexylaminocarbonyl group, or n-octylaminocarbonyl group. Preferred substituents of mono($C_{1-8}$ alkyl)aminocarbonyl group include $C_{6-10}$ aryl group such as phenyl group, and $C_{1-6}$ alkoxycarbonyl group such as methoxycarbonyl group, other than carboxyl group.

In general formula (1), $C_{3-8}$ cycloalkylaminocarbonyl group is preferably a $C_{3-6}$ cycloalkylaminocarbonyl group, and more preferably a cyclopropylaminocarbonyl group and cyclohexylaminocarbonyl group.

In general formula (1), $C_{1-6}$ alkyl group in $R^2$ and $R^3$ is preferably a $C_{1-4}$ alkyl group, and more preferably a methyl group.

In general formula (1), halogen atom in $R^4$, $R^5$, and $R^6$ is preferably a fluorine atom, chlorine atom or bromine atom.

In general formula (1), $C_{1-6}$ alkyl group in $R^4$, $R^5$, and $R^6$ is preferably a $C_{1-4}$ alkyl group, and more preferably a methyl group, isopropyl group or tert-butyl group.

In general formula (1), halo $C_{1-6}$ alkyl group in $R^4$, $R^5$ and $R^6$ is preferably a trifluoromethyl group.

In general formula (1), $C_{1-6}$ alkoxy group in $R^4$, $R^5$ and $R^6$ is preferably a $C_{1-4}$ alkoxy group, and more preferably a methoxy group.

In general formula (1), halo $C_{1-5}$ alkoxy group in $R^4$, $R^5$ and $R^6$ is preferably a trifluoromethoxy group.

In general formula (1), $C_{1-6}$ alkylthio group in $R^4$, $R^5$ and $R^6$ is preferably a $C_{1-4}$ alkylthio group, and more preferably a methylthio group.

In general formula (1), when $R^4$ and $R^5$, or $R^5$ and $R^6$ together form a $C_{1-3}$ alkylenedioxy group, $C_{1-3}$ alkylenedioxy group is preferably a methylenedioxy group.

In general formula (1), when $R^7$ and $R^8$ together form a $C_{3-6}$ cyclic hydrocarbon group, $C_{3-6}$ cyclic hydrocarbon group is preferably a 1,1-cyclopropylene group.

As for the 1-adamantyl azetidin-2-one derivative represented by general formula (I) of the present invention, the following compound, pharmaceutically acceptable salt thereof, or their solvate are particularly preferred.

1-(adamantan-2-yl)-3,3-dimethyl-4-phenylazetidin-2-one,
1-(adamantan-2-yl)-3,3-dimethyl-4-(2,3-dichlorophenyl)azetidin-2-one,
trans-1-(5-chloroadamantan-2-yl)-3,3-dimethyl-4-(2,3-dichlorophenyl)azetidin-2-one,
cis-1-(5-chloroadamantan-2-yl)-3,3-dimethyl-4-(2,3-dichlorophenyl)azetidin-2-one,
trans-1-(5-chloroadamantan-2-yl)-3,3-dimethyl-4-(naphthalen-1-yl)azetidin-2-one,
cis-1-(5-chloroadamantan-2-yl)-3,3-dimethyl-4-(naphthalen-1-yl)azetidin-2-one,
methyl trans-4-[2-(2,3-dichlorophenyl)-3,3-dimethyl-4-oxoazetidin-1-yl]-1-adamantane carboxylate,
trans-4-[2-(2,3-dichlorophenyl)-3,3-dimethyl-4-oxoazetidin-1-yl]-1-adamantane carboxylic acid,
trans-4-[2-(2,3-dichlorophenyl)-3,3-dimethyl-4-oxoazetidin-1-yl]-1-adamantane carboxamide,
methyl trans-4-[2-(naphthalen-1-yl)-3,3-dimethyl-4-oxoazetidin-1-yl]-1-adamantane carboxylate,
trans-4-[2-(naphthalen-1-yl)-3,3-dimethyl-4-oxoazetidin-1-yl]-1-adamantane carboxylic acid,
trans-4-[2-(naphthalen-1-yl)-3,3-dimethyl-4-oxoazetidin-1-yl]-1-adamantane carboxamide,
methyl trans-4-[2-(benzo[d][1,3]dioxol-4-yl)-3,3-dimethyl-4-oxoazetidin-1-yl]-1-adamantane carboxylate,
trans-4-[2-(benzo[d][1,3]dioxol-4-yl)-3,3-dimethyl-4-oxoazetidin-1-yl]-1-adamantane carboxylic acid,
trans-4-[2-(benzo[d][1,3]dioxol-4-yl)-3,3-dimethyl-4-oxoazetidin-1-yl]-1-adamantane carboxamide,
trans-4-[2-(isoquinolin-5-yl)-3,3-dimethyl-4-oxoazetidin-1-yl]-1-adamantane carboxamide,
trans-4-[2-(quinoline-5-yl)-3,3-dimethyl-4-oxoazetidin-1-yl]-1-adamantane carboxylic acid,
methyl trans-4-[2-(quinolin-8-yl)-3,3-dimethyl-4-oxoazetidin-1-yl]-1-adamantane carboxylate,
trans-4-[2-(quinolin-8-yl)-3,3-dimethyl-4-oxoazetidin-1-yl]-1-adamantane carboxylic acid,
trans-4-[2-(quinolin-8-yl)-3,3-dimethyl-4-oxoazetidin-1-yl]-1-adamantane carboxyamide,
1-(adamantan-2-yl)-3,3-dimethyl-4-(2,3-dimethoxyphenyl)azetidin-2-one,
1-(adamantan-2-yl)-3,3-dimethyl-4-(4-chlorophenyl)azetidin-2-one,
1-(adamantan-2-yl)-3,3-dimethyl-4-(4-methoxyphenyl)azetidin-2-one,
1-(adamantan-2-yl)-3,3-dimethyl-4-(2,3-difluorophenyl)azetidin-2-one,
1-(adamantan-2-yl)-3,3-dimethyl-4-(3-chloro-2-fluorophenyl)azetidin-2-one,
1-(adamantan-2-yl)-3,3-dimethyl-4-(3,4-dichlorophenyl)azetidin-2-one,
1-(adamantan-2-yl)-3,3-dimethyl-4-(3,4-difluorophenyl)azetidin-2-one,
1-(adamantan-2-yl)-3,3-dimethyl-4-(2-fluoro-3-trifluoromethylphenyl)azetidin-2-one,
1-(adamantan-2-yl)-3,3-dimethyl-4-(3-chloro-4-fluorophenyl)azetidin-2-one,
1-(adamantan-2-yl)-3,3-dimethyl-4-(2-chloro-3-trifluoromethylphenyl)azetidin-2-one,
1-(adamantan-2-yl)-3,3-dimethyl-4-(3,5-dichlorophenyl)azetidin-2-one,
1-(adamantan-2-yl)-3,3-dimethyl-4-(4-fluoro-3-trifluoromethylphenyl)azetidin-2-one,
1-(adamantan-2-yl)-3,3-dimethyl-4-(2-methoxyphenyl)azetidin-2-one,
1-(adamantan-2-yl)-3,3-dimethyl-4-(3-methoxyphenyl)azetidin-2-one,
1-(adamantan-2-yl)-3,3-dimethyl-4-(2,3,5-trifluorophenyl)azetidin-2-one,
1-(adamantan-2-yl)-3,3-dimethyl-4-(3,4,5-trifluorophenyl)azetidin-2-one,
1-(adamantan-2-yl)-3,3-dimethyl-4-(4-isopropylphenyl)azetidin-2-one,
1-(adamantan-2-yl)-3,3-dimethyl-4-(4-t-butylphenyl)azetidin-2-one,
1-(adamantan-2-yl)-3,3-dimethyl-4-(2-fluorophenyl)azetidin-2-one,
1-(adamantan-2-yl)-3,3-dimethyl-4-(2-fluoro-4-methoxyphenyl)azetidin-2-one,
1-(adamantan-2-yl)-3,3-dimethyl-4-(2-trifluoromethylphenyl)azetidin-2-one,
1-(adamantan-2-yl)-3,3-dimethyl-4-(4-trifluoromethoxyphenyl)azetidin-2-one,
1-(adamantan-2-yl)-3,3-dimethyl-4-(4-bromophenyl)azetidin-2-one,
1-(adamantan-2-yl)-3,3-dimethyl-4-(2-chlorophenyl)azetidin-2-one,
1-(adamantan-2-yl)-3,3-dimethyl-4-(naphthalen-1-yl)azetidin-2-one,
trans-1-(5-hydroxyadamantan-2-yl)-3,3-dimethyl-4-(2,3-dichlorophenyl)azetidin-2-one,
trans-1-(5-hydroxyadamantan-2-yl)-3,3-dimethyl-4-(naphthalen-1-yl)azetidin-2-one,
trans-1-(5-hydroxyadamantan-2-yl)-3,3-dimethyl-4-(4-methoxynaphthalen-1-yl)azetidin-2-one,
methyl trans-4-[2-(quinolin-4-yl)-3,3-dimethyl-4-oxoazetidin-1-yl]-1-adamantane carboxylate,
trans-4-[2-(quinolin-4-yl)-3,3-dimethyl-4-oxoazetidin-1-yl]-1-adamantane carboxylic acid,
trans-4-[2-(quinolin-4-yl)-3,3-dimethyl-4-oxoazetidin-1-yl]-1-adamantane carboxyamide, trans-1-(5-fluoroadamantan-2-yl)-3,3-dimethyl-4-(2,3-dichlorophenyl)azetidin-2-one,
1-(adamantan-2-yl)-3,3-dimethyl-4-(3-chlorophenyl)azetidin-2-one,
1-(adamantan-2-yl)-3,3-dimethyl-4-[3,5-bis(trifluoromethyl)phenyl]azetidin-2-one,
1-(adamantan-2-yl)-3,3-dimethyl-4-[4-(methylthio)phenyl]azetidin-2-one,
1-(adamantan-2-yl)-3,3-dimethyl-4-(4-methoxy-2-methylphenyl)azetidin-2-one,
trans-4-[2-(benzo[d][1,3]dioxol-4-yl)-3,3-dimethyl-4-oxoazetidin-1-yl]-N-methyl-1-adamantane carboxyamide,
trans-4-[2-(benzo[d][1,3]dioxol-4-yl)-3,3-dimethyl-4-oxoazetidin-1-yl]-N-ethyl-1-adamantane carboxyamide,
trans-4-[2-(benzo[d][1,3]dioxol-4-yl)-3,3-dimethyl-4-oxoazetidin-1-yl]-N-propyl-1-adamantane carboxyamide,
trans-4-[2-(benzo[d][1,3]dioxol-4-yl)-3,3-dimethyl-4-oxoazetidin-1-yl]-N-hexyl-1-adamantane carboxyamide,
trans-4-[2-(benzo[d][1,3]dioxol-4-yl)-3,3-dimethyl-4-oxoazetidin-1-yl]-N-octyl-1-adamantane carboxyamide,
trans-4-[2-(benzo[d][1,3]dioxol-4-yl)-3,3-dimethyl-4-oxoazetidin-1-yl]-N-cyclopropyl-1-adamantane carboxyamide,
trans-4-[2-(benzo[d][1,3]dioxol-4-yl)-3,3-dimethyl-4-oxoazetidin-1-yl]-N-cyclohexyl-1-adamantane carboxyamide,
trans-4-[2-(benzo[d][1,3]dioxol-4-yl)-3,3-dimethyl-4-oxoazetidin-1-yl]-N-benzyl-1-adamantane carboxyamide,
methyl trans-2-[4-(2-(benzo[d][1,3]dioxol-4-yl)-3,3-dimethyl-4-oxoazetidin-1-yl)-1-adamantane carboxyamide] acetate,
trans-2-[4-(2-(benzo[d][1,3]dioxol-4-yl)-3,3-dimethyl-4-oxoazetidin-1-yl)-1-adamantane carboxyamide]acetic acid,
1-(adamantan-2-yl)-4-(2,5-dihydrobenzo[b]oxepin-9-yl)-3,3-dimethylazetidin-2-one,
1-(adamantan-2-yl)-3,3-dimethyl-4-(benzo[b]oxepan-9-yl)azetidin-2-one,
4-benzyl-1-(adamantan-2-yl)-3,3-dimethylazetidin-2-one,
4-[1-(4-chlorophenyl)cyclopropyl]-1-(adamantan-2-yl)-3,3-dimethylazetidin-2-one,
1-(adamantan-2-yl)-3,3-dimethyl-4-(1-phenylcyclopropyl)azetidin-2-one,
1-(adamantan-2-yl)-4-[1-(4-methoxyphenyl)cyclopropyl]-3,3-dimethylazetidin-2-one,
1-(adamantan-2-yl)-3,3-dimethyl-4-(1-p-tolylcyclopropyl)azetidin-2-one,
4-[1-(benzo[d][1,3]dioxol-5-yl)cyclopropyl]-1-(adamantan-2-yl)-3,3-dimethylazetidin-2-one,
4-[1-(4-bromophenyl)cyclopropyl]-1-(adamantan-2-yl)-3,3-dimethylazetidin-2-one,
1-(adamantan-2-yl)-3,3-dimethyl-4-[1-(pyridin-2-yl)cyclopropyl]azetidin-2-one,
4-[1-(2-chlorophenyl)cyclopropyl]-1-(adamantan-2-yl)-3,3-dimethylazetidin-2-one,
4-[1-(3-chlorophenyl)cyclopropyl]-1-(adamantan-2-yl)-3,3-dimethylazetidin-2-one,
4-[1-(biphenyl-4-yl)cyclopropyl]-1-(adamantan-2-yl)-3,3-dimethylazetidin-2-one,
methyl trans-4-{2-[1-(pyridin-2-yl)cyclopropyl]-3,3-dimethyl-4-oxoazetidin-1-yl}-1-adamantane carboxylate,
trans-4-{2-[1-(pyridin-2-yl)cyclopropyl]-3,3-dimethyl-4-oxoazetidin-1-yl}-1-adamantane carboxylic acid and
trans-4-{2-[1-(pyridin-2-yl)cyclopropyl]-3,3-dimethyl-4-oxoazetidin-1-yl}-1-adamantane carboxyamide.

When an asymmetric carbon atom is present in the 1-adamantyl azetidin-2-one derivative shown by general formula (I) of the present invention, there exists an optical isomer, and the present invention encompasses those optical isomers or any mixtures comprising racemate and the like.

The present invention also encompasses various hydrates or solvates of the 1-adamantyl azetidin-2-one derivative shown by general formula (1) or pharmaceutically acceptable acid-addition salt thereof, and a crystal polymorphic substance of the same.

Examples of pharmaceutically acceptable salt of the 1-adamantyl azetidin-2-one derivative shown by general formula (1) specifically include acid-addition salt and the like treated with an inorganic acid (for example, a hydrochloric acid, hydrobromic acid, hydroiodic acid, sulfuric acid, nitric acid, phosphoric acid, and the like) or an organic acid (for example, a formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid, asparaginic acid, glutamic acid, and the like), base-addition salt and the like treated with inorganic bases (alkali metals such as sodium, potassium and the like; alkaline earth metals such as calcium, magnesium and the like), ammonia or organic bases (trialkylamine, etc.).

Examples of solvates of the 1-adamantyl azetidin-2-one derivative shown by general formula (1) or pharmaceutically acceptable salt thereof include hydrates or various solvates (for example, a solvate with alcohol such as ethanol).

Preparation Method

The 1-adamantyl azetidin-2-one derivative shown by general formula (1) of the present invention can be prepared by the following method or similar method.

1. Preparation Method of a Compound (Ia) Wherein N is "0" in the General Formula (1)

By reacting cyclic amines shown by general formula (II) with aldehyde derivatives shown by general formula (III), an azetidin-2-one derivative (Ia) of interest can be prepared.

The reaction path is shown by the following chemical formula.

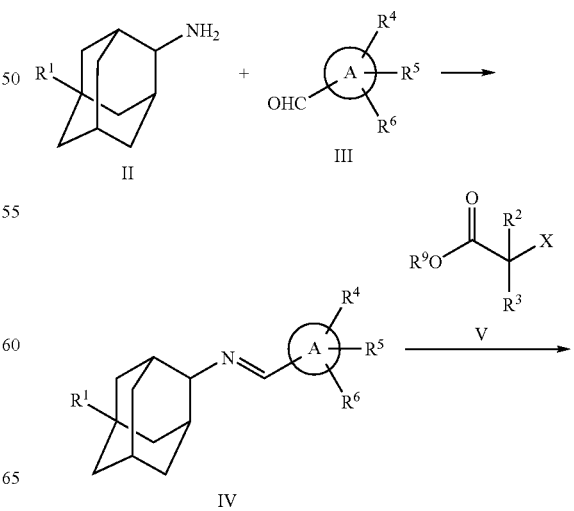

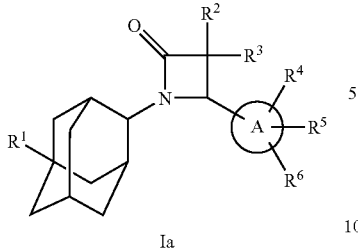

Ia (wherein $R^1$, $R^2$, $R^3$, $R^4$, $R^5$, $R^6$ and A show the same things as they show in the above general formula (1), $R^9$ shows an alkyl group, aryl group or arylalkyl group, and X shows a halogen atom.)

A reaction of an amine compound (II) and aldehyde derivative (III) can be conducted in a solvent in the presence or absence of an acid catalyst. A solvent is not particularly limited, and for example, the followings can be used independently or in combination: tetrahydrofuran, toluene, acetonitrile, methanol, ethanol and the like. An acid catalyst is not particularly limited, and for example, the followings can be used: toluenesulfonic acid, aluminum chloride, titanium (IV) chloride, titanium tetraisopropoxide, scandium triflate, ytterbium triflate and the like. The reaction condition varies depending on the materials used, but generally, an imine derivative (IV) is obtained by conducting the reaction at 0 to 150° C., preferably at 15 to 90° C. for 5 minutes to 24 hours, preferably for 30 minutes to 15 hours.

A reaction of an imine derivative (IV) and α-haloester derivative (V) can be conducted in a solvent in the presence of zinc. A solvent is not particularly limited, and for example, the followings can be used independently or in combination: tetrahydrofuran, toluene, xylene, dioxane, dichloromethane, acetonitrile, propionitrile and the like. The reaction condition varies depending on the materials used, but generally, an 1-adamantyl azetidin-2-one derivative (Ia) of interest is obtained by conducting the reaction at 0 to 200° C., preferably at 50 to 150° C. for 10 minutes to 12 hours, preferably for 30 minutes to 5 hours.

The above amine compound (II) can be prepared by a known method. For example, when $R^1$ is a hydroxyl group or methoxycarbonyl group, it may be referred to the method described in US Patent Publication No. US2006/0148871. Further, when $R^1$ is a hydrogen atom, 2-adamantylamine commercialized by Aldrich may be used as a raw material. Further, when $R^1$ is a chlorine atom, 5-chloro-2-adamantanone commercialized by Alfa Aesar may be used as a raw material.

As for the above haloester derivative (V), a commercialized product can be used. For example, as for ethyl 2-bromoisobutyrate, those commercialized by Aldrich and Tokyo Chemical Industry, Co., Ltd. can be used.

As for a 1-adamantyl azetidin-2-one derivative wherein $R_1$ is a carboxyl group or carboxyamide group, an azetidin-2-one derivative (IX) of interest can be prepared by the following reaction path.

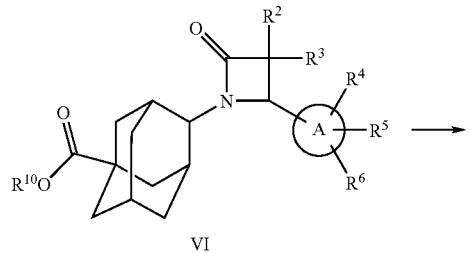

VI

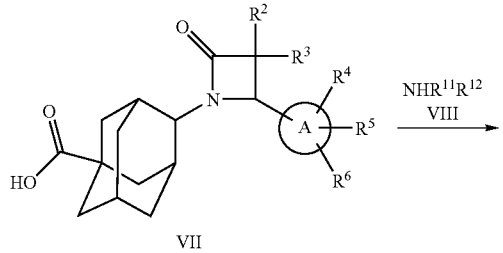

VII (wherein $R^2$, $R^3$, $R^4$, $R^5$, $R^6$ and A show the same things as they show in the above general formula (1), $R^{10}$ shows an alkyl group, aryl group, or arylalkyl group, and $R^{11}$ and $R^{12}$ are the same or different and show a hydrogen atom, an alkyl group or cycloalkyl group that may have a substituent.)

A carboxylic acid ester derivative (VI) is subjected to a usual hydrolysis reaction to yield a carboxylic acid derivative (VII). The reaction can be conducted in a solvent in the presence of a base or acid. A solvent is not particularly limited, and for example, the followings can be used independently or in combination: tetrahydrofuran, dioxane, methanol, ethanol, water and the like. A base is not particularly limited, and for example, the followings can be used: alkali metal hydroxides such as sodium hydroxide and potassium hydroxide; alkali metal carbonates such as lithium carbonate, sodium carbonate, potassium carbonate, and cesium carbonate; potassium trimethylsilanolate and the like. An acid is not particularly limited, and the followings can be used: hydrochloric acid, acetic acid, trifluoroacetic acid, boron tribromide, aluminum chloride and the like. The reaction condition varies depending on the materials used, but generally, a carboxylic acid derivative (VII) is obtained by conducting the reaction at −20 to 100° C., preferably at 15 to 50° C. for 5 minutes to 1 day, preferably for 1 hour to 12 hours.

A dehydration-condensation reaction of the carboxylic acid derivative (VII) with an amine compound (VIII) can be conducted in a solvent using a condensation agent in the presence or absence of a base, and in the presence or absence of a condensation accelerator. A solvent is not particularly limited, and for example, the followings can be used: 1,2-dichloroethane, chloroform, dichloromethane, ethyl acetate, isopropyl acetate, toluene, benzene, tetrahydrofuran, dioxane, acetonitrile, propionitrile, N,N-dimethylformamide, N-methylpyrrolidone and the like. A base is not particularly limited, and for example, the followings can be used: organic bases such as pyridine, N,N-dimethylaminopyridine (DMAP), collidine, lutidine, 1,8-diazabicyclo[5.4.0]undecene (DBU), 1,5-diazabicyclo[4.3.0]nonene (DBN), 1,4-diazabicyclo[2.2.2]octane (DABCO), triethylamine, diisopropylethylamine, diisopropylpentylamine, and trimethylamine; alkali metal hydrides such as lithium hydride, sodium hydride, and potassium hydride; alkali metal hydroxides such as lithium hydroxide, sodium hydroxide, and potassium hydroxide; alkali metal carbonates such as lithium carbonate, sodium carbonate, potassium carbonate, and cesium carbonate; and bicarbonates such as sodium hydrogen carbonate and potassium hydrogen carbonate. A condensation accelerator is not particularly limited, and DMAP, 1-hydroxy-7-azobenzotriazole (HOAt), 1-hydroxybenzotriazole (HOST), 3-hydroxy-3,4-dihydro-4-oxo-1,2,3-benzotriazole (HODhbt), N-hydroxy-5-norbornene-2,3-dicarboximide (HONB), pentafluorophenol (HOPfp), N-hydroxyphthalimide (HOPht), N-hydroxysuccinimide (HOSu) etc. can be used. A condensation agent is not particularly limited, and N,N'-dicyclohexylcarbodiimide (DCC), N,N'-diisopropylcarbodiimide (DIPCI), 1-ethyl-3-(3-(dimethylaminopropyl)carbodiimide (WSCI), 1-ethyl-3-(3-dimethylaminopropyl)carbodiimide hydrochloride (WSC.HCl), diethyl cyanophosphate (DEPC), benzotriazol-1-yl-oxy-tris (dimethylamino)phosphonium hexafluorophosphate (BOP), benzotriazol-1-yl-oxy-tris(pyrrolidinylamino)phosphonium hexafluorophosphate (PyBOP), 2-(1H-benzotriazol-1-yl)-1,1,3,3-tetramethyluronium tetrafluoroborate (TBTU) and the like can be used. The reaction condition varies depending on the materials used, but generally, 1-adamantyl azetidin-2-one derivative (IX) of interest is obtained by conducting the reaction at −20 to 100° C., preferably at 0 to 30° C. for 5 minutes to 1 day, preferably for 1 hour to 12 hours.

As for a 1-adamantyl azetidin-2-one derivative wherein $R_1$ is fluorine, the azetidin-2-one derivative (XI) of interest can be prepared by the following reaction path.

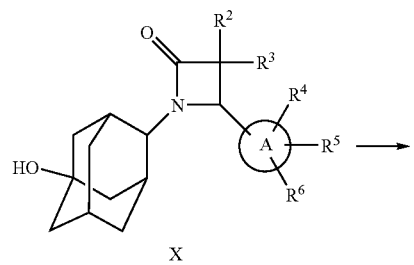

(wherein $R^2$, $R^3$, $R^4$, $R^5$, $R^6$ and A show the same things as they show in the above general formula (1)).

By reacting the compound (X) with a fluorinating agent, an azetidin-2-one derivative (XI) of interest can be obtained. The reaction can be conducted in a solvent, in the presence of a fluorinating agent. The fluorinating agent is not particularly limited, and for example, (diethylamino) sulfur trifluoride, potassium fluoride, pyridinium poly(hydrogen fluoride) and the like can be used. A solvent is not particularly limited, and for example, the followings can be used independently or in combination: tetrahydrofuran, dioxane, diethylether, dichloromethane, chloroform, etc. The reaction condition varies depending on the materials used, but generally, an azetidin-2-one derivative (XI) is obtained by conducting the reaction at −78 to 100° C., preferably at −10 to 50° C. for 5 minutes to 1 day, preferably for 1 hour to 12 hours.

As a cyclic compound (III) used in the above preparation method, an available compound can be used directly, or can be produced appropriately by a known method, or according to the same. For example, a compound shown by general formula (XII) among the cyclic compounds (III) can be prepared by the following method, but it is not limited to this method.

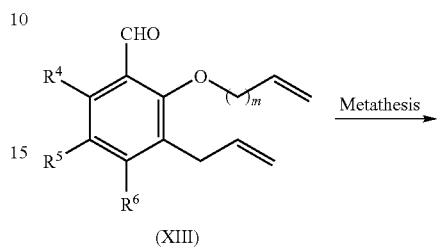

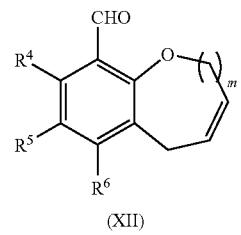

(wherein $R^4$, $R^5$ and $R^6$ show the same things as they show in the above general formula (1), and m shows 0 to 4).

For the ring closing methathesis reaction of a compound (XIII) to a compound (XII), a reaction technique conducted in a solvent, in the presence of a methathesis catalyst may be applied. A methathesis catalyst is not particularly limited, but the Grubbs first generation catalyst, the Grubbs second generation catalyst, the Hoveyda-Grubbs first generation catalyst, the Hoveyda-Grubbs second generation catalyst and the like may be used independently or in combination. A solvent is not particularly limited, and for example, the followings may be used independently or in combination: dichloromethane, toluene, tetrahydrofuran, dioxane, etc. The reaction condition varies depending on the materials used, but generally, a subject of interest is obtained by conducting the reaction at −20 to 180° C., preferably at 0 to 60° C. for 5 minutes to 3 days, preferably for 10 minutes to 24 hours.

For example, a compound shown by formula (XIV) among the compounds (I) can be prepared by the following method, but it is not limited to this method.

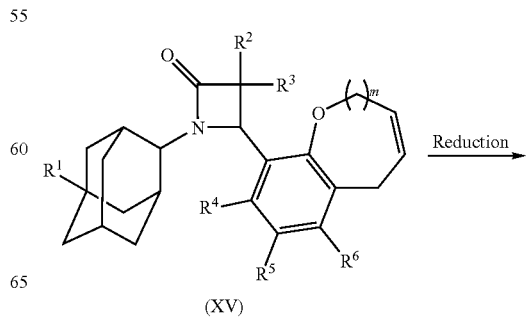

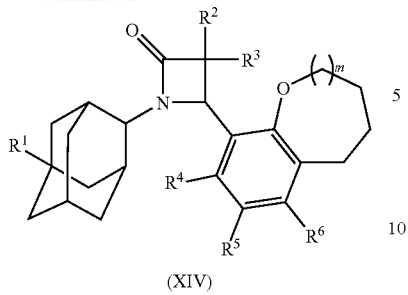

(XIV)

(wherein $R^1$, $R^2$, $R^3$, $R^4$, $R^5$ and $R^6$ show the same things as they show in the above general formula (1), and m shows 0 to 4).

As a reduction reaction of a compound shown by general formula (XV), a usual method for converting an alkenyl group to alkyl group can be applied, and for example, a catalytic reduction using a metal catalyst and hydrogen source can be used. A hydrogen source for hydrogenation is not particularly limited, and hydrogen, formic acid, ammonium formate, cyclohexadiene and the like can be used. A hydrogenation catalyst is not particularly limited, and the followings can be used: palladium carbon, palladium black, platinum black, platinum dioxide, Raney nickel, palladium carbon hydroxide powder and the like. A solvent is not particularly limited, and for example, the followings can be used independently or in combination: methanol, ethanol, isopropanol, ethyl acetate, isopropyl acetate, N,N-dimethylformamide, tetrahydrofuran, dioxane, acetonitrile, acetic acid and water. The reaction condition varies depending on the compound used shown by general formula (XV), but generally, a substance of interest is obtained by conducting the reaction at 0 to 150° C., preferably at 0 to 100° C. for 5 minutes to 3 days, preferably for 30 minutes to 50 hours.

2. Preparation Method for a Compound (Ib) Wherein n is "1" in the General Formula (1)

By reacting an imine derivative shown by general formula (XVII) and α-haloester derivative shown by formula (V), an 1-adamantyl azetidin-2-one derivative (Ib) of interest can be prepared. The reaction path is shown by the following chemical formula.

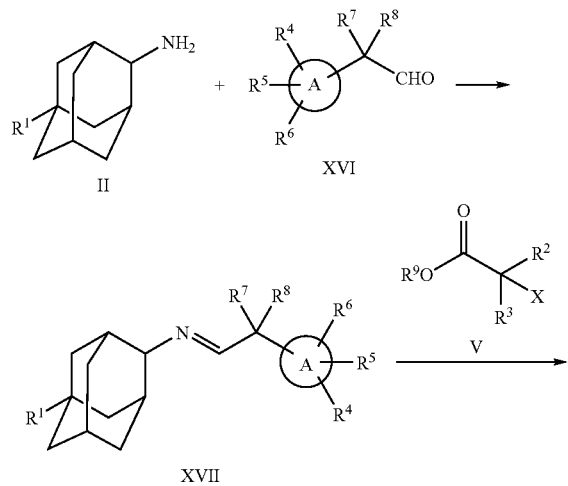

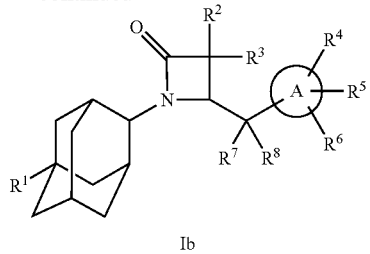

Ib (wherein A ring, $R^1$, $R^2$, $R^3$, $R^4$, $R^5$, $R^6$, $R^7$, and $R^8$ show the same things as they show in the above general formula (1), $R^9$ shows an alkyl group, aryl group or arylalkyl group, and X shows a halogen atom.)

A reaction of an amine derivative (II) and aldehyde derivative (XVI) can be conducted in a solvent in the absence of a catalyst. A solvent is not particularly limited, and for example, the followings can be used independently or in combination: tetrahydrofuran, benzene, toluene, acetonitrile, methanol, ethanol and the like. The reaction condition varies depending on the materials and reagents used, but generally, an imine derivative (XVII) is obtained by conducting the reaction at 0 to 150° C., preferably at 15 to 90° C. for 5 minutes to 24 hours, preferably for 30 minutes to 15 hours.

A reaction of an imine derivative (XVII) and haloester derivative (V) can be conducted in a solvent in the presence of zinc. A solvent is not particularly limited, and for example, the followings can be used independently or in combination: toluene, benzene, xylene, dioxane, dichloroethane and the like. As zinc, zinc in a powder form is preferred. The reaction condition varies depending on the materials used, but generally, an 1-adamantyl azetidin-2-one derivative (Ib) of interest is obtained by conducting the reaction at 0 to 200° C., preferably at 50 to 150° C. for 5 minutes to 48 hours, preferably for 1 hour to 24 hours.

When $R^1$ is a hydroxyl group, or any one of $R^4$, $R^5$ and $R^6$ is an amino group, each substituent thereof can be protected or deprotected with a protection group generally used. Each hydroxyl group and amino group can be modified with the acylation or sulfonylation condition generally used. Further, when $R^4$, $R^5$ and $R^6$ and are a $C_{1-6}$ alkylsulfinyl group or $C_{1-6}$ alkylsulfonyl group, a sulfur atom of the corresponding alkylthio group can be oxidized by a common method.

An aldehyde derivative (XVI) used in the above preparation method can be prepared by a method described previously, or according thereto, for example by the following reaction formula.

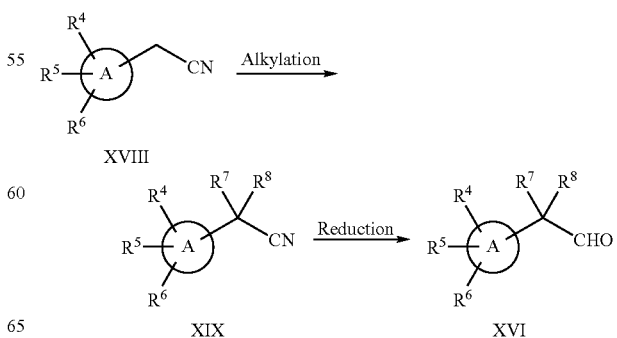

(wherein A ring, $R^4$, $R^5$, $R^6$, $R^7$ and $R^8$ show the same things as they show in the above).

The alkylation reaction of a compound (XVIII) may be referred to WO2005/019161 when $R^7$ and $R^8$ are —$CH_2$—$CH_2$—.

The reduction reaction of a nitrile derivative (XIX) can be conducted in a solvent in the presence of a base. A solvent is not particularly limited, and for example, the followings can be used independently or in combination: toluene, benzene, dichloromethane, dichloroethane, tetrahydrofuran, diethylether, dimethoxyethane and the like. A base is not particularly limited, and for example, lithium diisobutylaluminum hydride, lithium triethoxy aluminum hydride, triethyloxonium tetrafluoroborate and the like can be used. The reaction condition varies depending on the materials and reagents used, but generally, an aldehyde derivative (XVI) is obtained by conducting the reaction at −80 to 50° C., preferably at −40 to 40° C. for 5 minutes to 24 hours, preferably for 30 minutes to 3 hours.

When the following carboxylic acid derivative (XX) can be obtained, an aldehyde derivative (XVI) can be prepared by a method described previously, or according thereto, for example by the following reaction formula.

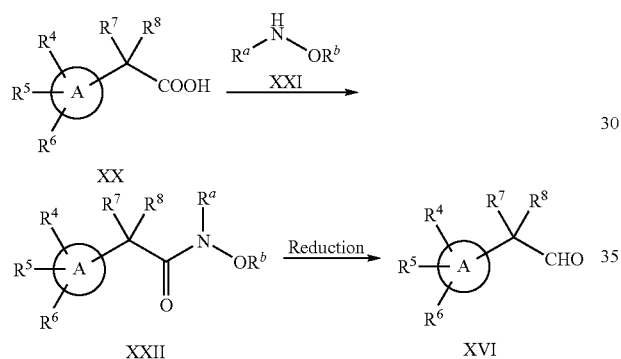

(wherein A ring, $R^4$, $R^5$, $R^6$, $R^7$ and $R^8$ show the same things as they show in the above, and $R^a$ and $R^b$ show an alkyl group).

A dehydration-condensation reaction of the carboxylic acid derivative (XX) with a hydroxylamine derivative (XXI) can be conducted in a solvent using a condensation agent in the presence or absence of a base, and in the presence or absence of a condensation accelerator. A solvent is not particularly limited, and for example, the followings can be used independently or in combination: 1,2-dichloroethane, chloroform, dichloromethane, ethyl acetate, isopropyl acetate, toluene, benzene, tetrahydrofuran, dioxane, acetonitrile, propionitrile, N,N-dimethylformamide, N-methylpyrrolidone, water and the like. A base is not particularly limited, and for example, the followings can be used: organic bases such as pyridine, DMAP, collidine, lutidine, DBU, DBN, DABCO, triethylamine, diisopropylethylamine, diisopropylpentylamine, and trimethylamine; alkali metal hydrides such as lithium hydride, sodium hydride, and potassium hydride; alkali metal hydroxides such as lithium hydroxide, sodium hydroxide, and potassium hydroxide; alkali metal carbonates such as lithium carbonate, sodium carbonate, potassium carbonate, and cesium carbonate; and alkali metal bicarbonates such as sodium hydrogen carbonate and potassium hydrogen carbonate. A condensation accelerator is not particularly limited, and DMAP, HOAt, HOBt, HODhbt, HONB, HOPfp, HOPht, HOSu etc. can be used. A condensation agent is not particularly limited and DCC, DIPCI, WSCI, WSC.HCl, DEPC, BOP, PyBOP, TBTU and the like can be used. The reaction condition varies depending on the materials and reagents used, but generally, an amide derivative (XXII) of interest is obtained by conducting the reaction at −20 to 100° C., preferably at 0 to 40° C. for 5 minutes to 1 day, preferably for 10 minutes to 12 hours.

The reduction reaction of an amide derivative (XXII) can be conducted in a solvent, in the presence of a base. A solvent is not particularly limited, and for example, the followings can be used independently or in combination: toluene, benzene, dichloromethane, dichloroethane, tetrahydrofuran, diethylether, dimethoxyethane and the like. A base is not particularly limited, and for example, lithium diisobutylaluminum hydride, lithium aluminum hydride and the like can be used. The reaction condition varies depending on the materials used, but generally, an aldehyde derivative (XVI) is obtained by conducting the reaction at −100 to 20° C., preferably at −80 to 0° C. for 5 minutes to 24 hours, preferably for 30 minutes to 3 hours.

When a carboxylic acid derivative (XX) can be obtained, an aldehyde derivative (XVI) can be also prepared by a method described previously, or according thereto, for example by the following reaction formula.

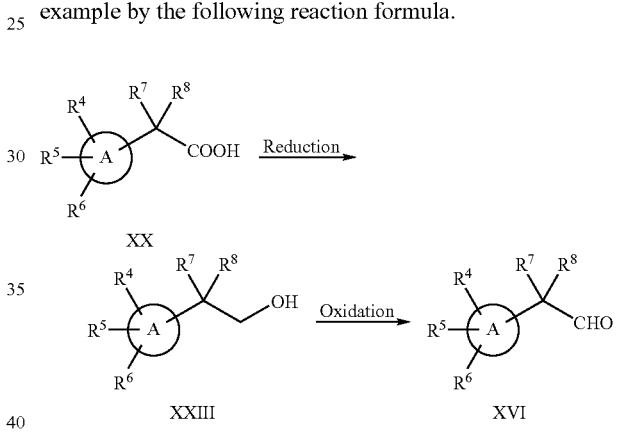

(wherein A ring, $R^4$, $R^5$, $R^6$, $R^7$, and $R^8$ show the same things as they show in the above).

The reduction reaction of a carboxylic acid derivative (XX) can be conducted in a solvent by using a reductant. A solvent is not particularly limited, and for example, the followings can be used independently or in combination: toluene, benzene, dichloromethane, dichlorethane, tetrahydrofuran, diethylether, dimethoxyethane and the like. A reductant is not particularly limited, and for example, diisobutylaluminum lithium, lithium aluminum hydride, lithium borohydride, borane-dimethyl sulfide, 9-borabicyclo[3.3.1]nonane, etc. can be used. The reaction condition varies depending on the materials and reagents used, but generally, an alcohol derivative (XXIII) is obtained by conducting the reaction at −80 to 50° C., preferably at −40 to 40° C. for 5 minutes to 24 hours, preferably for 30 minutes to 3 hours.

The oxidation reaction of an alcohol derivative (XXIII) can be conducted in a solvent, in the presence of an oxidant. A solvent is not particularly limited, and for example, the followings can be used independently or in combination: toluene, benzene, dichloromethane, dichloroethane, tetrahydrofuran, diethylether, dimethoxyethane and the like. An oxidant is not particularly limited, and for example, the following can be used: dimethyl sulfoxide-oxalyl chloride, pyridinium chlorochromate, pyridinium dichromate, Dess-Martin periodinane, chromic acid, hypochlorous acid, 2,2,6,6-tetramethyl piperidine 1-oxyl, manganese dioxide, lead tetraacetate, 2-iodoxybenzoic acid, tetrapropylammonium perruthenate, N-tert-butylbenzene sulfide imidoyl chloride, 1-methyl-2-azaadamantan N-oxyl, aluminum isopropoxide, dimethyl sulfide-N-chlorosuccinimide, etc. The reaction condition varies depending on the materials and reagents used, but generally, an aldehyde derivative (XVI) is obtained by conducting the reaction at −80 to 50° C., preferably at −40 to 40° C. for 5 minutes to 24 hours, preferably for 30 minutes to 3 hours.

As for the aldehyde derivative (XVI), a commercialized reagent can be used. Examples of commercialized reagent include phenyl acetaldehyde, 2-phenylpropionaldehyde and 1-phenylcyclopropane carboaldehyde, but it is not limited to these.

Further, among the compounds (Ib), a compound represented by formula (XXVI) can be prepared by the following method, but it is not limited to this.

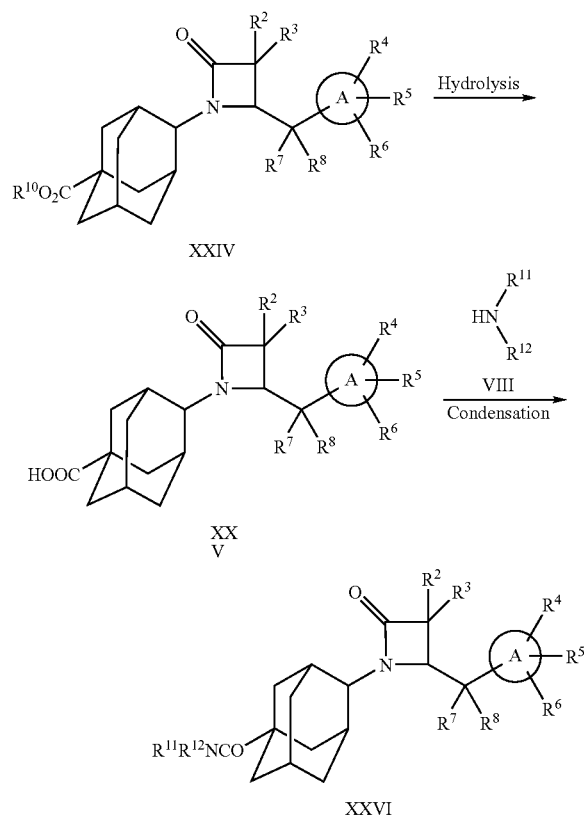

(wherein A ring, $R^4$, $R^5$, $R^6$, $R^7$ and $R^8$ show the same things as they show in the above, $R^{10}$ shows an alkyl group, aryl group or arylalkyl group, $R^{11}$ and $R^{12}$ may be the same or different, and show a hydrogen atom, or an alkyl group or cycloalkyl group that may have a substituent).

An ester derivative (XXIV) is subjected to a usual hydrolysis reaction to yield a carboxylic acid derivative (XXV). The reaction can be conducted in a solvent in the presence of a base or acid. A solvent is not particularly limited, and for example, the followings can be used independently or in combination: tetrahydrofuran, dioxane, methanol, ethanol, water and the like. A base is not particularly limited, and for example, the followings can be used: alkali metal hydroxides such as sodium hydroxide and potassium hydroxide; alkali metal carbonates such as lithium carbonate, sodium carbonate, potassium carbonate, and cesium carbonate; potassium trimethylsilanolate and the like. An acid is not particularly limited, and the followings can be used: hydrochloric acid, acetic acid, trifluoroacetic acid, boron tribromide, aluminum trichloride, etc. The reaction condition varies depending on the materials and reagents used, but generally, a carboxylic acid derivative (XXV) is obtained by conducting the reaction at −20 to 100° C., preferably at 15 to 50° C. for 5 minutes to 1 day, preferably for 30 minutes to 13 hours.

A dehydration-condensation reaction of the carboxylic acid derivative (XXV) with an amine compound (VIII) can be conducted in a solvent using a condensation agent in the presence or absence of a base, and in the presence or absence of a condensation accelerator. A solvent is not particularly limited, and for example, the followings can be used independently or in combination: 1,2-dichloroethane, chloroform, dichloromethane, ethyl acetate, isopropyl acetate, toluene, benzene, tetrahydrofuran, dioxane, acetonitrile, propionitrile, N,N-dimethylformamide, N-methylpyrrolidone, water and the like. A base is not particularly limited, and for example, the followings can be used: organic bases such as pyridine, DMAP, collidine, lutidine, DBU, DBN, DABCO, triethylamine, diisopropylethylamine, diisopropylpentylamine, and trimethylamine; alkali metal hydrides such as lithium hydride, sodium hydride, and potassium hydride; alkali metal hydroxides such as lithium hydroxide, sodium hydroxide, and potassium hydroxide; alkali metal carbonates such as lithium carbonate, sodium carbonate, potassium carbonate, and cesium carbonate; and alkali metal bicarbonates such as sodium hydrogen carbonate and potassium hydrogen carbonate. A condensation accelerator is not particularly limited, and DMAP, HOAt, HOBt, HODhbt, HONB, HOPfp, HOPht, HOSu etc. can be used. A condensation agent is not particularly limited, and DCC, DIPCI, WSCI, WSC.HCl, DEPC, BOP, PyBOP, TBTU and the like can be used. The reaction condition varies depending on the materials and reagents used, but generally, a compound of interest (XXVI) is obtained by conducting the reaction at −20 to 100° C., preferably at 0 to 30° C. for 5 minutes to 1 day, preferably for 30 minutes to 12 hours. When $R^4$, $R^5$ and $R^6$ are a hydroxyl group or amino group, each substituent thereof can be protected or deprotected with a protection group generally used. Each hydroxyl group and amino group can be modified with the aceylation or sulfonylation condition generally used. Further, when $R^4$, $R^5$ and $R^6$ are a $C_{1-6}$ alkylsulfonyl group, a sulfur atom of the corresponding $C_{1-6}$ alkylthio group can be oxidized by a common method for preparing the above compound.

Further, among the compounds (Ib), a compound represented by formula (XXIX) can be prepared by the following method, but it is not limited to this.

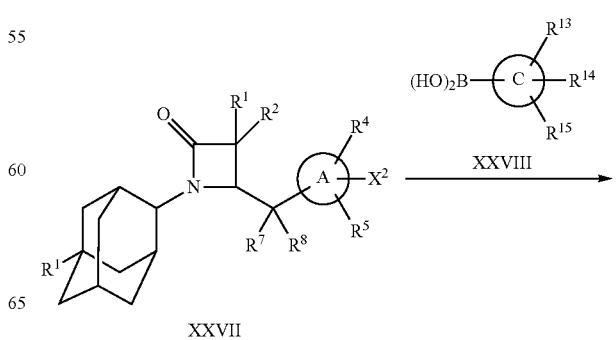

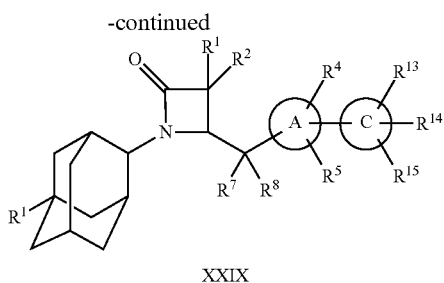

XXIX (wherein A ring, R¹, R², R³, R⁴, R⁵, R⁶, R⁷ and R⁸ show the same things as they show in the above, R¹³, R¹⁴ and R¹⁵ show the same things as R⁴ and R⁵, C ring show the same things as A ring, and X² shows a halogen atom).

The coupling reaction of a compound (XXVII) and boron acid derivative (XXVIII) can be conducted in a solvent, in the presence of a base and in the presence of a catalyst. A solvent is not particularly limited and for example, the followings can be used independently or in combination: 1,2-dichloroethane, chloroform, dichloromethane, ethyl acetate, isopropyl acetate, toluene, benzene, tetrahydrofuran, dioxane, diethylether, acetonitrile, propionitrile, N,N-dimethylformamide, N-methylpyrrolidone, ethanol, methanol, butanol, water and the like. A base is not particularly limited, and for example, the followings can be used: organic bases such as pyridine, DMAP, collidine, lutidine, DBU, DBN, DABCO, triethylamine, diisopropylethylamine, diisopropylpentylamine, and trimethylamine; alkali metal alkoxides such as sodium methoxide, potassium methoxide, sodium ethoxide, potassium ethoxide, sodium tert-butoxide and potassium tert-butoxide; alkali metal hydrides such as lithium hydride, sodium hydride, and potassium hydride; alkali metal hydroxides such as lithium hydroxides, sodium hydroxides and potassium hydroxides; alkali earth metal hydroxides such as barium hydroxide and calcium hydroxide; alkali metal carbonates such as lithium carbonate, sodium carbonate, potassium carbonate and cesium carbonate; alkali metal bicarbonates such as sodium hydrogen carbonate and potassium hydrogen carbonate; phosphorylated alkali metal such as potassium phosphate and sodium phosphate; alkali metal fluorides such as potassium fluoride and cesium fluoride; transition metal hydroxides such as thallium hydroxide. A catalyst is not particularly limited, and for example the followings can be used: palladium acetate, tetrakis(triphenylphosphine)palladium, 1,1'-bis (diphenylphosphino)ferrocene]dichloropalladium, bis(1,5-cyclooctadiene)nickel. The reaction condition varies depending on the materials and reagents used, but generally, a compound of interest (XXIX) is obtained by conducting the reaction at −20 to 200° C., preferably at 20 to 150° C. for 5 minutes to 2 days, preferably for 30 minutes to 24 hours. When R⁴, R⁵, R¹³, R¹⁴ and R¹⁵ are a hydroxyl group or amino group, each substituent thereof can be protected or deprotected with a protection group generally used. Moreover, each hydroxyl group and amino group can be modified with an acyl group or sulfonyl group generally used. Further, when R⁴, R⁵, R¹³, R¹⁴ and R¹⁵ are a C₁₋₆ alkylthio group, a corresponding sulfur atom can be turned into a sulfonyl group by using a common oxidation reaction of a sulfur atom.

The intermediates and substances of interest obtained in each of the above reactions can be isolated and purified as desired by subjecting to a purification method that are used routinely in the field of organic synthetic chemistry, for example, filtration, extraction, washing, drying, condensation, recrystallization, various types of chromatography and the like. Alternatively, the intermediates can be used for next reactions without a particular purification.

Further, various isomers can be isolated by applying a routine procedure utilizing the difference in physical-chemical property between the isomers. For example, a racemic mixture can be led to optically-pure isomers by a common racemic resolution method such as an optical resolution method comprising leading a mixture to diastereomeric salt with a common optically-active acid such as tartaric acid, or a method using optically-active column chromatography. Further, a diastereomeric mixture can be separated by a fractional crystallization, various types of chromatography or the like. Alternatively, an optically-active compound can be produced by using an appropriate optically-active material.

Embodiments of Use

The pharmaceutical composition of the present invention comprises the 1-adamantyl azetidin-2-one derivative shown by general formula (1), pharmaceutically acceptable salt thereof, or their solvate as an active ingredient. The compound of the present invention can be used independently, but generally, the compound is used in combination with a pharmaceutically acceptable carrier and/or diluent.

Examples of an administration form of a medicine that comprises 1-adamantyl azetidin-2-one derivative of the present invention or salt thereof, or their solvate as an active ingredient include an oral administration by a tablet, capsule, granules, powder, syrup or the like; or a parenteral administration by an intravenous injection, intramuscular injection, suppository, inhaler, percutaneous absorption, eye-drops, nasal preparation or the like. Further, to prepare a pharmaceutical formulation in such various forms, the active ingredient can be prepared independently or as a pharmaceutical composition where appropriate, by combining with other pharmaceutically acceptable carriers, specifically an excipient, binder, extender, disintegrant, surfactant, lubricant, dispersant, buffer, preservative, flavoring agent, flavor, coating agent, diluent or the like.

The dose of the medicine of the present invention varies depending on weight, age, sex, symptoms and the like of the patient, but generally, in a case of an adult, 1-adamantyl azetidin-2-one derivative represented by general formula (1) can be administered in an amount of 0.1 to 1000 mg, in particular 1 to 300 mg a day, as a single or several separate doses either orally or parenterally.

EXAMPLE

The present invention will be further described with reference to the following examples, while the scope of the present invention will not be limited to these examples.

Example 1

Preparation of 1-(adamantan-2-yl)-3,3-dimethyl-4-phenylazetidin-2-one

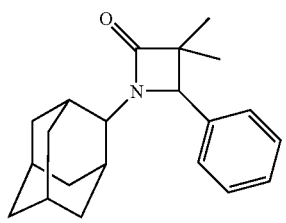

A solution of 2-adamantylamine (50.0 mg, 0.330 mmol) in ethanol (2 mL) was added with benzaldehyde (56.3 mg, 0.330 mmol) at room temperature, and the resultant was stirred at the same temperature for 1.5 hours. The reaction solution was concentrated in vacuo. The obtained residue was dissolved in toluene (5 mL), and sequentially added with ethyl 2-bromoisobutyrate (109 mg, 0.660 mmol) and zinc (432 mg, 6.60 mmol) at room temperature. The reaction solution was stirred at 130° C. for 5 hours, and added with hydrochloric acid, and extracted with ethyl acetate. The organic layer was dried with anhydrous sodium sulfate, and concentrated in vacuo. The obtained residue was purified using preparative thin-layer chromatography (hexane:ethyl acetate=3:1), and 1-(adamantan-2-yl)-3,3-dimethyl-4-phenylazetidin-2-one (65.4 mg, 64.0%) was obtained as a white crystalline powder.

$^1$H-NMR (400 MHz, CDCl$_3$) δ; 0.72 (s, 3H), 1.47 (s, 3H), 1.52-1.88 (m, 12H), 2.00-2.14 (m, 1H), 2.89 (s, 1H), 3.63 (s, 1H), 4.39 (s, 1H), 7.21 (d, J=7.1 Hz, 2H), 7.28-7.39 (m, 3H).

IR (ATR); 2907, 1729, 1461, 1329, 1110, 704 cm$^{-1}$.

EI-MS m/z; 309 (M$^+$).

Example 2

Preparation of 1-(adamantan-2-yl)-3,3-dimethyl-4-(2,3-dichlorophenyl)azetidin-2-one

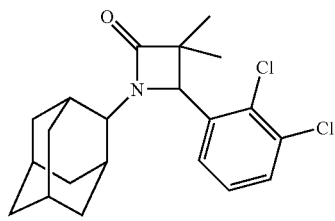

2,3-Dichlorobenzaldehyde was used in place of benzaldehyde for a similar reaction and treatment as Example 1, and the title compound was obtained as a white amorphous solid.

$^1$H-NMR (400 MHz, CDCl$_3$) δ; 0.73 (s, 3H), 1.58 (s, 3H), 1.60-2.12 (m, 13H), 2.93 (s, 1H), 3.67 (s, 1H), 4.89 (s, 1H), 7.21 (dd, J=1.7, 7.8 Hz, 1H), 7.27 (t, J=7.8 Hz, 1H), 7.42 (dd, J=1.7, 7.8 Hz, 1H).

IR (ATR); 2907, 1747, 1422, 1327, 1111, 796 cm$^{-1}$.

FAB-MS m/z; 378 (M+H)$^+$.

Example 3

Preparation of trans-1-(5-chloroadamantan-2-yl)-3,3-dimethyl-4-(2,3-dichlorophenyl)azetidin-2-one

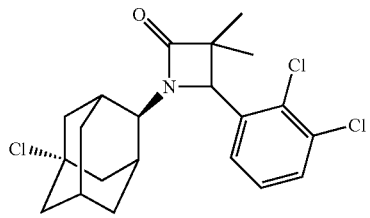

trans-5-Chloro-2-adamantylamine was used in place of 2-adamantylamine, and 2,3-dichlorobenzaldehyde in place of benzaldehyde for a similar reaction and treatment as Example 1, and the title compound was obtained as a white amorphous solid.

$^1$H-NMR (400 MHz, CDCl$_3$) δ; 0.74 (s, 3H), 1.54-2.36 (m, 15H), 3.16 (s, 1H), 3.67 (s, 1H), 4.89 (s, 1H), 7.16 (d, J=8.0 Hz, 1H), 7.23-7.30 (m, 1H), 7.43 (dd, J=1.8, 7.7 Hz, 1H).

IR (ATR); 2922, 1748, 1423, 1188, 1116, 746 cm$^{-1}$.

Example 4

Preparation of cis-1-(5-chloroadamantan-2-yl)-3,3-dimethyl-4-(2,3-dichlorophenyl)azetidin-2-one

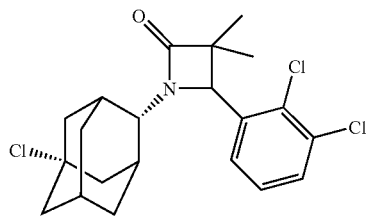

cis-5-Chloro-2-adamantylamine was used for a similar reaction and treatment as Example 3, and the title compound was obtained as a white amorphous solid.

$^1$H-NMR (400 MHz, CDCl$_3$) δ; 0.75 (s, 3H), 1.58-2.33 (m, 15H), 3.11 (s, 1H), 3.72 (s, 1H), 4.94 (s, 1H), 7.11 (d, J=8.0 Hz, 1H), 7.22-7.29 (m, 1H), 7.43 (d, J=7.6 Hz, 1H).

IR (ATR); 2922, 1748, 1423, 1191, 1109, 747 cm$^{-1}$.

Example 5

Preparation of trans-1-(5-chloroadamantan-2-yl)-3,3-dimethyl-4-(naphthalen-1-yl)azetidin-2-one

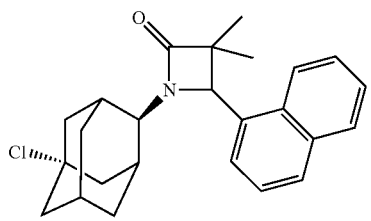

trans-5-Chloro-2-adamantylamine was used in place of 2-adamantylamine, and 1-naphthaldehyde in place of benzaldehyde for a similar reaction and treatment as Example 1, and the title compound was obtained as a white amorphous solid.

$^1$H-NMR (400 MHz, CDCl$_3$) δ; 0.64 (s, 3H), 1.64-2.42 (m, 15H), 3.27 (s, 1H), 3.84 (s, 1H), 5.24 (s, 1H), 7.46-7.54 (m, 4H), 7.80-7.91 (m, 3H).

IR (ATR); 2920, 1743, 1450, 1331, 1117, 779 cm$^{-1}$.

Example 6

Preparation of cis-1-(5-chloroadamantan-2-yl)-3,3-dimethyl-4-(naphthalen-1-yl)azetidin-2-one

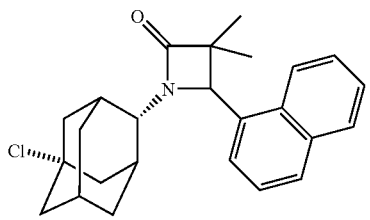

cis-5-Chloro-2-adamantylamine was used for a similar reaction and treatment as Example 5, and the title compound was obtained as a white amorphous solid.

$^1$H-NMR (400 MHz, CDCl$_3$) δ; 0.66 (s, 3H), 1.55-2.32 (m, 15H), 3.21 (s, 1H), 3.90 (s, 1H), 5.29 (s, 1H), 7.45-7.58 (m, 4H), 7.81 (d, J=8.3 Hz, 1H), 7.89-7.92 (m, 2H).

IR (ATR); 2922, 1744, 1450, 1337, 1108, 779 cm$^{-1}$.

Example 7

Preparation of methyl trans-4-[2-(2,3-dichlorophenyl)-3,3-dimethyl-4-oxoazetidin-1-yl]-1-adamantane carboxylate

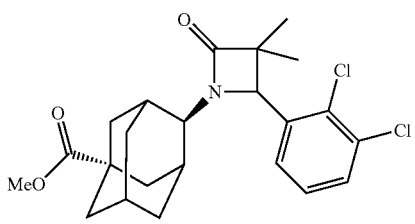

Methyl trans-4-adamantylamine-1-carboxylate was used in place of 2-adamantylamine, and 2,3-dichlorobenzaldehyde in place of benzaldehyde for a similar reaction and treatment as Example 1, and the title compound was obtained as a white amorphous solid.

$^1$H-NMR (400 MHz, CDCl$_3$) δ; 0.74 (s, 3H), 1.59 (s, 3H), 1.68-2.11 (m, 12H), 3.07 (s, 1H), 3.64 (s, 3H), 3.65 (s, 1H), 4.88 (s, 1H), 7.19 (dd, J=1.5, 7.8 Hz, 1H), 7.27 (t, J=7.8 Hz, 1H), 7.43 (dd, J=1.5, 8.0 Hz, 1H).

IR (ATR); 2929, 1748, 1730, 1424, 1236, 1079, 745 cm$^{-1}$.
EI-MS m/z; 436 (M$^+$+1).

Example 8

Preparation of trans-9-[2-(2,3-dichlorophenyl)-3,3-dimethyl-4-oxoazetidin-1-yl]-1-adamantane carboxylic acid

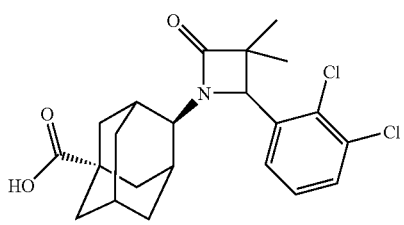

A solution of methyl trans-4-[2-(2,3-dichlorophenyl)-3,3-dimethyl-4-oxoazetidin-1-yl]-1-adamantane carboxylate (160 mg, 0.370 mmol) in methanol (2 mL) was added with an aqueous solution of 4N-sodium hydroxide (1 mL, 4.00 mmol) at room temperature, and the resultant was stirred at the same temperature for 1.5 hours. The reaction solution was concentrated in vacuo, the obtained residue was dissolved in water, and washed with diethyl ether. The aqueous layer was adjusted to a liquid of pH 1 to 2 using 4N-hydrochloric acid, and extracted with chloroform. The organic layer was dried over anhydrous sodium sulfate, and concentrated in vacuo. The obtained residue was purified using preparative thin-layer chromatography (chloroform:methanol=10:1). trans-4-[2-(2,3-Dichlorophenyl)-3,3-dimethyl-4-oxoazetidin-1-yl]-1-adamantane carboxylic acid (156 mg, 100%) was obtained as a white amorphous solid.

$^1$H-NMR (400 MHz, CDCl$_3$) δ; 0.74 (s, 3H), 1.59 (s, 3H), 1.68-2.12 (m, 12H), 3.08 (s, 1H), 3.65 (s, 1H), 4.89 (s, 1H), 7.19 (d, J=7.6 Hz, 1H), 7.24-7.29 (m, 1H), 7.44 (d, J=7.8 Hz, 1H).

IR (ATR); 2930, 1731, 1696, 1425, 1218, 1080, 750 cm$^{-1}$.
EI-MS m/r; 422 (M$^+$+1).

Example 9

Preparation of trans-4-[2-(2,3-dichlorophenyl)-3,3-dimethyl-4-oxoazetidin-1-yl]-1-adamantane carboxyamide

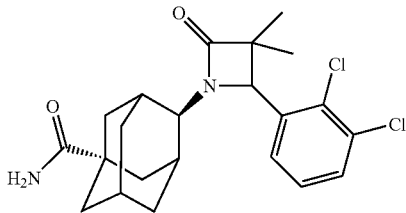

A solution of trans-4-[2-(2,3-dichlorophenyl)-3,3-dimethyl-4-oxoazetidin-1-yl]-1-adamantane carboxylic acid (145 mg, 0.343 mmol) in dichloromethane (3 mL) was added with WSC.HCl (132 mg, 0.686 mmol) and HOBT.H$_2$O (78.8 mg, 0.515 mmol) at room temperature. The resultant was stirred at the same temperature for 15 min, added with an aqueous solution of 30% ammonium (0.300 ml) and stirred further at the same temperature for 2 hours. The reaction solution was added with water, and extracted with chloroform. The organic layer was dried over anhydrous sodium sulfate, and concentrated in vacuo. The obtained residue was purified using preparative thin-layer chromatography (chloroform:methanol=10:1), and trans-4-[2-(2,3-dichlorophenyl)-3,3-dimethyl-4-oxoazetidin-1-yl]-1-adamantane carboxyamide (107 mg, 74.2%) was obtained as a white crystalline powder.

$^1$H-NMR (400 MHz, CDCl$_3$) δ; 0.75 (s, 3H), 1.59 (s, 3H), 1.68-2.14 (m, 12H), 3.10 (s, 1H), 3.67 (s, 1H), 4.88 (s, 1H), 5.20 (s, 1H), 5.55 (s, 1H), 7.19 (d, J=7.8 Hz, 1H), 7.25-7.30 (m, 1H) 7.44 (d, J=7.8 Hz, 1H).

IR (ATR); 3396, 2917, 1741, 1666, 1422, 1112, 777 cm$^{-1}$.
EI-MS m/z; 421 (M$^+$+1).

Example 10

Preparation of methyl trans-4-[2-(naphthalen-1-yl)-3,3-dimethyl-4-oxoazetidin-1-yl]-1-adamantane carboxylate

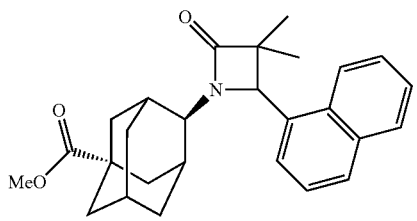

Methyl trans-4-adamantylamine-1-carboxylate was used in place of 2-adamantylamine, and 1-naphthaldehyde in place of benzaldehyde for a similar reaction and treatment as Example 1, and the title compound was obtained as a pale yellow oil.

$^1$H-NMR (400 MHz, CDCl$_3$) δ; 0.65 (s, 3H), 1.69 (s, 3H), 1.53-2.20 (m, 12H), 3.16 (s, 1H), 3.63 (s, 3H), 3.83 (s, 1H), 5.24 (s, 1H), 7.42 (d, J=7.3 Hz, 1H), 7.48-7.55 (m, 3H), 7.81 (d, J=8.3 Hz, 1H), 7.86-7.92 (m, 2H).

Example 11

Preparation of trans-4-[2-(naphthalen-1-yl)-3,3-dimethyl-4-oxoazetidin-1-yl]-1-adamantane carboxylic acid

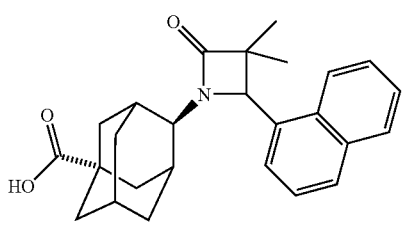

Methyl trans-4-[2-(naphthalen-1-yl)-3,3-dimethyl-4-oxoazetidin-1-yl]-1-adamantane carboxylate was used in place of methyl trans-4-[2-(2,3-dichlorophenyl)-3,3-dimethyl-4-oxoazetidin-1-yl]-1-adamantane carboxylate for a similar reaction and treatment as Example 8, and the title compound was obtained as a white amorphous solid.

$^1$H-NMR (400 MHz, CDCl$_3$) δ; 0.64 (s, 3H), 1.52-2.19 (m, 12H), 1.68 (s, 3H), 3.15 (s, 1H), 3.82 (s, 1H), 5.24 (s, 1H), 7.41 (d, J=6.8 Hz, 1H), 7.50-7.56 (m, 3H), 7.81 (d, J=8.3 Hz, 1H), 7.86-7.92 (m, 2H).

IR (ATR); 2926, 1729, 1696, 1452, 1220, 754 cm$^{-1}$.

FAB-MS m/z; 404 (M+H)$^+$.

Example 12

Preparation of trans-4-[2-(naphthalen-1-yl)-3,3-dimethyl-4-oxoazetidin-1-yl]1)-1-adamantane carboxyamide

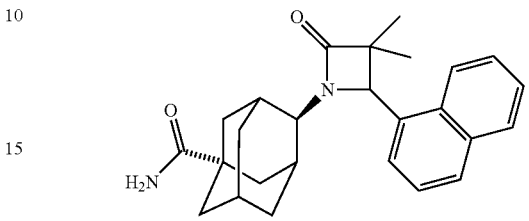

trans-4-[2-(Naphthalen-1-yl)-3,3-dimethyl-4-oxoazetidin-1-yl]-1-adamantane carboxylic acid was used in place of trans-4-[2-(2,3-dichlorophenyl)-3,3-dimethyl-4-oxoazetidin-1-yl]-1-adamantane carboxylic acid for a similar reaction and treatment as Example 9, and the title compound was obtained as a white amorphous solid.

$^1$H-NMR (400 MHz, CDCl$_3$) δ; 0.65 (s, 3H), 1.52-2.22 (m, 12H), 1.69 (s, 3H), 3.18 (s, 1H), 3.84 (s, 1H), 5.24 (s, 1H), 5.67 (s, 1H), 5.76 (s, 1H), 7.41 (d, J=7.1 Hz, 1H), 7.50-7.57 (m, 3H), 7.81 (d, J=8.0 Hz, 1H), 7.85-7.92 (m, 2H).

IR (ATR); 3348, 2925, 1735, 1664, 1365, 754 cm$^{-1}$.

FAB-MS m/z; 403 (M+H)$^+$.

Example 13

Preparation of methyl trans-4-[2-(benzo[d][1,3]dioxol-4-yl)-3,3-dimethyl-4-oxoazetidin-1-yl]-1-adamantane carboxylate

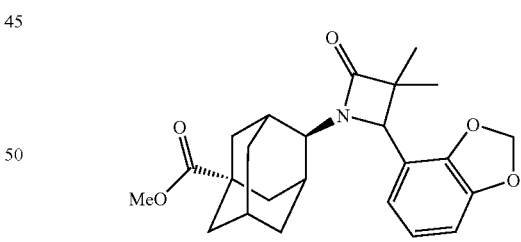

Methyl trans-4-adamantylamine-1-carboxylate was used in place of 2-adamantylamine, and 2,3-(methylenedioxy)benzaldehyde in place of benzaldehyde for a similar reaction and treatment as Example 1, and the title compound was obtained as a colorless amorphous solid.

$^1$H-NMR (400 MHz, CDCl$_3$) δ; 0.86 (s, 3H), 0.48 (s, 3H), 1.54-2.11 (m, 12H), 2.99 (s, 1H), 3.58 (s, 1H), 3.63 (s, 3H), 4.47 (s, 1H), 5.97 (d, J=6.4 Hz, 2H), 6.69 (d, J=7.7 Hz, 1H), 6.78 (d, J=7.7 Hz, 1H), 6.84 (t, J=7.7 Hz, 1H).

IR (ATR); 2929, 1730, 1459, 1250, 1238, 1079, 754 cm$^{-1}$.

EI-MS m/z; 411 (M$^+$).

Example 14

Preparation of trans-4-[2-(benzo[d][1,3]dioxol-4-yl)-3,3-dimethyl-4-oxoazetidin-1-yl]-1-adamantane carboxylic acid

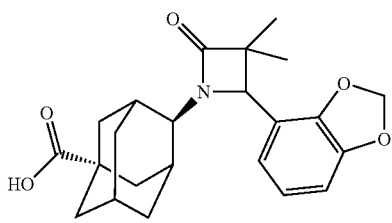

Methyl trans-4-[2-(benzo[d][1,3]dioxol-4-yl)-3,3-dimethyl-4-oxoazetidin-1-yl]-1-adamantane carboxylate was used in place of methyl trans-4-[2-(2,3-dichlorophenyl)-3,3-dimethyl-4-oxoazetidin-1-yl]-1-adamantane carboxylate for a similar reaction and treatment as Example 8, and the title compound was obtained as a colorless oil.

$^1$H-NMR (400 MHz, CDCl$_3$) δ; 0.86 (s, 3H), 1.48 (s, 3H), 1.53-2.11 (m, 12H), 2.99 (s, 1H), 3.58 (s, 1H), 4.48 (s, 1H), 5.96 (dd, J=1.2, 6.6 Hz, 2H), 6.68 (dd, J=1.2, 7.7 Hz, 1H), 6.78 (dd, J=1.3, 7.7 Hz, 1H), 6.84 (t, J=7.8 Hz, 1H).

IR (ATR); 2927, 1729, 1698, 1459, 1250, 754 cm$^{-1}$.

EI-MS m/z; 397 (M$^+$).

Example 15

Preparation of trans-4-[2-(benzo[d][1,3]dioxol-4-yl)-3,3-dimethyl-4-oxoazetidin-1-yl]-1-adamantane carboxyamide

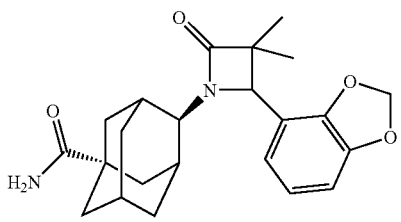

trans-4-[2-(Benzo[d][1,3]dioxol-4-yl)-3,3-dimethyl-4-oxoazetidin-1-yl]-1-adamantane carboxylic acid was used in place of trans-4-[2-(2,3-dichlorophenyl)-3,3-dimethyl-4-oxoazetidin-1-yl]-1-adamantane carboxylic acid for a similar reaction and treatment as Example 9, and the title compound was obtained as a white amorphous solid.

$^1$H-NMR (400 MHz, CDCl$_3$) δ; 0.87 (s, 3H), 1.48 (s, 3H), 1.55-2.13 (m, 12H), 3.02 (s, 1H), 3.59 (s, 1H), 4.47 (s, 1H), 5.63 (s, 2H), 5.97 (dd, J=1.4, 7.4 Hz, 2H), 6.68 (dd, J=1.1, 7.7 Hz, 1H), 6.79 (dd, J=1.4, 7.7 Hz, 1H), 6.84 (t, J=7.7 Hz, 1H).

IR (ATR); 3350, 2922, 1732, 1661, 1459, 1250, 1056, 754 cm$^{-1}$.

EI-MS m/z; 396 (M$^+$).

Example 16

Preparation of trans-4-[2-(isoquinolin-5-yl)-3,3-dimethyl-4-oxoazetidin-1-yl]-1-adamantane carboxyamide

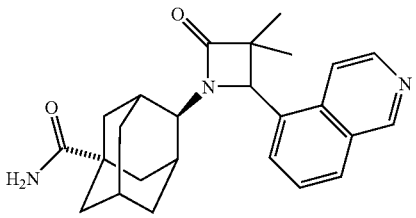

trans-4-[2-(Isoquinolin-5-yl)-3,3-dimethyl-4-oxoazetidin-1-yl]-1-adamantane carboxylic acid was used in place of trans-4-[2-(2,3-dichlorophenyl)-3,3-dimethyl-4-oxoazetidin-1-yl]-1-adamantane carboxylic acid for a similar reaction and treatment as Example 9, and the title compound was obtained as a colorless oil. trans-4-[2-(Isoquinolin-5-yl)-3,3-dimethyl-4-oxoazetidin-1-yl]-1-adamantane carboxylic acid was obtained by subjecting methyl trans-4-[2-(isoquinolin-5-yl)-3,3-dimethyl-4-oxoazetidin-1-yl]-1-adamantane carboxylate, obtained by using methyl trans-4-adamantylamine-1-carboxylate in place of 2-adamantylamine, and isoquinoline-5-carboxyaldehyde in place of benzaldehyde for a similar reaction and treatment as Example 1, to hydrolysis reaction.

$^1$H-NMR (400 MHz, CDCl$_3$) δ; 0.64 (s, 3H), 1.53-2.22 (m, 12H), 1.69 (s, 3H), 3.17 (s, 1H), 3.80 (s, 1H), 5.16 (s, 1H), 5.47 (s, 1H), 5.59 (s, 1H), 7.62-7.68 (m, 3H), 7.96 (d, J=7.3 Hz, 1H), 8.60 (d, J=5.8 Hz, 1H), 9.32 (s, 1H).

IR (ATR); 3344, 2923, 1738, 1663, 1385, 1112, 757 cm$^{-1}$.

EI-MS m/z; 403 (M$^+$).

Example 17

Preparation of trans-4-[2-(quinolin-5-yl)-3,3-dimethyl-4-oxoazetidin-1-yl]-1-adamantane carboxylic acid

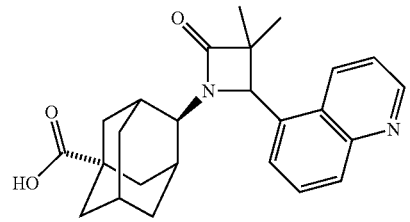

Methyl trans-4-[2-(quinolin-5-yl)-3,3-dimethyl-4-oxoazetidin-1-yl]-1-adamantane carboxylate was used in place of methyl trans-4-[2-(2,3-dichlorophenyl)-3,3-dimethyl-4-oxoazetidin-1-yl]-1-adamantane carboxylate for a similar reaction and treatment as Example 8, and the title compound was obtained as a colorless oil. Methyl trans-4-[2-(quinolin-5-yl)-3,3-dimethyl-4-oxoazetidin-1-yl]-1-adamantane carboxylate was obtained by using methyl trans-4-adamantylamine-1- carboxylate in place of 2-adamantylamine, and quinoline-5-carboxyaldehyde in place of benzaldehyde for a similar reaction and treatment as Example 1.

¹H-NMR (400 MHz, CDCl₃) δ; 0.63 (s, 3H), 1.55-2.19 (m, 12H), 1.67 (s, 3H), 3.16 (s, 1H), 3.82 (s, 1H), 5.18 (s, 1H), 7.48-7.51 (m, 2H), 7.77 (t, J=7.8 Hz, 1H), 8.11 (d, J=8.5 Hz, 1H), 8.25 (d, J=8.5 Hz, 1H), 8.99 (dd, J=1.5, 4.1 Hz, 1H).

EI-MS m/z; 404 (M⁺).

Example 18

Preparation of methyl trans-4-[2-(quinolin-8-yl)-3,3-dimethyl-4-oxoazetidin-1-yl]-1-adamantane carboxylate

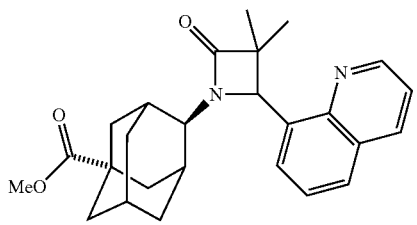

Methyl trans-4-adamantylamine-1-carboxylate was used in place of 2-adamantylamine, and quinoline-8-carboxyaldehyde in place of benzaldehyde for a similar reaction and treatment as Example 1, and the title compound was obtained as a pale yellow amorphous solid.

¹H-NMR (400 MHz, CDCl₃) δ; 0.58 (s, 3H), 1.51-2.06 (m, 11H), 1.67 (s, 3H), 2.18-2.23 (m, 1H), 3.14 (s, 1H), 3.63 (s, 3H), 3.81 (s, 1H), 5.81 (s, 1H), 7.45 (dd, J=4.1, 8.3 Hz, 1H), 7.54-7.60 (m, 2H), 7.77 (dd, J=1.8, 7.7 Hz, 1H), 8.18 (dd, J=1.8, 8.3 Hz, 1H), 8.91 (dd, J=1.8, 4.1 Hz, 1H).

Example 19

Preparation of trans-4-[2-(quinolin-8-yl)-3,3-dimethyl-4-oxoazetidin-1-yl]-1-adamantane carboxylic acid

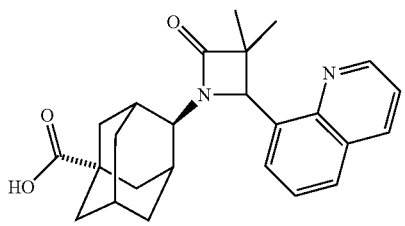

Methyl trans-4-[2-(quinolin-8-yl)-3,3-dimethyl-4-oxoazetidin-1-yl]-1-adamantane carboxylate was used in place of methyl trans-4-[2-(2,3-dichlorophenyl)-3,3-dimethyl-4-oxoazetidin-1-yl]-1-adamantane carboxylate for a similar reaction and treatment as Example 8, and the title compound was obtained as a pale yellow amorphous solid.

¹H-NMR (400 MHz, CDCl₃) δ; 0.58 (s, 3H), 1.48-2.22 (m, 12H), 1.66 (s, 3H), 3.14 (s, 1H), 3.90 (s, 1H), 5.82 (s, 1H), 7.44 (dd, J=4.2, 8.3 Hz, 1H), 7.55-7.61 (m, 2H), 7.77 (dd, J=1.8, 7.7 Hz, 1H), 8.18 (dd, j=1.7, 8.3 Hz, 1H), 8.92 (dd, J=1.7, 4.1 Hz, 1H).

Example 20

Preparation of trans-4-[2-(quinolin-8-yl)-3,3-dimethyl-4-oxoazetidin-1-yl]-1-adamantane carboxyamide

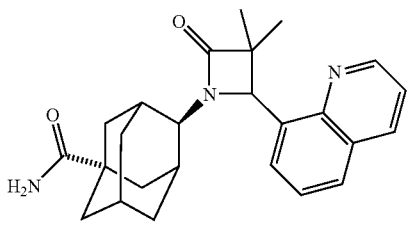

trans-4-[2-(Quinolin-8-yl)-3,3-dimethyl-4-oxoazetidin-1-yl]-1-adamantane carboxylic acid was used in place of trans-4-[2-(2,3-dichlorophenyl)-3,3-dimethyl-4-oxoazetidin-1-yl]-1-adamantane carboxylic acid for a similar reaction and treatment as Example 9, and the title compound was obtained as a white amorphous solid.

¹H-NMR (400 MHz, CDCl₃) δ; 0.58 (s, 3H), 1.51-2.25 (m, 12H), 1.67 (s, 3H), 3.17 (s, 1H), 3.82 (s, 1H), 5.57 (s, 1H), 5.62 (s, 1H), 5.82 (s, 1H), 7.44 (dd, J=4.2, 8.3 Hz, 1H), 7.54-7.60 (m, 2H), 7.77 (dd, J=1.9, 7.6 Hz, 1H), 8.18 (dd, J=1.7, 8.3 Hz, 1H), 8.91 (dd, J=1.8, 4.3 Hz, 1H).

IR (ATR); 3352, 2925, 1726, 1665, 1498, 1363, 1112, 751 cm⁻¹.

EI-MS m/z; 403 (M⁺).

Example 21

Preparation of 1-(adamantan-2-yl)-3,3-dimethyl-4-(2,3-dimethoxyphenyl)azetidin-2-one

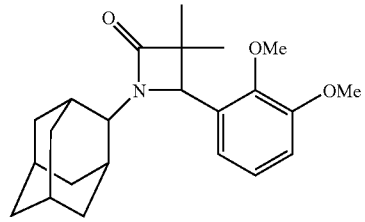

2,3-Dimethoxybenzaldehyde was used in place of benzaldehyde for a similar reaction and treatment as Example 1, and the title compound was obtained as a colorless oil.

¹H-NMR (400 MHz, CDCl₃) δ; 0.76 (s, 3H), 1.50 (s, 3H), 1.53-1.88 (m, 12H), 2.11 (d, J=12.9 Hz, 1H), 2.90 (s, 1H), 3.63 (s, 1H), 3.82 (s, 3H), 3.88 (s, 3H), 4.83 (s, 1H), 6.82 (d, J=7.8 Hz, 1H), 6.86 (d, J=8.3 Hz, 1H), 7.07 (t, J=8.0 Hz, 1H).

IR (ATR); 2906, 2853, 1742, 1480, 750 cm⁻¹.

EI-MS m/z; 369 (M⁺).

Example 22

Preparation of 1-(adamantan-2-yl)-3,3-dimethyl-4-(4-chlorophenyl)azetidin-2-one

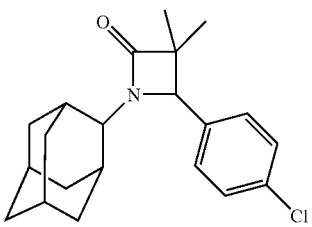

4-Chlorobenzaldehyde was used in place of benzaldehyde for a similar reaction and treatment as Example 1, and the title compound was obtained as a white amorphous solid.

$^1$H-NMR (400 MHz, CDCl$_3$) δ; 0.73 (s, 3H), 1.46 (s, 3H), 1.49-1.88 (m, 12H), 2.09 (d, J=12.7 Hz, 1H), 2.58 (s, 1H), 3.58 (s, 1H), 4.36 (s, 1H), 7.16 (d, J=8.3 Hz, 2H), 7.35 (d, J=8.6 Hz, 2H).

IR (ATR); 2900, 2855, 1727 cm$^{-1}$.

EI-MS m/z; 343 (M$^+$).

Example 23

Preparation of 1-(adamantan-2-yl)-3,3-dimethyl-4-(4-methoxyphenyl)azetidin-2-one

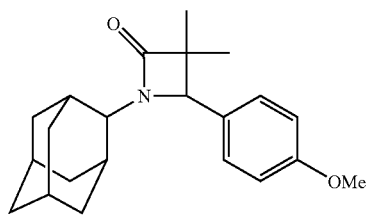

4-Methoxybenzaldehyde was used in place of benzaldehyde for a similar reaction and treatment as Example 1, and the title compound was obtained as a white amorphous solid.

$^1$H-NMR (400 MHz, CDCl$_3$) δ; 0.73 (d, J=1.7 Hz, 3H), 1.44 (d, J=1.5 Hz, 3H), 1.51-1.88 (m, 12H), 2.11 (d, J=12.9 Hz, 1H), 2.87 (s, 1H), 3.59 (s, 1H), 3.82 (s, 3H), 4.33 (s, 1H), 6.90 (d, J=8.6 Hz, 2H), 7.13 (d, J=8.3 Hz, 2H).

IR (ATR); 2907, 2855, 1729, 1246 cm$^1$.

EI-MS m/z; 339 (M$^+$).

Example 24

Preparation of 1-(adamantan-2-yl)-3,3-dimethyl-4-(2,3-difluorophenyl)azetidin-2-one

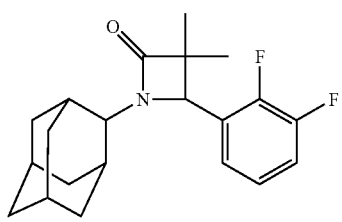

2,3-Difluorobenzaldehyde was used in place of benzaldehyde for a similar reaction and treatment as Example 1, and the title compound was obtained as a white amorphous solid.

$^1$H-NMR (400 MHz, CDCl$_3$) δ; 0.78 (s, 3H), 1.52 (s, 3H), 1.54-1.89 (m, 12H), 2.10 (d, J=13.2 Hz, 1H), 2.90 (s, 1H), 3.63 (s, 1H), 4.73 (s, 1H), 7.01-7.04 (m, 1H), 7.09-7.14 (m, 2H).

IR (ATR); 2924, 2854, 1743, 1485 cm$^{-1}$.

EI-MS m/z; 345 (M$^+$).

Example 25

Preparation of 1-(adamantan-2-yl)-3,3-dimethyl-4-(3-chloro-2-fluorophenyl)azetidin-2-one

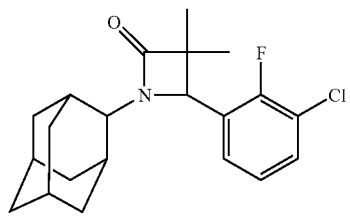

3-Chloro-2-fluorobenzaldehyde was used in place of benzaldehyde for a similar reaction and treatment as Example 1, and the title compound was obtained as a colorless oil.

$^1$H-NMR (400 MHz, CDCl$_3$) δ; 0.77 (s, 3H), 1.51 (s, 3H), 1.56-1.90 (m, 12H), 2.09 (d, J=13.2 Hz, 1H), 2.91 (s, 1H), 3.63 (s, 1H), 4.73 (s, 1H), 7.13-7.17 (m, 2H), 7.33-7.36 (m, 1H).

IR (ATR); 2907, 2854, 1748, 1457 cm$^{-1}$.

EI-MS m/z; 361 (M$^+$).

Example 26

Preparation of 1-(adamantan-2-yl)-3,3-dimethyl-4-(3,4-dichlorophenyl)azetidin-2-one

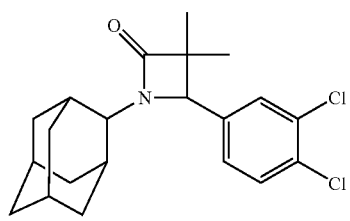

3,4-Dichlorobenzaldehyde was used in place of benzaldehyde for a similar reaction and treatment as Example 1, and the title compound was obtained as a white amorphous solid.

$^1$H-NMR (400 MHz, CDCl$_3$) δ; 0.75 (s, 3H), 1.47 (s, 3H), 1.54-1.89 (m, 12H), 2.07 (d, J=13.2 Hz, 1H), 2.86 (s, 1H), 3.56 (s, 1H), 4.32 (s, 1H), 7.07 (dd, J=2.2, 8.3 Hz, 1H), 7.31 (d, J=2.2 Hz, 1H), 7.46 (d, J=8.3 Hz, 1H).

IR (ATR); 2924, 2852, 1735 cm$^{-1}$.

EI-MS m/z; 378 (M$^+$).

Example 27

Preparation of 1-(adamantan-2-yl)-3,3-dimethyl-4-(3,4-difluorophenyl)azetidin-2-one

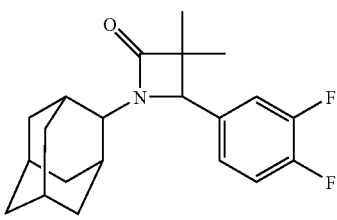

3,4-Difluorobenzaldehyde was used in place of benzaldehyde for a similar reaction and treatment as Example 1, and the title compound was obtained as a white amorphous solid.

$^1$H-NMR (400 MHz, CDCl$_3$) δ; 0.74 (s, 3H) 1.46 (s, 3H), 1.54-1.88 (m, 12H), 2.08 (d, J=13.2 Hz, 1H), 2.86 (s, 1H), 3.57 (s, 1H), 4.33 (s, 1H), 6.94-6.96 (m, 1H), 7.01-7.06 (m, 1H), 7.15-7.21 (m, 1H).

IR (ATR); 2925, 2859, 1725, 1516, 1291 cm$^{-1}$.
EI-MS m/z; 345 (M$^+$).

Example 28

Preparation of 1-(adamantan-2-yl)-3,3-dimethyl-4-(2-fluoro-3-trifluoromethylphenyl)azetidin-2-one

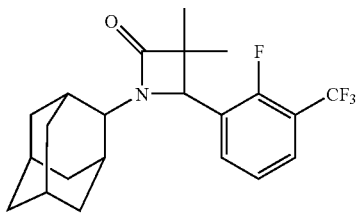

2-Fluoro-3-trifluoromethyl benzaldehyde was used in place of benzaldehyde for a similar reaction and treatment as Example 1, and the title compound was obtained as a white amorphous solid.

$^1$H-NMR (400 MHz, CDCl$_3$) δ; 0.76 (s, 3H), 1.53 (s, 3H), 1.57-1.91 (m, 12H), 2.10 (d, J=13.4 Hz, 1H), 2.92 (s, 1H), 3.64 (s, 1H), 4.77 (s, 1H), 7.30 (t, J=7.6 Hz, 1H), 7.49 (t, J=6.6 Hz, 1H), 7.57 (t, J=6.8 Hz, 1H).

IR (ATR); 2916, 2859, 1738, 1332, 1125 cm$^{-1}$.
EI-MS m/z; 395 (M$^+$).

Example 29

Preparation of 1-(adamantan-2-yl)-3,3-dimethyl-4-(3-chloro-4-fluorophenyl)azetidin-2-one

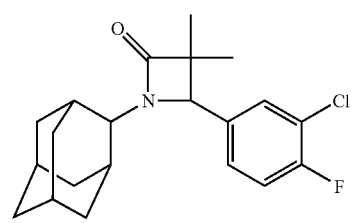

3-Chloro-4-fluorobenzaldehyde was used in place of benzaldehyde for a similar reaction and treatment as Example 1, and the title compound was obtained as a white amorphous solid.

$^1$H-NMR (400 MHz, CDCl$_3$) δ; 0.75 (s, 3H), 1.46 (s, 3H), 1.54-1.89 (m, 12H), 2.08 (d, J=13.2 Hz, 1H), 2.86 (s, 1H), 3.56 (s, 1H), 4.33 (s, 1H), 7.08-7.12 (m, 1H), 7.17 (t, J=8.6 Hz, 1H), 7.25-7.27 (m, 1H).

IR (ATR); 2917, 2854, 1728, 1499 cm$^{-1}$.
EI-MS m/z; 361 (M$^+$).

Example 30

Preparation of 1-(adamantan-2-yl)-3,3-dimethyl-4-(2-chloro-3-trifluoromethylphenyl)azetidin-2-one

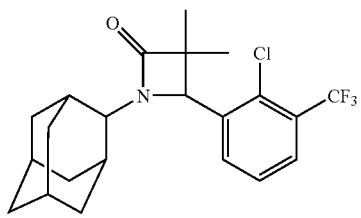

2-Chloro-3-trifluoromethyl benzaldehyde was used in place of benzaldehyde for a similar reaction and treatment as Example 1, and the title compound was obtained as a white amorphous solid.

$^1$H-NMR (400 MHz, CDCl$_3$) δ; 0.72 (s, 3H), 1.60 (s, 3H), 1.65-1.92 (m, 12H), 2.11 (d, J=12.9 Hz, 1H), 2.95 (s, 1H), 3.67 (s, 1H), 4.96 (s, 1H), 7.44 (t, J=7.6 Hz, 1H), 7.50 (d, J=6.3 Hz, 1H), 7.67 (d, J=7.8 Hz, 1H).

IR (ATR); 2920, 2879, 1745, 1319, 1140, 1133 cm$^{-1}$.
EI-MS m/z; 411 (M$^+$).

Example 31

Preparation of 1-(adamantan-2-yl)-3,3-dimethyl-4-(3,5-dichlorophenyl)azetidin-2-one

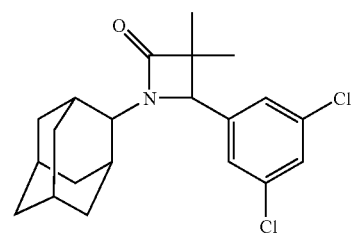

3,5-Dichlorobenzaldehyde was used in place of benzaldehyde for a similar reaction and treatment as Example 1, and the title compound was obtained as a white amorphous solid.

$^1$H-NMR (400 MHz, CDCl$_3$) δ; 0.77 (s, 3H), 1.47 (s, 3H), 1.60-1.89 (m, 12H), 2.06 (d, J=12.9 Hz, 1H), 2.87 (s, 1H), 3.57 (s, 1H), 4.31 (s, 1H), 7.11 (d, J=1.7 Hz, 2H), 7.32 (t, J=2.0 Hz, 1H).

IR (ATR); 2921, 2852, 1733 cm$^{-1}$.
FAB-MS ink; 378 (M+H)$^+$.

Example 32

Preparation of 1-(adamantan-2-yl)-3,3-dimethyl-4-(4-fluoro-3-trifluoromethylphenyl)azetidin-2-one

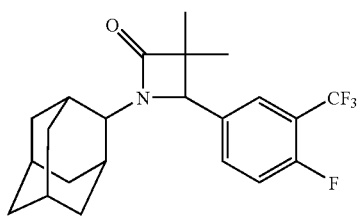

4-Fluoro-3-trifluoromethyl benzaldehyde was used in place of benzaldehyde for a similar reaction and treatment as Example 1, and the title compound was obtained as a white amorphous solid.

$^1$H-NMR (400 MHz, CDCl$_3$) δ; 0.73 (s, 3H), 1.48 (s, 3H), 1.51-1.89 (m, 12H), 2.07 (d, J=15.7 Hz, 1H), 2.86 (s, 1H), 3.54 (s, 1H), 4.40 (s, 1H), 7.20-7.27 (m, 1H), 7.40-7.44 (m, 2H).

IR (ATR); 2903, 2859, 1738, 1328, 1142 cm$^{-1}$.
FAB-MS m/z; 396 (M+H)$^+$.

Example 33

Preparation of 1-(adamantan-2-yl)-3,3-dimethyl-4-(2-methoxyphenyl)azetidin-2-one

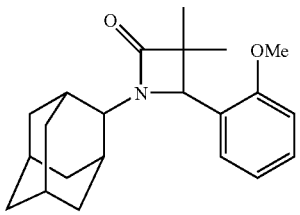

2-Methoxybenzaldehyde was used in place of benzaldehyde for a similar reaction and treatment as Example 1, and the title compound was obtained as a white amorphous solid.

$^1$H-NMR (400 MHz, CDCl$_3$) δ; 0.68 (s, 3H), 1.49 (s, 3H), 1.57-1.90 (m, 12H), 2.13 (d, 12.9 Hz, 1H), 2.95 (s, 1H), 3.72 (s, 1H), 3.83 (s, 3H), 4.79 (s, 1H), 6.89 (d, J=8.0 Hz, 1H), 6.97 (t, J=6.8 Hz, 1H), 7.18 (dd, J=1.4, 7.6 Hz, 1H), 7.24-7.28 (m, 1H).

IR (ATR); 2905, 2851, 1742, 1242, 760 cm$^{-1}$.
FAB-MS m/z; 340 (M+H)$^+$.

Example 34

Preparation of 1-(adamantan-2-yl)-3,3-dimethyl-4-(3-methoxyphenyl)azetidin-2-one

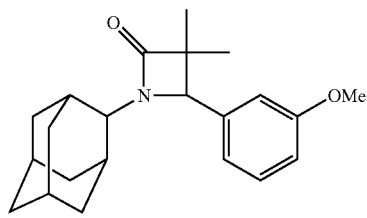

3-Methoxybenzaldehyde was used in place of benzaldehyde for a similar reaction and treatment as Example 1, and the title compound was obtained as a white amorphous solid.

$^1$H-NMR (400 MHz, CDCl$_3$) δ; 0.75 (s, 3H), 1.46 (s, 3H), 1.54-1.87 (m, 12H), 2.10 (d, J=12.9 Hz, 1H), 2.89 (s, 1H), 3.63 (s, 1H), 3.82 (s, 3H), 4.35 (s, 1H), 6.73-6.74 (m, 1H), 6.80 (d, J=7.6 Hz, 1H), 6.83-6.85 (m, 1H), 7.30 (d, J=8.1 Hz, 1H).

IR (ATR); 2908, 2854, 1731, 1049 cm$^{-1}$.
FAB-MS m/z; 340 (M+H)$^+$.

Example 35

Preparation of 1-(adamantan-2-yl)-3,3-dimethyl-4-(2,3,5-trifluorophenyl)azetidin-2-one

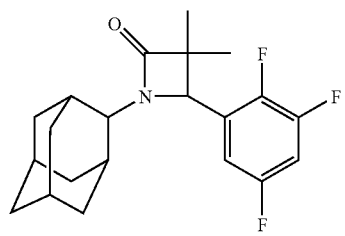

2,3,5-Trifluorobenzaldehyde was used in place of benzaldehyde for a similar reaction and treatment as Example 1, and the title compound was obtained as a white amorphous solid.

$^1$H-NMR (400 MHz, CDCl$_3$) δ; 0.81 (s, 3H), 1.51 (s, 3H), 1.65-1.91 (m, 12H), 2.07 (d, J=13.2 Hz, 1H), 2.90 (s, 1H), 3.61 (s, 1H), 4.71 (s, 1H), 6.76-6.80 (m, 1H), 6.85-6.92 (m, 2H).

IR (ATR); 2916, 2855, 1736, 1499 cm$^{-1}$.
FAB-MS m/z; 364 (M+H)$^+$.

Example 36

Preparation of 1-(adamantan-2-yl)-3,3-dimethyl-4-(3,4,5-trifluorophenyl)azetidin-2-one

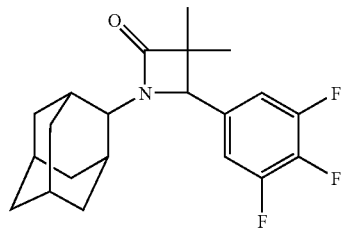

3,4,5-Trifluorobenzaldehyde was used in place of benzaldehyde for a similar reaction and treatment as Example 1, and the title compound was obtained as a white amorphous solid.

$^1$H-NMR (400 MHz, CDCl$_3$) δ; 0.78 (s, 3H), 1.46 (s, 3H), 1.56-1.90 (m, 12H), 2.06 (d, J=12.0 Hz, 1H), 2.86 (s, 1H), 3.57 (s, 1H), 4.30 (s, 1H), 6.86 (dd, J=6.4, 8.1 Hz, 2H).

IR (ATR); 2913, 2850, 1733, 1527, 1038 cm$^{-1}$.
FAB-MS m/z; 364 (M+H)$^+$.

Example 37

Preparation of 1-(adamantan-2-yl)-3,3-dimethyl-4-(4-isopropylphenyl)azetidin-2-one

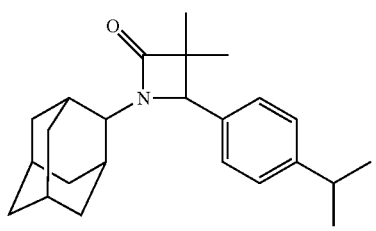

4-Isopropylbenzaldehyde was used in place of benzaldehyde for a similar reaction and treatment as Example 1, and the title compound was obtained as a white amorphous solid.

$^1$H-NMR (400 MHz, CDCl$_3$) δ; 0.72 (s, 3H), 1.24 (d, J=2.4 Hz, 6H), 1.45 (s, 3H), 1.55-1.88 (m, 12H), 2.12 (d, J=13.2 Hz, 1H), 2.89-2.94 (m, 2H), 3.61 (s, 1H), 4.35 (s, 1H), 7.11 (d, J=8.3 Hz, 2H), 7.21 (d, J=8.0 Hz, 2H).

IR (ATR); 2959, 2908, 2851, 1732 cm$^{-1}$.

FAB-MS m/z; 352 (M+H)$^+$.

Example 38

Preparation of 1-(adamantan-2-yl)-3,3-dimethyl-4-(4-t-butylphenyl)azetidin-2-one

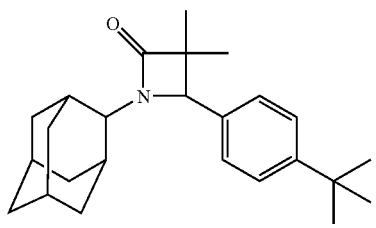

4-t-Butylbenzaldehyde was used in place of benzaldehyde for a similar reaction and treatment as Example 1, and the title compound was obtained as a white amorphous solid.

$^1$H-NMR (400 MHz, CDCl$_3$) δ; 0.72 (s, 3H), 1.32 (s, 9H), 1.45 (s, 3H), 1.55-1.88 (m, 12H), 2.12 (d, J=13.2 Hz, 1H), 2.89 (s, 1H), 3.61 (s, 1H), 4.35 (s, 1H), 7.11 (d, J=8.3 Hz, 2H), 7.36 (d, 8.3 Hz, 2H).

IR (ATR); 2959, 2903, 2853, 1731 cm$^{-1}$.

FAB-MS m/z; 366 (M+H)$^+$.

Example 39

Preparation of 1-(adamantan-2-yl)-3,3-dimethyl-4-(2-fluorophenyl)azetidin-2-one

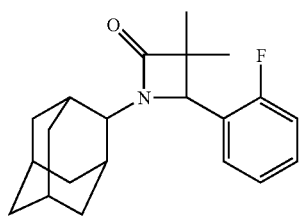

2-Fluorobenzaldehyde was used in place of benzaldehyde for a similar reaction and treatment as Example 1, and the title compound was obtained as a pale yellow oil.

$^1$H-NMR (400 MHz, CDCl$_3$) δ; 0.76 (s, 3H), 1.50 (s, 3H), 1.56-1.89 (m, 12H), 2.11 (d, J=12.9 Hz, 1H), 2.92 (s, 1H), 3.66 (s, 1H), 4.74 (s, 1H), 7.05-7.10 (m, 1H), 7.15-7.19 (m, 1H), 7.25-7.31 (m, 2H).

IR (ATR); 2906, 2854, 1731, 1488, 1233, 757 cm$^{-1}$.

EI-MS m/z; 327 (M$^+$).

Example 40

Preparation of 1-(adamantan-2-yl)-3,3-dimethyl-4-(2-fluoro-4-methoxyphenyl)azetidin-2-one

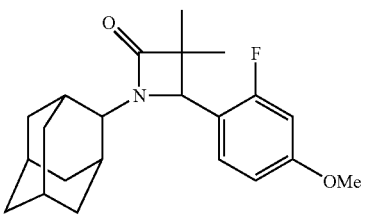

2-Fluoro-4-methoxy benzaldehyde was used in place of benzaldehyde for a similar reaction and treatment as Example 1, and the title compound was obtained as a colorless oil.

$^1$H-NMR (400 MHz, CDCl$_3$) δ; 0.77 (s, 3H), 1.47 (s, 3H), 1.55-1.88 (m, 12H), 2.10 (d, J=13.2 Hz, 1H), 2.89 (s, 1H), 3.61 (s, 1H), 3.81 (s, 3H), 4.65 (s, 1H), 6.64 (dd, J=2.4, 12.2 Hz, 1H), 6.72 (dd, J=2.4, 8.5 Hz, 1H), 7.15 (t, J=8.6 Hz, 1H).

IR (ATR); 2907, 2853, 1746, 1625, 1508, 1114 cm$^{-1}$.

EI-MS m/z; 357 (M$^+$).

Example 41

Preparation of 1-(adamantan-2-yl)-3,3-dimethyl-4-(2-trifluoromethylphenyl)azetidin-2-one

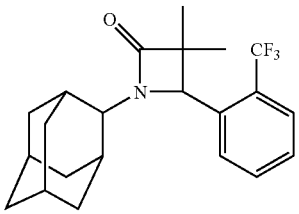

2-Trifluoromethyl benzaldehyde was used in place of benzaldehyde for a similar reaction and treatment as Example 1, and the title compound was obtained as a white amorphous solid.

$^1$H-NMR (400 MHz, CDCl$_3$) δ; 0.69 (s, 3H), 1.49 (s, 3H), 1.53-1.90 (m, 12H), 2.10 (d, J=13.2 Hz, 1H), 2.93 (s, 1H), 3.58 (s, 1H), 4.83 (s, 1H), 7.43 (t, J=7.6 Hz, 1H), 7.48 (d, J=7.8 Hz, 1H), 7.61 (d, J=7.3 Hz, 1H), 7.70 (d, J=7.8 Hz, 1H).

IR (ATR); 2906, 1731, 1313, 1115, 774 cm$^{-1}$.

EI-MS m/z; 377 (M$^+$).

Example 42

Preparation of 1-(adamantan-2-yl)-3,3-dimethyl-4-(4-trifluoromethoxyphenyl)azetidin-2-one

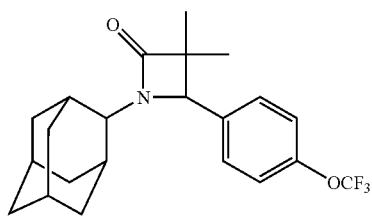

4-Trifluoromethoxy benzaldehyde was used in place of benzaldehyde for a similar reaction and treatment as Example 1, and the title compound was obtained as a white amorphous solid.

$^1$H-NMR (400 MHz, CDCl$_3$) δ; 0.72 (s, 3H), 1.47 (s, 3H), 1.54-1.89 (m, 12H), 2.10 (d, J=13.2 Hz, 1H), 2.88 (s, 1H), 3.59 (s, 1H), 4.39 (s, 1H), 7.24 (s, 41-1).

IR (ATR); 2906, 2859, 1731, 1298, 1263, 1163 cm$^{-1}$.

EI-MS m/z; 393 (M$^+$).

Example 43

Preparation of 1-(adamantan-2-yl)-3,3-dimethyl-4-(4-bromophenyl)azetidin-2-one

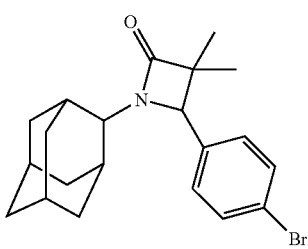

4-Bromobenzaldehyde was used in place of benzaldehyde for a similar reaction and treatment as Example 1, and the title compound was obtained as a white amorphous solid.

$^1$H-NMR (400 MHz, CDCl$_3$) δ; 0.79 (s, 3H), 1.46 (s, 3H), 1.51-2.10 (m, 13H), 2.87 (s, 1H), 3.58 (s, 1H), 4.34 (s, 1H), 7.09 (d, J=8.3 Hz, 2H), 7.50 (d, J=8.3 Hz, 2H).

IR (ATR); 2906, 1743, 1010, 753 cm$^{-1}$.

EI-MS m/z; 388 (M$^+$).

Example 44

Preparation of 1-(adamantan-2-yl)-3,3-dimethyl-4-(2-chlorophenyl)azetidin-2-one

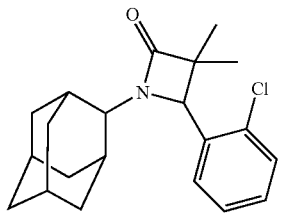

2-Chlorobenzaldehyde was used in place of benzaldehyde for a similar reaction and treatment as Example 1, and the title compound was obtained as a white amorphous solid.

$^1$H-NMR (400 MHz, CDCl$_3$) δ; 0.72 (s, 3H), 1.57 (s, 3H), 1.60-2.00 (m, 12H), 2.09-2.13 (m, 1H), 2.94 (s, 1H), 3.69 (s, 1H), 4.91 (s, 1H), 7.22-7.33 (m, 3H), 7.39 (d, J=7.6 Hz, 1H).

IR (ATR); 2911, 1753, 1736, 761 cm$^{-1}$.

EI-MS m/z; 344 (M$^+$).

Example 45

Preparation of 1-(adamantan-2-yl)-3,3-dimethyl-4-(naphthalen-1-yl)azetidin-2-one

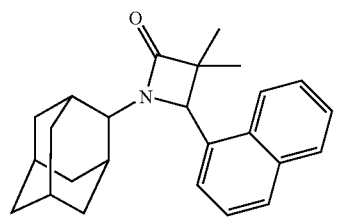

1-Naphthaldehyde was used in place of benzaldehyde for a similar reaction and treatment as Example 1, and the title compound was obtained as a white amorphous solid.

$^1$H-NMR (400 MHz, CDCl$_3$) δ; 0.63 (s, 3H), 1.56-1.91 (m, 15H), 2.16-2.19 (m, 1H), 3.04 (s, 1H), 3.84 (s, 1H), 5.24 (s, 1H), 7.44 (d, J=6.8 Hz, 1H), 7.49-7.58 (m, 3H), 7.80 (d, J=8.1 Hz, 1H), 7.85-7.92 (m, 2H).

IR (ATR); 2907, 1741, 753 cm$^{-1}$.

EI-MS m/z; 359 (M$^+$).

Example 46

Preparation of trans-1-(5-hydroxyadamantan-2-yl)-3,3-dimethyl-4-(2,3-dichlorophenyl)azetidin-2-one

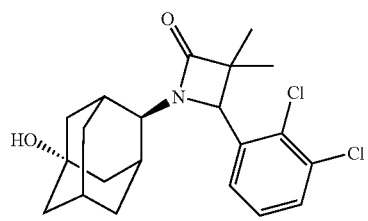

trans-5-Hydroxy-2-adamantylamine was used in place of 2-adamantylamine, and 2,3-dichlorobenzaldehyde in place of benzaldehyde for a similar reaction and treatment as Example 1, and the title compound was obtained as a white amorphous solid.

$^1$H-NMR (400 MHz, CDCl$_3$) δ; 0.74 (s, 3H), 1.48-1.83 (m, 14H), 1.99-2.05 (m, 1H), 2.20 (s, 1H), 3.14 (s, 1H), 3.69 (s, 1H), 4.89 (s, 1H), 7.19 (dd, J=1.5, 7.8 Hz, 1H), 7.28 (t, J=7.8 Hz, 1H), 7.43 (dd, J=1.5, 7.8 Hz, 1H).

IR (ATR); 3431, 2927, 1730, 1424, 1120, 778 cm$^{-1}$.

EI-MS m/z; 394 (M$^+$).

Example 47

Preparation of trans-1-(5-hydroxyadamantan-2-yl)-3,3-dimethyl-4-(naphthalen-1-yl)azetidin-2-one

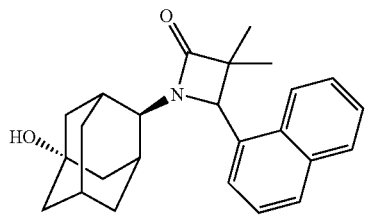

trans-5-Hydroxy-2-adamantylamine was used in place of 2-adamantylamine, and 1-naphthaldehyde in place of benzaldehyde for a similar reaction and treatment as Example 1, and the title compound was obtained as a white amorphous solid.

$^1$H-NMR (400 MHz, CDCl$_3$) δ; 0.64 (s, 3H), 1.44-1.87 (m, 14H), 2.09-2.12 (m, 1H), 2.20 (s, 1H), 3.24 (s, 1H), 3.77 (s, 1H), 5.24 (s, 1H), 7.41 (d, J=7.1 Hz, 1H), 7.49-7.58 (m, 3H), 7.81 (d, J=8.0 Hz, 1H), 7.86-7.92 (m, 2H).

IR (ATR); 3411, 2922, 1728, 1352, 1112, 779 cm$^{-1}$.

EI-MS m/z; 375 (M$^+$).

Example 48

Preparation of trans-1-(5-hydroxyadamantan-2-yl)-3,3-dimethyl-4-(4-methoxynaphthalen-1-yl)azetidin-2-one

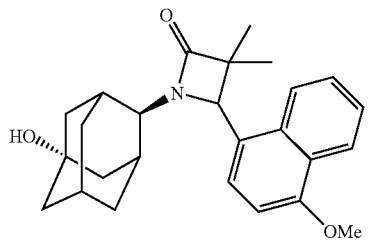

trans-5-Hydroxy-2-adamantylamine was used in place of 2-adamantylamine, and 4-methoxy-1-naphthaldehyde in place of benzaldehyde for a similar reaction and treatment as Example 1, and the title compound was obtained as a white amorphous solid.

$^1$H-NMR (400 MHz, CDCl$_3$) δ; 0.70 (s, 3H), 1.56-1.90 (m, 14H), 2.07-2.10 (m, 1H), 2.19 (s, 1H), 3.23 (s, 1H), 3.78 (s, 1H), 4.05 (s, 3H), 5.18 (s, 1H), 6.84 (d, J=8.1 Hz, 1H), 7.30 (d, J=8.1 Hz, 1H), 7.52-7.57 (m, 2H), 7.78 (d, J=8.1 Hz, 1H), 8.35 (d, J=8.1 Hz, 1H).

IR (ATR); 3404, 2923, 1724, 1275, 1092, 763 cm$^{-1}$.

EI-MS m/z; 405 (M$^+$).

Example 49

Preparation of methyl trans-4-[2-(quinolin-4-yl)-3,3-dimethyl-4-oxoazetidin-1-yl]-1-adamantane carboxylate

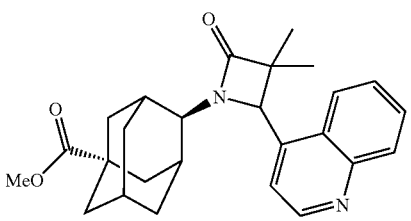

Methyl trans-4-adamantylamine-1-carboxylate was used in place of 2-adamantylamine, and quinoline-4-carboxyaldehyde in place of benzaldehyde for a similar reaction and treatment as Example 1, and the title compound was obtained as a white amorphous solid.

$^1$H-NMR (400 MHz, CDCl$_3$) δ; 0.67 (s, 3H), 1.50-2.17 (m, 15H), 3.15 (s, 1H), 3.64 (s, 3H), 3.82 (s, 1H), 5.20 (s, 1H), 7.32 (d, J=4.4 Hz, 1H), 7.64 (t, J=8.1 Hz, 1H), 7.78 (t, J=8.1 Hz, 1H), 7.86 (d, J=8.1 Hz, 1H), 8.19 (d, J=8.1 Hz, 1H), 8.95 (d, J=4.4 Hz, 1H).

IR (ATR); 1906, 1743, 1236, 1080, 758 cm$^{-1}$.

FAB-MS m/z; 419 (M+H)$^+$.

Example 50

Preparation of trans-4-[2-(quinolin-4-yl)-3,3-dimethyl-4-oxoazetidin-1-yl]-1-adamantane carboxylic acid

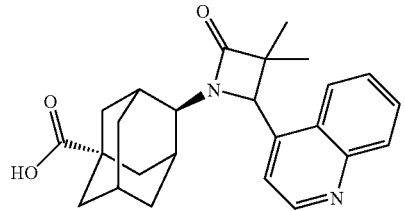

Methyl trans-4-[2-(quinolin-4-yl)-3,3-dimethyl-4-oxoazetidin-1-yl]-1-adamantane carboxylate was used in place of methyl trans-4-[2-(2,3-dichlorophenyl)-3,3-dimethyl-4-oxoazetidin-1-yl]-1-adamantane carboxylate for a similar reaction and treatment as Example 8, and the title compound was obtained as a white amorphous solid.

$^1$H-NMR (400 MHz, CDCl$_3$) δ; 0.67 (s, 3H), 1.56-1.60 (m, 1H), 1.71 (s, 3H), 1.79-2.16 (m, 11H), 3.15 (s, 1H), 3.82 (s, 1H), 5.21 (s, 1H), 7.36 (d, J=4.4 Hz, 1H), 7.64 (t, J=8.1 Hz, 1H), 7.79 (t, J=8.1 Hz, 1H), 7.87 (d, J=8.1 Hz, 1H), 8.22 (d, J=8.1 Hz, 1H), 8.97 (d, J=4.4 Hz, 1H).

IR (ATR); 2926, 1722, 1698, 1218, 1080, 761 cm$^{-1}$.

FAB-MS m/z; 405 (M+H)$^+$.

Example 51

Preparation of trans-4-[2-(quinolin-4-yl)-3,3-dimethyl-4-oxoazetidin-1-yl]-1-adamantane carboxyamide

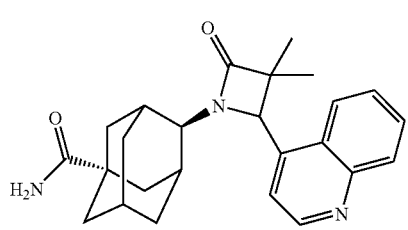

trans-4-[2-(Quinolin-4-yl)-3,3-dimethyl-4-oxoazetidin-1-yl]-1-adamantane carboxylic acid was used in place of trans-4-[2-(2,3-dichlorophenyl)-3,3-dimethyl-4-oxoazetidin-1-yl]-1-adamantane carboxylic acid for a similar reaction and treatment as Example 9, and the title compound was obtained as a white amorphous solid.

$^1$H-NMR (400 MHz, CDCl$_3$) δ; 0.67 (s, 3H), 1.57-1.60 (m, 1H), 1.71 (s, 3H), 1.75-2.19 (m, 11H), 3.18 (s, 1H), 3.83 (s, 1H), 5.20 (s, 1H), 5.59 (br, 2H), 7.32 (d, J=4.4 Hz, 1H), 7.63 (t, J=8.1 Hz, 1H), 7.78 (t, J=8.1 Hz, 1H), 7.86 (d, J=8.1 Hz, 1H), 8.19 (d, J=8.1 Hz, 1H), 8.95 (d, J=4.4 Hz, 1H).
IR (ATR); 3356, 2924, 1740, 1662, 1367, 758 cm$^{-1}$.
FAB-MS m/z; 404 (M+H)$^+$.

Example 52

Preparation of trans-1-(5-fluoroadamantan-2-yl)-3,3-dimethyl-4-(2,3-dichlorophenyl)azetidin-2-one

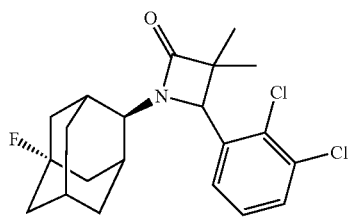

Under an argon atmosphere, a solution of trans-1-(5-hydroxyadamantan-2-yl)-3,3-dimethyl-4-(2,3-dichlorophenyl)azetidin-2-one (9.20 mg, 0.023 mmol) in dichloromethane (1 mL) was added with (diethylamino)sulfur trifluoride (4.60 μL, 0.350 mmol) at 0° C., and the resultant was stirred at the same temperature for 1 hour. The reaction solution was added with water and extracted with chloroform. The organic layer was dried over anhydrous sodium sulfate, and concentrated in vacuo.

trans-1-(5-Fluoroadamantan-2-yl)-3,3-dimethyl-4-(2,3-dichlorophenyl)azetidin-2-one (7.20 mg, 79%) was obtained as a white amorphous solid.

$^1$H-NMR (400 MHz, CDCl$_3$) δ; 0.74 (s, 3H), 1.50-1.63 (m, 5H), 1.75-2.05 (m, 9H), 2.28 (s, 1H), 3.22 (s, 1H), 3.61 (s, 1H), 5.07 (s, 1H), 7.18 (dd, J=1.2, 8.0 Hz, 1H), 7.28 (t, J=8.0 Hz, 1H), 7.44 (dd, J=1.2, 8.0 Hz, 1H).
IR (ATR); 2927, 1749, 1424, 1070, 778 cm$^{-1}$.
FAB-MS m/z; 396 (M+H)$^+$.

Example 53

Preparation of 1-(adamantan-2-yl)-3,3-dimethyl-4-(3-chlorophenyl)azetidin-2-one

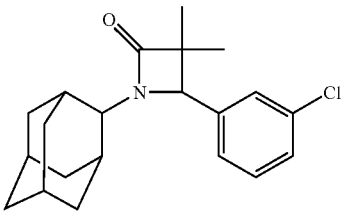

3-Chlorobenzaldehyde was used in place of benzaldehyde for a similar reaction and treatment as Example 1, and the title compound was obtained as a white amorphous solid.

$^1$H-NMR (400 MHz, CDCl$_3$) δ; 0.74 (s, 3H), 1.67 (s, 3H), 1.54-1.88 (m, 12H), 2.07 (d, J=12.9 Hz, 1H), 2.88 (s, 1H), 3.60 (s, 1H), 4.34 (s, 1H), 7.09-7.1.2 (m, 1H), 7.21 (d, J=2.0 Hz, 1H), 7.27-7.34 (m, 2H).
IR (ATR) 2908, 2854, 1732, 703 cm$^{-1}$.
EI-MS m/z; 343 (M$^+$).

Example 54

Preparation of 1-(adamantan-2-yl)-3,3-dimethyl-4-[3,5-bis(trifluoromethyl)phenyl]azetidin-2-one

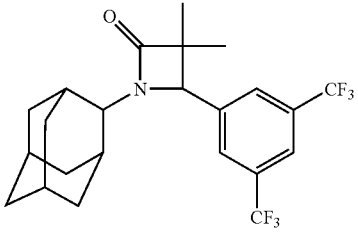

3,5-Bis(trifluoromethyl)benzaldehyde was used in place of benzaldehyde for a similar reaction and treatment as Example 1, and the title compound was obtained as a white amorphous solid.

$^1$H-NMR (400 MHz, CDCl$_3$) δ; 0.72 (s, 3H), 1.52 (s, 3H), 1.57-1.91 (m, 12H), 2.08 (d, J=13.2 Hz, 1H), 2.89 (s, 1H), 3.57 (s, 1H), 4.51 (s, 1H), 7.67 (s, 2H), 7.85 (s, 1H).
IR (ATR) 2925, 2854, 1743, 1732, 1276, 1140, 681 cm$^{-1}$.
EI-MS m/z; 445 (M$^+$).

Example 55

Preparation of 1-(adamantan-2-yl)-3,3-dimethyl-4-[4-(methyl thio)phenyl]azetidin-2-one

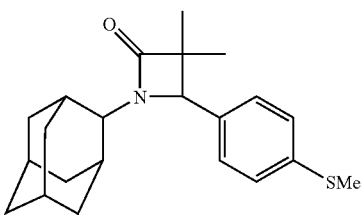

4-(Methylthio)benzaldehyde was used in place of benzaldehyde for a similar reaction and treatment as Example 1, and the title compound was obtained as a white amorphous solid.

$^1$H-NMR, (400 MHz, CDCl$_3$) δ; 0.74 (s, 3H), 1.45 (s, 3H), 1.52-1.87 (m, 12H), 2.10 (d, J=12.9 Hz, 1H), 2.50 (s, 3H), 2.87 (s, 1H), 3.59 (s, 1H), 4.34 (s, 1H), 7.13 (d, J=8.3 Hz, 2H), 7.26 (d, J=3.4 Hz, 2H).

IR (ATR) 2916, 2856, 1726, 825 cm$^{-1}$.

EI-MS m/z; 355 (M$^+$).

Example 56

Preparation of 1-(adamantan-2-yl)-3,3-dimethyl-4-(4-methoxy-2-methylphenyl)azetidin-2-one

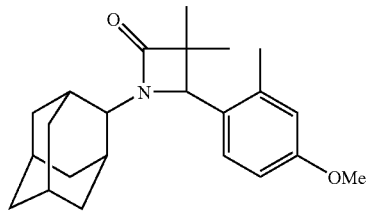

4-Methoxy-2-methyl benzaldehyde was used in place of benzaldehyde for a similar reaction and treatment as Example 1, and the title compound was obtained as a pale yellow oil.

$^1$H-NMR (400 MHz, CDCl$_3$) δ; 0.70 (s, 3H), 1.51 (s, 3H), 1.55-1.88 (m, 12H), 2.12 (d, J=12.9 Hz, 1H), 2.25 (s, 3H), 2.92 (s, 1H), 3.66 (s, 1H), 3.80 (s, 3H), 4.59 (s, 1H), 6.73-6.78 (m, 2H), 7.12 (d, J=8.3 Hz, 1H).

IR (ATR) 2906, 2853, 1742, 1253, 753 cm$^{-1}$.

EI-MS m/z; 353 (M$^+$).

Example 57

Preparation of trans-4-[2-(benzo[d][1,3]dioxol-4-yl)-3,3-dimethyl-4-oxoazetidin-1-yl]-N-methyl-1-adamantane carboxyamide

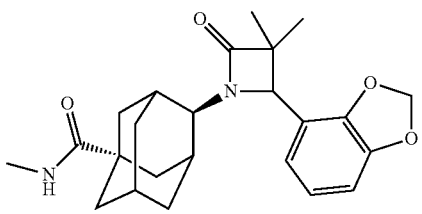

A solution of trans-4-[2-(benzo[d][1,3]dioxol-4-yl)-3,3-dimethyl-4-oxoazetidin-1-yl]-1-adamantane carboxylic acid (20.0 mg, 0.050 mmol) in dichloromethane (2 mL) was added with PyBOP (39.0 mg, 0.075 mmol), diisopropylethylamine (13.0 mg, 0.101 mmol) and a solution of 2 M methylamine in tetrahydrofuran (28.0 µL, 0.055 mmol) at room temperature, and the resultant was stirred at the same temperature for 2 hours. The reaction solution was added with water, and extracted with chloroform. The organic layer was dried over anhydrous sodium sulfate, and concentrated in vacuo. The obtained residue was purified using preparative thin-layer chromatography (hexane:ethyl acetate=1:5). trans-4-[2-(Benzo[d][1,3]dioxol-4-yl)-3,3-dimethyl-4-oxoazetidin-1-yl]-N-methyl-1-adamantane carboxyamide (19.8 mg, 96.5%) was obtained as a white crystalline powder.

$^1$H-NMR (400 MHz, CDCl$_3$) δ; 0.87 (s, 3H), 1.48 (s, 3H), 1.55-1.91 (m, 10H), 2.06-2.08 (m, 2H), 2.75 (d, J=4.6 Hz, 3H), 2.95 (s, 1H), 3.59 (s, 1H), 4.50 (s, 1H), 5.97 (dd, J=1.2, 7.3 Hz, 2H), 6.16 (s, 1H), 6.68 (dd, J=1.0, 7.6 Hz, 1H) 6.80 (dd, J=1.2, 7.8 Hz, 1H), 6.85 (t, J=7.8 Hz, 1H).

IR (ATR); 3365, 2921, 1732, 1639, 1460, 1251, 843 cm$^{-1}$.

EI-MS m/z; 410 (M$^+$).

Example 58

Preparation of trans-4-[2-(benzo[d][1,3]dioxol-4-yl)-3,3-dimethyl-4-oxoazetidin-1-yl]-N-ethyl-1-adamantane carboxyamide

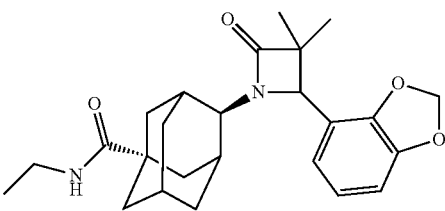

A solution of 2M ethylamine in tetrahydrofuran was used in place of a solution of 2M methylamine in tetrahydrofuran for a similar reaction and treatment as Example 57, and the title compound was obtained as a colorless oil.

$^1$H-NMR (400 MHz, CDCl$_3$) δ; 0.87 (s, 3H), 1.10 (t, J=7.3 Hz, 3H), 1.48 (s, 3H), 1.54-1.91 (m, 10H), 2.06-2.13 (m, 2H), 3.02 (s, 1H), 3.24 (quint, J=7.3 Hz, 2H), 3.58 (s, 1H), 4.47 (s, 1H), 5.52 (s, 1H), 5.97 (dd, J=1.2, 7.6 Hz, 2H), 6.68 (dd, J=1.1, 7.6 Hz, 1H), 6.78 (dd, J=1.5, 7.8 Hz, 1H), 6.84 (t, J=7.8 Hz, 1H).

IR (ATR); 3352, 2928, 1734, 1638, 1460, 1251, 757 cm$^{-1}$.

EI-MS m/z; 424 (M$^+$).

Example 59

Preparation of trans-4-[2-(benzo[d][1,3]dioxol-4-yl)-3,3-dimethyl-4-oxoazetidin-1-yl]-N-propyl-1-adamantane carboxyamide

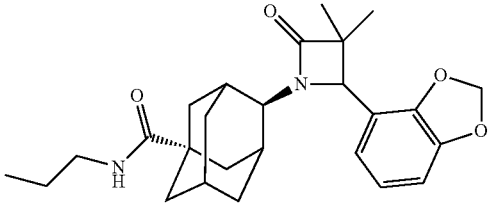

Propylamine was used in place of a solution of 2M methylamine in tetrahydrofuran for a similar reaction and treatment as Example 57, and the title compound was obtained as a colorless oil.

$^1$H-NMR (400 MHz, CDCl$_3$) δ; 0.87 (s, 3H), 0.89 (t, J=7.4 Hz, 3H), 1.46-1.91 (m, 12H), 1.48 (s, 3H), 2.06-2.13 (m, 2H), 3.02 (s, 1H), 3.18 (d, J=6.7 Hz, 2H), 3.58 (s, 1H), 4.47 (s, 1H), 5.53 (s, 1H), 5.97 (dd, J=1.3, 8.2 Hz, 2H), 6.68 (dd, J=1.1, 7.8 Hz, 1H), 6.79 (dd, J=1.1, 7.8 Hz, 1H), 6.84 (t, J=7.8 Hz, 1H).

IR (ATR); 3356, 2926, 1735, 1636, 1460, 1251, 760 cm$^{-1}$.

EI-MS m/z; 438 (M$^+$).

Example 60

Preparation of trans-4-[2-(benzo[d][1,3]dioxol-4-yl)-3,3-dimethyl-4-oxoazetidin-1-yl]-N-hexyl-1-adamantane carboxyamide

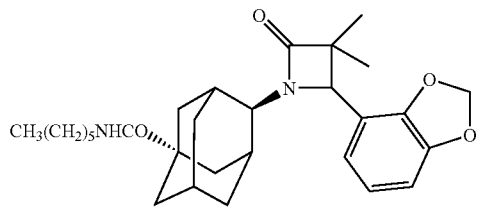

Hexylamine was used in place of a solution of 2M methylamine in tetrahydrofuran for a similar reaction and treatment as Example 57, and the title compound was obtained as a white amorphous solid.

$^1$H-NMR (400 MHz, CDCl$_3$) δ; 0.87 (s, 3H), 0.87 (t, J=6.7 Hz, 3H), 1.23-1.32 (m, 6H), 1.48 (s, 3H), 1.44-1.91 (m, 12H), 2.06-2.13 (m, 2H), 3.02 (s, 1H), 3.20 (q, J=6.7 Hz, 2H), 3.58 (s, 1H), 4.47 (s, 5.51 (s, 1H), 5.97 (dd, J=1.3, 8.2 Hz, 2H), 6.68 (dd, J=1.1, 7.7 Hz, 1H), 6.79 (dd, J=1.4, 7.7 Hz, 1H), 6.84 (t, J=7.7 Hz, 1H).

IR (ATR); 3375, 2925, 1737, 1635, 1460, 1251, 730 cm$^{-1}$.

EI-MS m/z; 480 (M$^+$).

Example 61

Preparation of trans-4-[2-(benzo[d][1,3]dioxol-4-yl)-3,3-dimethyl-4-oxoazetidin-1-yl]-N-octyl-1-adamantane carboxyamide

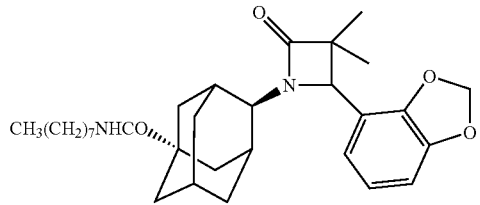

Octylamine was used in place of a solution of 2M methylamine in tetrahydrofuran for a similar reaction and treatment as Example 57, and the title compound was obtained as a white amorphous solid.

$^1$H-NMR (400 MHz, CDCl$_3$) δ; 0.85-0.89 (m, 6H), 1.23-1.27 (m, 10H), 1.48 (s, 3H), 1.54-1.91 (m, 12H), 2.06-2.13 (m, 2H), 3.02 (s, 1H), 3.19 (q, j=6.7 Hz, 2H), 3.58 (s, 1H), 4.47 (s, 1H), 5.53 (br, 1H), 5.97 (dd, J=1.3, 8.2 Hz, 2H), 6.68 (d, J=7.8 Hz, 1H), 6.79 (dd, J=1.3, 7.8 Hz, 1H), 6.84 (t, J=7.8 Hz, 1H).

IR (ATR); 3374, 2924, 1738, 1635, 1460, 1251, 730 cm$^{-1}$.

EI-MS m/z; 508 (M$^+$).

Example 62

Preparation of trans-4-[2-(benzo[d][1,3]dioxol-4-yl)-3,3-dimethyl-4-oxoazetidin-1-yl]-N-cyclopropyl-1-adamantane carboxyamide

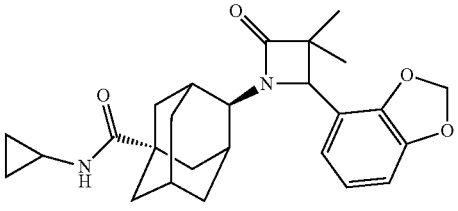

Cyclopropylamine was used in place of a solution of 2M methylamine in tetrahydrofuran for a similar reaction and treatment as Example 57, and the title compound was obtained as a colorless oil.

$^1$H-NMR (400 MHz, CDCl$_3$) δ; 0.40-0.44 (m, 2H), 0.70-0.77 (m, 2H), 0.86 (s, 3H), 1.48 (s, 3H), 1.53-1.87 (m, 10H), 2.05-2.12 (m, 2H), 2.67 (oct, J=3.6 Hz, 1H), 3.01 (s, 1H), 3.56 (s, 1H), 4.46 (s, 1H), 5.63 (s, 1H), 5.97 (dd, J=1.5, 8.3 Hz, 2H), 6.68 (d, J=7.8 Hz, 1H), 6.78 (dd, J=1.5, 7.8 Hz, 1H), 6.84 (t, J=7.8 Hz, 1H).

IR (ATR); 3350, 2924, 1732, 1638, 1460, 1251, 754 cm$^{-1}$.

EI-MS m/z; 436 (M$^+$).

Example 63

Preparation of trans-4-[2-(benzo[d][1,3]dioxol-4-yl)-3,3-dimethyl-4-oxoazetidin-1-yl]-N-cyclohexyl-1-adamantane carboxyamide

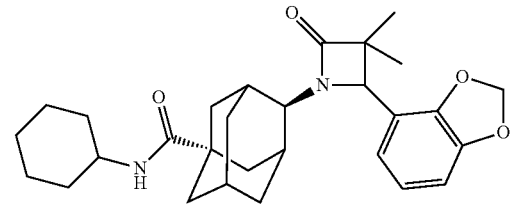

Cyclohexylamine was used in place of a solution of 2M methylamine in tetrahydrofuran for a similar reaction and treatment as Example 57, and the title compound was obtained as a white amorphous solid.

$^1$H-NMR (270 MHz, CDCl$_3$) δ; 0.86 (s, 3H), 0.99-1.88 (m, 20H), 1.47 (s, 3H), 2.06-2.13 (m, 2H), 3.00 (s, 1H), 3.57 (s, 1H), 3.64-3.78 (m, 1H), 4.46 (s, 1H), 5.36 (d, J=7.8 Hz, 1H), 5.96 (dd, J=1.0, 6.6 Hz, 2H), 6.68 (dd, J=1.6, 7.6 Hz, 1H), 6.76-6.86 (m, 2H).

IR (ATR); 3356, 2927, 1736, 1633, 1460, 1251, 729 cm$^{-1}$.

EI-MS m/z; 478 (M$^+$).

Example 64

Preparation of trans-4-[2-(benzo[d][1,3]dioxol-4-yl)-3,3-dimethyl-4-oxoazetidin-1-yl]-N-benzyl-1-adamantane carboxyamide

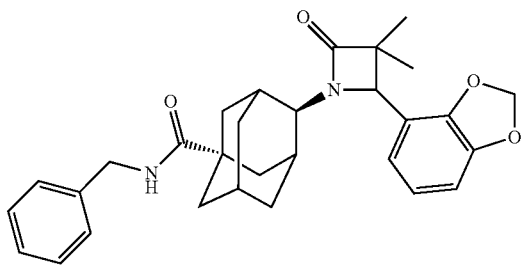

Benzylamine was used in place of a solution of 2M methylamine in tetrahydrofuran for a similar reaction and treatment as Example 57, and the title compound was obtained as a white amorphous solid.

$^1$H-NMR (270 MHz, CDCl$_3$) δ; 0.86 (s, 3H), 1.47 (s, 3H), 1.53-2.14 (m, 12H), 3.02 (s, 1H), 3.58 (s, 1H), 4.40 (d, J=5.1 Hz, 2H), 4.46 (s, 1H), 5.83 (br, 1H), 5.96 (dd, J=1.4, 5.9 Hz, 2H), 6.67 (dd, J=1.4, 7.4 Hz, 1H), 6.76-6.83 (m, 2H), 7.21-7.32 (m, 5H).

IR (ATR); 3357, 2910, 1736, 1639, 1459, 1251, 1056, 729 cm$^{-1}$.

EI-MS m/z; 486 (M$^+$).

Example 65

Preparation of methyl trans-2-[4-(2-(benzo[d][1,3]dioxol-4-yl)-3,3-dimethyl-4-oxoazetidin-1-yl)-1-adamantane carboxyamide]acetate

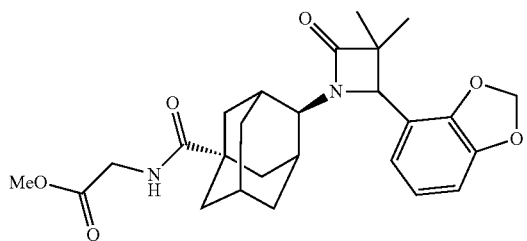

Methylglycine was used in place of a solution of 2M methylamine in tetrahydrofuran for a similar reaction and treatment as Example 57, and the title compound was obtained as a colorless oil.

$^1$H-NMR (400 MHz, CDCl$_3$) δ; 0.87 (s, 3H), 1.48 (s, 3H), 1.55-1.95 (m, 10H), 2.01-2.17 (m, 2H), 3.03 (s, 1H), 3.59 (s, 1H), 3.75 (s, 3H), 4.00 (d, J=4.9 Hz, 2H), 4.47 (s, 1H), 5.97 (dd, J=1.2, 8.3 Hz, 2H), 6.09 (t, J=4.9 Hz, 1H), 6.68 (dd, J=1.2, 7.8 Hz, 1H), 6.79 (dd, J=1.2, 7.8 Hz, 1H), 6.85 (t, J=7.8 Hz, 1H).

IR (ATR); 3356, 2920, 1736, 1646, 1460, 1251, 1205, 757 cm$^{-1}$.

EI-MS m/z; 468 (M$^+$).

Example 66

Preparation of trans-2-[4-(2-(benzo[d][1,3]dioxol-4-yl)-3,3-dimethyl-4-oxoazetidin-1-yl)-1-adamantane carboxyamide]acetic acid

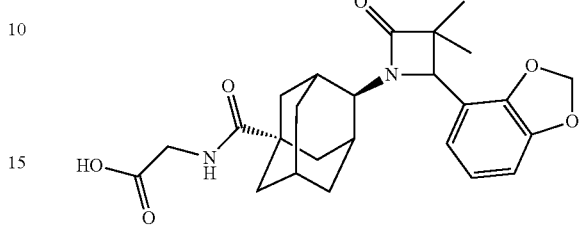

A solution of trans-methyl 2-[4-(2-(benzo[d][1,3]dioxol-4-yl)-3,3-dimethyl-4-oxoazetidin-1-yl)-1-adamantane carboxyamide]acetate (20.0 mg, 0.050 mmol) in methanol (2 mL) was added with an aqueous solution of 4N-sodium hydroxide (1 mL) at room temperature, and the resultant was stirred at the same temperature for 2 hours. The reaction solution was concentrated in vacuo, the obtained residue was added with water, and washed with diethyl ether. The aqueous layer was added with 4N-hydrochloric acid until it becomes a liquid of pH=1.0, and extracted with chloroform. The organic layer was dried over anhydrous sodium sulfate, concentrated in vacuo, and trans-2-[4-(2-(benzo[d][1,3]dioxol-4-yl)-3,3-dimethyl-4-oxo azetidin-1-yl)-1-adamantane carboxyamide] acetic acid (24.1 mg, 100%) was obtained as a white crystalline powder.

$^1$H-NMR (400 MHz, CDCl$_3$) δ; 0.87 (s, 3H), 1.48 (s, 3H), 1.54-1.94 (m, 10H), 2.07-2.11 (m, 2H), 3.00 (s, 1H), 3.60 (s, 1H), 4.00 (d, J=4.9 Hz, 2H), 4.49 (s, 1H), 5.97 (dd, J=1.5, 9.0 Hz, 2H), 6.32 (t, J=4.9 Hz, 1H), 6.68 (d, J=7.8 Hz, 1H), 6.79 (dd, J=1.3, 7.8 Hz, 1H), 6.84 (t, J=7.8 Hz, 1H).

IR (ATR); 3375, 2926, 1731, 1644, 1460, 1251, 1221, 754 cm$^{-1}$.

EI-MS m/z; 454 (M$^+$).

Example 67

Preparation of 1-(adamantan-2-yl)-4-(2,5-dihydrobenzo[b]oxepin-9-yl)-3,3-dimethylazetidin-2-one

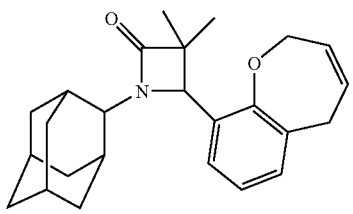

Step 1

Preparation of 2,5-dihydrobenzo[b]oxepin-9-carboxyaldehyde

Under an argon atmosphere, a solution of 3-allyl-2-allyloxybenzaldehyde (480 mg, 2.40 mmol) in dichloromethane (24 mL) synthesized by a method described in Tetrahedron, 61, p. 7746-7755, was added with a Grubbs second generation catalyst (benzylidene{1,3-bis(2,4,6-trimethylphenyl)-2-imidazolidinylidene}dichloro(tricyclohexylphosphine)ruthenium) (50.0 mg, 2.50 mol %) at TOM temperature, and the resultant was stirred at the same temperature for 3 hours. The reaction solution was concentrated in vacuo, and the obtained residue was purified using silica gel chromatography (hexane:ethyl acetate=4:1). 2,5-dihydrobenzo[b]oxepin-9-carboxyaldehyde (384 mg, 91.7%) was obtained as a colorless oil.

$^1$H-NMR (400 MHz, CDCl$_3$) δ; 3.55 (s, 2H), 4.73 (s, 2H), 5.51-5.54 (m, 1H), 5.88-5.93 (m, 1H), 7.13 (t, J=7.8 Hz, 1H), 7.36 (d, J=7.8 Hz, 1H), 7.73 (d, J=7.8 Hz, 1H), 10.46 (s, 1H).

Step 2

Preparation of 1-(adamantan-2-yl)-4-(2,5-dihydrobenzo[b]oxepin-9-yl)-3,3-dimethylazetidin-2-one 2,5-Dihydrobenzo[b]oxepin-9-carboxyaldehyde (363 mg, 2.00 mmol) was used in place of benzaldehyde for a similar reaction and treatment as Example 1, and the title compound was obtained as a colorless oil.

$^1$H-NMR (400 MHz, CDCl$_3$) δ: 0.79 (s, 3H), 1.49-1.85 (m, 15H), 2.09-2.13 (m, 1H), 2.89 (s, 1H), 2.96-3.02 (m, 1H), 3.37-3.43 (m, 1H), 3.65 (s, 1H), 4.65 (s, 1H), 5.20-5.23 (m, 2H), 5.32-5.37 (m, 1H), 5.95-6.04 (m, 1H), 6.86 (t, J=7.5 Hz, 1H), 7.00 (d, J=7.5 Hz, 1H), 7.09 (d, J=7.5 Hz, 1H).

IR (ATR); 2906, 1743, 1455, 1329, 1181, 939, 756 cm$^{-1}$.

EI-MS m/z; 377 (M$^+$).

Example 68

Preparation of 1-(adamantan-2-yl)-3,3-dimethyl-4-(benzo[b]oxepan-9-yl)azetidin-2-one

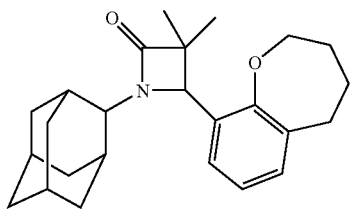

A solution of 1-(adamantan-2-yl)-4-(2,5-dihydrobenzo[b]oxepin-9-yl)-3,3-dimethylazetidin-2-one (21.1 mg, 0.0560 mmol) in methanol (2 mL) was added with palladium carbon ethylenediamine complex (catalyst amount), and the resultant was stirred at room temperature for 6 hours under a hydrogen atmosphere. The reaction solution was filtered using celite, concentrated in vacuo, and 1-(adamantan-2-yl)-3,3-dimethyl-4-(benzo[b]oxepan-9-yl)azetidin-2-one (16.2 mg, 76.2%) was obtained as a colorless oil.

$^1$H-NMR (400 MHz, CDCl$_3$) δ; 0.80 (s, 3H), 1.00-1.87 (m, 19H), 2.09-2.13 (m, 1H), 2.82-2.91 (m, 2H), 3.24-3.30 (m, 1H), 3.65 (s, 1H), 4.59-4.78 (m, 2H), 6.81 (t, J=7.8 Hz, 1H), 6.96 (d, J=7.8 Hz, 1H), 7.07 (d, J=7.8 Hz, 1H).

IR (ATR); 2907, 1743, 1456, 1329, 1184, 931, 754 cm$^{-1}$.

EI-MS m/z, 379 (M$^+$).

Example 69

Preparation of 4-benzyl-1-(adamantan-2-yl)-3,3-dimethylazetidin-2-one

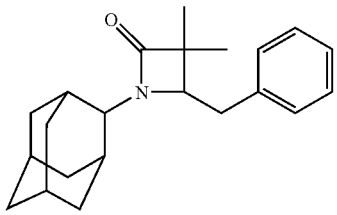

A solution of 2-adamantylamine (310 mg, 2.05 mmol) in toluene (15 mL) was added with phenylacetaldehyde (246 mg, 2.05 mmol) at room temperature, and the resultant was stirred at the same temperature for 1 hour. The reaction solution was concentrated in vacuo, and the obtained residue was dissolved in toluene (15 mL), to which ethyl 2-bromoisobutylate (1.20 g, 6.15 mmol) and zinc (4.02 g, 61.5 mmol) were sequentially added at room temperature. The reaction solution was stirred at 135° C. for 5 hours, and the residue was filtered with a filter paper for Kiriyama funnel. The reaction solution was added with hydrochloric acid, and extracted with ethyl acetate. The organic layer was dried over anhydrous sodium sulfate, and concentrated in vacuo. The obtained residue was purified using column chromatography (hexane:diethylether=1:1). 4 Benzyl-1-(adamantan-2-yl)-3,3-dimethylazetidin-2-one (44.8 mg, 5.4%) was obtained as a colorless oil.

$^1$H-NMR (400 MHz, CDCl$_3$) δ; 1.13 (s, 3H), 1.16-1.89 (m, 15H), 2.09-2.12 (m, 1H), 2.73 (s, 1H), 2.85 (dd, J=8.1, 14.6 Hz, 1H), 3.00 (dd, J=5.6, 14.6 Hz, 1H), 3.44 (s, 1H), 3.60 (dd, J=5.6, 8.1 Hz, 1H), 7.18-7.31 (m, 5H).

IR (ATR) 2912, 1734, 1330, 1111, 741 cm$^{-1}$.

EI-MS m/z; 323 (M$^+$).

Example 70

Preparation of 4-[1-(4-chlorophenyl)cyclopropyl]-1-(adamantan-2-yl)-3,3-dimethylazetidin-2-one

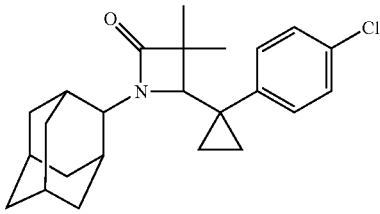

Step 1

Preparation of 1-(4-chlorophenyl)cyclopropane carboaldehyde

A solution of 1-(4-chlorophenyl)cyclopropane carboxylic acid (784 mg, 3.99 mmol) in dichloromethane (30 mL) was added sequentially at room temperature with N,O-dimethyl-hydroxylamine hydrochloride (389 mg, 3.99 mmol), benzotriazole-1-yloxytrispyrrolidinophosphonium hexafluorophosphate (2.28 g, 4.39 mmol) and triethylamine (807 mg, 7.97 mmol). The resultant was stirred at the same temperature for 20 min, and extracted with chloroform. The organic layer was dried over anhydrous sodium sulfate, and concentrated in vacuo. The obtained residue was dissolved in toluene (30 mL), added at −78° C. with a solution of diisobutylaluminum hydride in toluene (1.01 M, 4.35 mL), and the resultant was stirred at the same temperature for 1 hour. The reaction solution was added with hydrochloric acid, and extracted with ethyl acetate. The organic layer was dried over anhydrous sodium sulfate, and concentrated in vacuo. The obtained residue was purified using column chromatography (hexane:ethyl acetate=3:1), and 1-(4-chlorophenyl)cyclopropane carboaldehyde (460 mg, 63.7%) was obtained.

$^1$H-NMR (400 MHz, CDCl$_3$) δ; 1.38-1.40 (m, 2H), 1.53-1.59 (m, 2H), 7.23-7.26 (m, 2H), 7.30-7.35 (m, 2H), 9.16 (s, 1H).

Step 2

Preparation of 4-[1-(4-chlorophenyl)cyclopropyl]-1-(adamantan-2-yl)-3,3-dimethylazetidin-2-one 1-(4-Chlorophenyl)cyclopropane carboaldehyde was used in place of phenylacetaldehyde for a similar reaction and treatment as Example 69, and the title compound was obtained as a colorless oil.

$^1$H-NMR (400 MHz, CDCl$_3$) δ; 0.60-0.66 (m, 1H), 0.87-0.91 (m, 1H), 1.04 (s, 3H), 1.14-1.89 (m, 16H), 1.97-2.00 (m, 1H), 2.20 (s, 1H), 2.92 (s, 1H), 3.39 (s, 1H), 3.89 (s, 1H), 7.19 (d, J=8.8 Hz, 2H), 7.24 (d, J=8.8 Hz, 2H).

IR (ATR) 2908, 1741, 1493, 1324, 1014, 751 cm$^{-1}$.

EI-MS m/z; 383 (M$^+$).

Example 71

Preparation of 1-(adamantan-2-yl)-3,3-dimethyl-4-(1-phenylcyclopropyl)azetidin-2-one

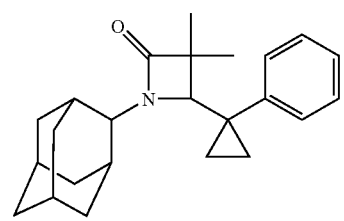

1-Phenylcyclopropane carboaldehyde was used in place of phenylacetaldehyde for a similar reaction and treatment as Example 69, and the title compound was obtained as a colorless oil.

$^1$H-NMR (400 MHz, CDCl$_3$) δ; 0.64-0.69 (m, 1H), 0.86-0.91 (m, 1H), 1.06 (s, 3H), 1.09-1.88 (m, 16H), 1.97-1.99 (m, 1H), 2.23 (s, 1H), 2.93 (s, 1H), 3.41 (s, 1H), 3.96 (s, 1H), 7.17-7.39 (m, 5H).

IR (ATR) 2908, 2856, 1741, 1325, 1117, 762 cm$^{-1}$.

EI-MS m/z; 349 (M$^+$).

Example 72

Preparation of 1-(adamantan-2-yl)-4-[1-(4-methoxyphenyl)cyclopropyl]-3,3-dimethylazetidin-2-one

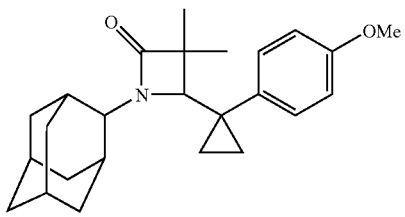

Step 1

Preparation of 1-(4-methoxyphenyl)cyclopropane carboaldehyde

Under an argon atmosphere, a solution of 1-(4-methoxyphenyl)cyclopropane carboxylic acid (2.00 g, 10.4 mmol) in tetrahydrofuran (20 mL) was added with lithium aluminum hydride (513 mg, 13.5 mmol) at 0° C., and the resultant was stirred at room temperature for 2 hours. The resultant was added sequentially with water and hydrochloric acid at 0° C., stirred at room temperature for 30 min and then extracted with ethyl acetate. The organic layer was dried over anhydrous sodium sulfate, and concentrated in vacuo. The obtained residue was dissolved in dichloromethane (15 mL). The resultant was sequentially added with molecular sieves 4β (1.80 g), N-methylmorpholine (1.83 g, 15.6 mmol) and tetrapropylammonium perruthenate (1.83 mg, 0.520 mmol) at 0° C., and stirred at room temperature for 1.5 hours. The reaction solution was filtered using celite, and concentrated in vacuo. The obtained residue was purified using column chromatography (hexane:ethyl acetate=4:1), and 1-(4-methoxyphenyl)cyclopropane carboaldehyde (1.54 g, 84.0%) was obtained.

$^1$H-NMR (400 MHz, CDCl$_3$) δ; 1.35-1.38 (m, 2H), 1.53-1.56 (m, 2H), 3.81 (s, 1H), 6.88-6.93 (m, 2H), 7.21-7.28 (m, 2H), 9.23 (s, 1H).

Step 2

Preparation of 1-(adamantan-2-yl)-4-[1-(4-methoxyphenyl)cyclopropyl]-3,3-dimethylazetidin-2-one 1-(4-Methoxyphenyl)cyclopropane carboaldehyde was used in place of phenylacetaldehyde for a similar reaction and treatment as Example 69, and the title compound was obtained as a pale yellow amorphous solid.

$^1$H-NMR (400 MHz, CDCl$_3$) δ; 0.61-0.65 (m, 1H), 0.82-0.85 (m, 1H), 1.08 (s, 3H), 1.10-1.15 (m, 2H), 1.24 (s, 3H), 1.64-1.89 (m, 11H), 2.00 (d, J=11.5 Hz, 1H), 2.24 (s, 1H), 2.92 (s, 1H), 3.42 (s, 1H), 3.79 (s, 3H), 3.83 (s, 1H), 6.81-6.86 (m, 2H), 7.18-7.23 (m, 2H).

IR (ATR); 2905, 2859, 1740, 1514, 1238 cm$^{-1}$.

EI-MS m/z; 379 (M$^+$).

Example 73

Preparation of 1-(adamantan-2-yl)-3,3-dimethyl-4-(1-p-tolylcyclopropyl)azetidin-2-one

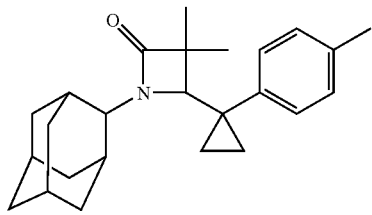

Step 1: Preparation of 1-p-tolylcyclopropane carboaldehyde

Under an argon atmosphere, a solution of 1-p-tolylcyclopropane carbonitrile (1.57 g, 10.0 mmol) in toluene (70 mL) was added with a solution of lithium diisobutylaluminum hydride in toluene (1.01 M, 23.1 mL) at 0° C., and the resultant was stirred at the same temperature for 1 hour. The reaction solution was added with hydrochloric acid at 0° C., and extracted with ethyl acetate. The organic layer was dried over anhydrous sodium sulfate, and concentrated in vacuo. The obtained residue was purified using column chromatography (hexane:ethyl acetate=9:1). 1-p-tolylcyclopropane carboaldehyde (960 mg, 59.9%) was obtained.

$^1$H-NMR (400 MHz, CDCl$_3$) δ; 1.34-1.40 (m, 2H), 1.57-1.59 (m, 2H), 7.18 (d, J=8.6 Hz, 2H), 7.49 (d, J=8.3 Hz, 2H), 9.15 (s, 1H).

Step 2: Preparation of 1-(adamantan-2-yl)-3,3-dimethyl-4-(1-p-tolylcyclopropyl)azetidin-2-one 1-p-tolylcyclopropane carboaldehyde was used in place of phenylacetaldehyde for a similar reaction and treatment as Example 69, and the title compound was obtained as a colorless oil.

$^1$H-NMR (400 MHz, CDCl$_3$) δ; 0.63-0.66 (m, 1H), 0.84-0.88 (m, 1H), 1.06 (s, 3H), 1.08-190 (m, 16H), 1.98-2.01 (m, 1H), 2.23 (s, 1H), 2.31 (s, 3H), 2.92 (s, 1H), 3.41 (s, 1H), 3.91 (s, 1H), 7.08 (d, J=8.1 Hz, 2H), 7.14 (d, J=8.1 Hz, 2H).
IR (ATR) 2981, 2912, 1758, 1732, 1469, 1388, 1255, 1147, 1101 cm$^{-1}$.
EI-MS m/z; 363 (M$^+$).

Example 74

Preparation of 4-(1-[benzo[d][1,3]dioxol-5-yl]cyclopropyl]-1-(adamantan-2-yl)-3,3-dimethylazetidin-2-one

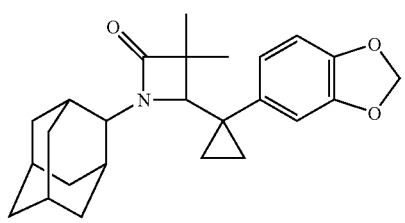

Step 1

Preparation of 1-(benzo[d][1,3]dioxol-5-yl)cyclopropane carboaldehyde 2-(Benzo[d][1,3]dioxol-5-yl)acetonitrile (1.50 g, 9.31 mmol) was cyclopropylated according to the method described in WO2005/019161. Then, a solution of the obtained product in toluene (100 mL) was added with a solution of lithium diisobutylaluminum hydride in toluene (1.01 M, 9.22 mL) at 0° C., and the resultant was stirred for 1 hour. The reaction solution was added with hydrochloric acid at 0° C., and extracted with ethyl acetate. The organic layer was dried over anhydrous sodium sulfate, and concentrated in vacuo. The obtained residue was purified using column chromatography (hexane:ethyl acetate=4:1), and 1-(benzo[d][1,3]dioxol-5-yl)cyclopropane carboaldehyde (117 mg, 6.7%) was obtained.

$^1$H-NMR (400 MHz, CDCl$_3$) δ; 1.34-1.37 (m, 2H), 1.52-1.54 (m, 2H), 5.96 (d, J=2.0 Hz, 2H), 6.75-6.80 (m, 3H), 9.20 (s, 1H).

Step 2

Preparation of 4-[1-(benzo[d][1,3]dioxol-5-yl)cyclopropyl]-1-(adamantan-2-yl)-3,3-dimethylazetidin-2-one 1-(Benzo[d][1,3]dioxol-5-yl)cyclopropane carboaldehyde was used in place of phenylacetaldehyde for a similar reaction and treatment as Example 69, and the title compound was obtained as a colorless oil.

$^1$H-NMR (400 MHz, CDCl$_3$) δ; 0.55-0.63 (m, 1H), 0.77-0.86 (m, 1H), 1.04 (s, 3H), 1.10-2.00 (m, 17H), 2.22 (s, 1H), 292 (s, 1H), 3.40 (s, 1H), 3.83 (s, 1H), 5.94 (s, 2H), 6.70-6.77 (m, 3H).
IR (ATR) 2906, 1853, 1741, 1505, 1229, 1038 cm$^{-1}$.
EI-MS m/z; 393 (M$^+$).

Example 75

Preparation of 4-[1-(4-bromophenyl)cyclopropyl]-1-(adamantan-2-yl)-3,3-dimethylazetidin-2-one

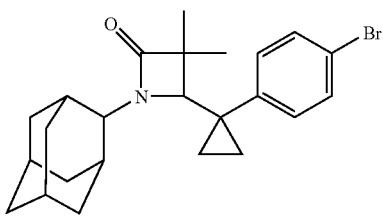

Step 1

Preparation of 1-(4-bromophenyl)cyclopropane carboaldehyde 2-(4-Bromophenyl)acetonitrile was used in place of 2-(benzo[d][1,3]dioxol-5-yl)acetonitrile for a similar reaction and treatment of Step 1 of Example 74, and the title compound was obtained.

$^1$H-NMR (400 MHz, CDCl$_3$) δ; 1.34-1.40 (m, 2H), 1.57-1.59 (m, 2H), 7.18 (d, J=8.6 Hz, 2H), 7.49 (d, J=8.3 Hz, 2H), 9.15 (s, 1H).

Step 2

Preparation of 4-[1-(4-bromophenyl)cyclopropyl]-1-(adamantan-2-yl)-3,3-dimethylazetidin-2-one 1-(4-Bromophenyl)cyclopropane carboaldehyde was used in place of phenylacetaldehyde for a similar reaction and treatment as Example 69, and the title compound was obtained as a pale yellow amorphous solid.

$^1$H-NMR (400 MHz, CDCl$_3$) δ; 0.60-0.66 (m, 1H), 0.87-0.92 (m, 1H), 1.04 (s, 3H), 1.13-1.19 (m, 2H), 1.26 (s, 3H), 1.61-1.89 (m, 11H), 1.99 (d, J=13.2 Hz, 1H), 2.20 (s, 1H), 2.92 (s, 1H), 339 (s, 1H), 3.89 (s, 1H), 7.14 (d, J=8.5 Hz, 2H), 7.41 (d, J=8.6 Hz, 2H).

IR (ATR); 2907, 2855, 1741, 1086, 1010 cm$^{-1}$.

EI-MS m/z; 427 (M$^+$).

Example 76

Preparation of 1-(adamantan-2-yl)-3,3-dimethyl-4-[1-(pyridin-2-yl)cyclopropyl]azetidin-2-one

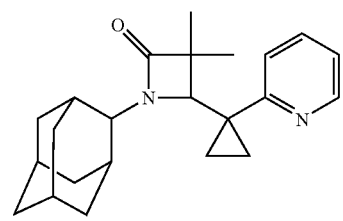

Step 1

Preparation of 1-(pyridin-2-yl)cyclopropane carboaldehyde 2-(Pyridin-2-yl)acetonitrile was used in place of 2-(benzo[d][1,3]dioxol-5-yl)acetonitrile for a similar reaction and treatment as Step 1 of Example 74, and the title compound was obtained.

$^1$H-NMR (400 MHz, CDCl$_3$) δ; 1.63-1.68 (m, 2H), 1.70-1.74 (m, 2H), 7.16-7.20 (m, 1H), 7.53-7.56 (m, 1H), 7.65-7.68 (m, 1H), 8.55 (d, J=1.9 Hz, 1H), 9.54 (s, 1H).

Step 2

Preparation of 1-(adamantan-2-yl)-3,3-dimethyl-4-[1-(pyridin-2-yl)cyclopropyl]azetidin-2-one 1-(Pyridin-2-yl)cyclopropane carboaldehyde was used in place of phenylacetaldehyde for a similar reaction and treatment as Example 69, and the title compound was obtained as a pale yellow oil.

$^1$H-NMR (400 MHz, CDCl$_3$) δ; 0.91 (s, 3H), 0.95-1.00 (m, 2H), 1.22-1.30 (m, 1H), 1.38-1.41 (m, 1H), 1.46 (s, 3H), 1.58 (s, 2H), 1.66-1.75 (m, 5H), 1.82-1.88 (m, 4H), 2.03 (d, J=12.4 Hz, 1H), 2.17 (s, 1H), 2.95 (s, 1H), 3.36 (s, 1H), 4.32 (s, 1H), 7.02-7.09 (m, 2H), 7.55-7.59 (m, 1H), 8.48-8.49 (m, 1H).

IR (ATR); 2917, 2853, 1736, 775, 739 cm$^{-1}$.

EI-MS m/z; 350 (M$^+$).

Example 77

Preparation of 4-[1-(2-chlorophenyl)cyclopropyl]-1-(adamantan-2-yl)-3,3-dimethylazetidin-2-one

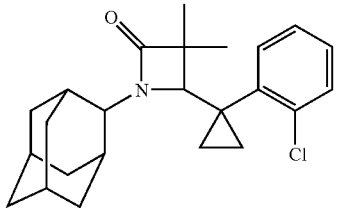

Step 1

Preparation of 1-(2-chlorophenyl)cyclopropane carboaldehyde 2-(2-Chlorophenyl)acetonitrile was used in place of 2-(benzo[d][1,3]dioxol-5-yl)acetonitrile for a similar reaction and treatment as Step 1 of Example 74, and the title compound was obtained.

$^1$H-NMR (400 MHz, CDCl$_3$) δ; 1.39-1.42 (m, 2H), 1.69-1.72 (m, 2H), 7.26-7.30 (m, 3H), 7.43-7.45 (m, 1H), 9.17 (s, 1H).

Step 2

Preparation of 4-[1-(2-chlorophenyl)cyclopropyl]-1-(adamantan-2-yl)-3,3-dimethylazetidin-2-one 1-(2-Chlorophenyl)cyclopropane carboaldehyde was used in place of phenylacetaldehyde for a similar reaction and treatment as Example 69, and the title compound was obtained as a colorless oil.

$^1$H-NMR (400 MHz, CDCl$_3$) δ; 0.50-0.55 (m, 1H), 1.01-1.06 (m, 1H), 1.11 (s, 3H), 1.19-1.94 (m, 17H), 2.45 (s, 1H), 2.96 (s, 1H), 3.37 (s, 1H), 4.23 (s, 1H), 7.18-7.19 (m, 2H), 7.36-7.39 (m, 2H).

IR (ATR) 2909, 737, 1471, 1327, 1045, 751 cm$^{-1}$.

EI-MS m/z; 383 (M$^+$).

Example 78

Preparation of 4-[1-(3-chlorophenyl)cyclopropyl]-1-(adamantan-2-yl)-3,3-dimethylazetidin-2-one

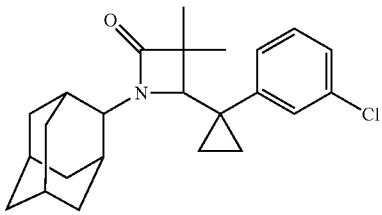

Step 1

Preparation of 1-(3-chlorophenyl)cyclopropane carboaldehyde 2-(3-Chlorophenyl)acetonitrile was used in place of 2-(benzo[d][1,3]dioxol-5-yl)acetonitrile for a similar reaction and treatment as Step 1 of Example 74, and the title compound was obtained.

$^1$H-NMR (400 MHz, CDCl$_3$) δ; 1.40-1.43 (m, 2H), 1.58-1.61 (m, 2H), 7.19 (m, 1H), 7.26-7.30 (m, 3H), 9.21 (s, 1H).

Step Preparation of 4-[1-(3-chlorophenyl)cyclopropyl]-1-(adamantan-2-yl)-3,3-dimethylazetidin-2-one 2-(3-Chlorophenyl)acetonitrile was used in place of phenylacetaldehyde for a similar reaction and treatment as Example 69, and the title compound was obtained as a colorless oil.

$^1$H-NMR (400 MHz, CDCl$_3$) δ; 0.64-0.66 (m, 1H), 0.90-0.93 (m, 1H), 1.05 (s, 3H), 1.11-2.04 (m, 17H), 2.19 (s, 1H), 2.92 (s, 1H), 3.39 (s, 1H), 3.92 (s, 1H), 7.14-7.22 (m, 4H).

IR (ATR) 2908, 1740, 1358, 1121, 750 cm$^{-1}$.

EI-MS m/z; 383 (M$^+$).

Example 79

Preparation of 4-[1-(biphenyl-4-yl)cyclopropyl]-1-(adamantan-2-yl)-3,3-dimethylazetidin-2-one

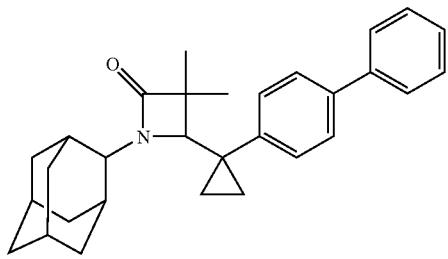

A solution of 4-[1-(4-bromophenyl)cyclopropyl]-1-(adamantan-2-yl)-3,3-dimethylazetidin-2-one (12.2 mg, 0.0285 mmol) in 1,4-dioxane (3 mL) prepared in Example 75 was added with tetrakis(triphenylphosphine) palladium (1.6 mg, 1.4 μmol), phenyl boronic acid (7 mg, 0.057 mmol), and potassium phosphate (30 mg, 0.142 mmol) at room temperature, and the resultant was stirred at 100° C. for 20 hours. The reaction solution was poured into water, and extracted with ethyl acetate. The organic layer was dried over anhydrous sodium sulfate, and concentrated in vacuo. The obtained residue was purified using thin-layer chromatography (hexane:ethyl acetate=3:1), and 4-[1-(biphenyl-4-yl)cyclopropyl]-1-(adamantan-2-yl)-3,3-dimethylazetidin-2-one (10.2 mg, 84%) was obtained as a white amorphous solid.

$^1$H-NMR (400 MHz, CDCl$_3$) δ; 0.70-0.75 (m, 1H), 0.90-0.95 (m, 1H), 1.10 (s, 3H), 1.16-1.28 (m, 2H), 1.31 (s, 3H), 1.59-2.04 (m, 12H), 2.25 (s, 1H), 2.95 (s, 1H), 3.44 (s, 1H), 3.97 (s, 1H), 7.31-7.35 (m, 3H), 7.43 (t, J=8.4 Hz, 2H), 7.52 (d, J=8.4 Hz, 2H), 7.58 (d, J=8.4 Hz, 21-1).

IR (ATR) 2908, 1740, 1326, 1221, 1086, 762 cm$^{-1}$.

EI-MS m/z; 425 (M$^+$).

Example 80

Preparation of methyl trans-4-{2-[1-(pyridin-2-yl)cyclopropyl]-3,3-dimethyl-4-oxoazetidin-1-yl}-1-adamantane carboxylate

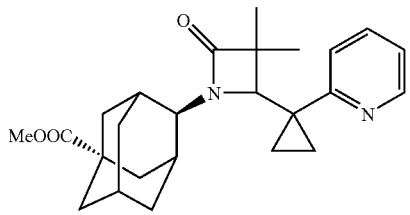

Methyl trans-4-adamantylamine-1-carboxylate was used in place of 2-adamantylamine for a similar reaction and treatment as Example 76, and the title compound was obtained as a colorless oil.

$^1$H-NMR (400 MHz, CDCl$_3$) δ; 0.92 (s, 3H), 0.94-0.99 (m, 2H), 1.24-1.29 (m, 1H), 1.36-1.43 (m, 1H), 1.47 (s, 3H), 1.62-1.66 (m, 2H), 1.85-2.05 (m, 9H), 2.25 (s, 1H), 3.07 (s, 1H), 3.36 (s, 1H), 3.66 (s, 3H), 4.32 (s, 1H), 7.01 (d, J=7.6 Hz, 1H), 7.08 (dd, J=4.8, 7.6 Hz, 1H), 7.58 (t, J=4.8 Hz, 1H), 8.49 (d, J=4.8 Hz, 1H).

IR (ATR) 2930, 1730, 1588, 1237, 1079, 777 cm$^{-1}$.

EI-MS m/z; 408 (M$^+$).

Example 81

Preparation of trans-4-{2-[1-(pyridin-2-yl)cyclopropyl]-3,3-dimethyl-4-oxoazetidin-1-yl}-1-adamantane carboxylic acid

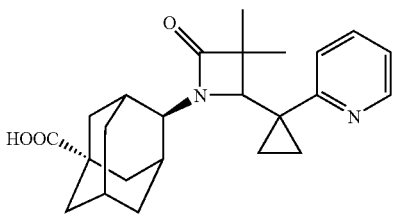

A solution of methyl trans-4-{2-[1-(pyridin-2-yl)cyclopropyl]-3,3-dimethyl-4-oxoazetidin-1-yl}-1-adamantane carboxylate (98.8 mg, 0.24 mmol) in methanol (2 mL) prepared in Example 80 was added with an aqueous solution of 4N-sodium hydroxide (1 mL, 4.00 mmol) at room temperature, and the resultant was stirred at the same temperature for 1.5 hours. The reaction solution was concentrated in vacuo, and the obtained residue was dissolved in water, and washed with diethyl ether. The aqueous layer was adjusted to a liquid of pH 6 to 7 by using 4N-hydrochloric acid, and extracted with chloroform. The organic layer was dried over anhydrous sodium sulfate, and concentrated in vacuo. The obtained residue was purified using column chromatography (chloroform:methanol=10:1), and trans-4-{2-[1-(pyridin-2-yl)cyclopropyl]-3,3-dimethyl-4-oxoazetidin-1-yl}-1-adamantane carboxylic acid (69.3 mg, 73%) was obtained as a white amorphous solid.

¹H-NMR (400 MHz, CDCl₃) δ; 0.93 (s, 3H), 0.94-0.98 (m, 2H), 1.24-1.29 (m, 1H), 1.36-1.40 (m, 1H), 1.44 (s, 3H), 1.62-1.65 (m, 2H), 1.87-2.05 (m, 9H), 2.27 (s, 1H), 3.07 (s, 1H), 3.36 (s, 1H), 4.32 (s, 1H), 7.02 (d, J=8.4 Hz, 1H), 7.09 (dd, J=3.6, 8.4 Hz, 1H), 7.59 (t, J=3.6 Hz, 1H), 8.50 (d, J=3.6 Hz, 1H).

IR (ATR) 2927, 1727, 1594, 1217, 1079, 776 cm⁻¹.

EI-MS m/z; 394 (M⁺).

Example 82

Preparation of trans-4-{2-[1-(pyridin-2-yl)cyclopropyl]-3,3-dimethyl-4-oxoazetidin-1-yl}-1-adamantane carboxyamide

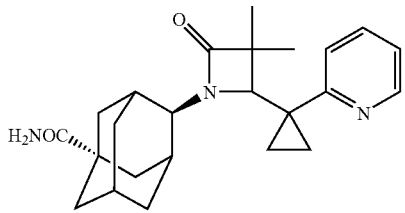

A solution of trans-4-{2-[1-(pyridin-2-yl)cyclopropyl]-3,3-dimethyl-4-oxoazetidin-1-yl}-1-adamantane carboxylic acid (61.5 mg, 0.156 mmol) in dichloromethane (3 mL) prepared in Example 81 was added with WSC.HCl (60 mg, 0.312 mmol) and HOBT.H₂O (36 mg, 0.234 mmol) at room temperature, and the resultant was stirred at the same temperature for 1.5 minutes. Then, an aqueous solution of 30% ammonia (0.200 ml) was added at room temperature, and further stirred at the same temperature for 1 hour. The reaction solution was added with water, and extracted with chloroform. The organic layer was dried over anhydrous sodium sulfate, and concentrated in vacuo. The obtained residue was purified using column chromatography (chloroform:methanol=10:1), and trans-4-{2-[1-(pyridin-2-yl)cyclopropyl]-3,3-dimethyl-4-oxoazetidin-1-yl}-1-adamantane carboxyamide (23.7 mg, 38.6%) was obtained as a white amorphous solid.

¹H-NMR (400 MHz, CDCl₃) δ; 0.92 (s, 3H), 0.93-0.98 (m, 2H), 1.24-1.27 (m, 1H), 1.32-1.39 (m, 1H), 1.46 (s, 3H), 1.61-1.65 (m, 2H), 1.84-1.96 (m, 7H), 2.05-2.08 (m, 2H), 2.28 (s, 1H), 3.10 (s, 1H), 3.38 (s, 1H), 4.31 (s, 1H), 5.65 (br, 2H), 7.00 (d, J=7.6 Hz, 1H), 7.08 (dd, J=4.8, 7.6 Hz, 1H), 7.58 (t, J=4.8 Hz, 1H), 8.48 (d, J=4.8 Hz, 1H).

IR (ATR) 2926, 1731, 1650, 1588, 1103, 1013, 749 cm⁻¹.

EI-MS m/z; 393 (M⁺).

Test Example 1

Human 11β-HSD1-, Human 11β-HSD2- and Mouse 11β-HSD1-Inhibitory Effect

1. Human 11β-HSD1-, Human 11β-HSD2- and Mouse 11β-HSD1-Gene Clonings and Establishment of Stably Expressing Cells Human 11β-HSD1-, human 11β-HSD2-, and mouse 11β-HSD1-gene clonings were conducted using as a template a reverse transcription product of human-liver RNA, human-kidney RNA (CELL APPLICATIONS), and mouse-kidney RNA respectively, by means of PCR cloning with reference to nucleotide sequences of Genbank Accession Nos. NM_005525, NM_000196, and NM_008288. The obtained PCR products of about 0.9 kbp, 1.2 kbp, and 0.9 kbp were subcloned into an expression vector pcDNA3.1+/Zeo (Invitrogen).

Human 11β-HSD1- and human 11β-HSD2-expressing vectors were transfected into human kidney-derived cell line, HEK293 cells, using a transfection reagent, jet PEI (Funakoshi). Mouse 11β-HSD1 was transfected to Chinese hamster ovary-derived cell line, CHO-K1 cells. Selection was conducted with 200-400 μg/mL of zeocine (Invitrogen) to provide stably expressing-cell clones. The stably expressing cells were suspended in buffer solution A (20 mmol/L Tris-HCl, pH 7.4, 250 mmol/L sucrose, 1 mmol/L EGTA, 1 mmol/L EDTA, 1 mmol/L MgCl₂), sonicated, and then stored at −80° C.

2. Assay of Enzyme Inhibitory Activity

An enzymatic reaction was conducted using a polystyrene 96-well plate. Each well was added with 1 μL of a test agent dissolved in DMSO and then diluted (0.003 to 3 mmol/L), and further added with 10 μL of cell lysate diluted to a concentration of 0.1 mg/mL to 0.4 mg/mL. Next, 90 μL of buffer solution A containing substrate (100 nmol/L cortisone or cortisol) and coenzyme (400 μmol/L NADPH or NAD+) was added and the mixture was incubated at 37° C. for 1 hour. The enzymatic reaction was stopped by treating at 95° C. for 3 minutes. Cortisol that was present in the reaction solution was determined by a competitive ELISA shown below.

Anti-rabbit IgG antibody (Chemi-con) diluted to 2 μg/mL with carbonate buffer solution (pH 9.6) was added in 100 μL each to a 96-well immuno plate (Nunc) and immobilized by an incubation at 4° C. overnight. 50 μL of enzymatic reaction solution was put onto the plates, and further, anti-cortisol antibody (Cosmo Bio) and HRP-labeled cortisol (Cosmo Bio), diluted with buffer solution B (25 mmol/L Tris-HCl pH 7.4, 137 mmol/L NaCl, 2.68 mmol/L KCl), were added in 50 μL respectively and incubated at 4° C. overnight. After washed three times with buffer solution B containing 0.05% Tween 20, the plates were allowed to develop color by adding 100 μL, of color reagent, TMB (Moss). The color reaction was stopped by 25 μL of 1 mol/L sulfuric acid and the absorbance was determined at 450 nm with a microplate reader (Molecular Device, VersaMax).

The values of human 11β-HSD1, human 11β-HSD2, and mouse 11β-HSD1 activities were subtracted from 100, and the resultant values were regarded as the respective 11βHSD inhibition rates of example compounds. For each example compound, the value of 50% inhibitory concentration (IC₅₀) was calculated from 11β-HSD inhibition rates at plural concentrations, for 11β-HSD1 and 11β-HSD2 activities. The comparison of human 11β-HSD1 and human 11β-HSD2 inhibiting activities is shown in Table 1, and the comparison of human 11β-HSD1 and mouse 11β-HSD1 inhibiting activities is shown in Table 2.

TABLE 1

| Enzyme inhibitory selectivity of human 11β-HSD1 and human 11β-HSD2 | | |
|---|---|---|
| | in vitro assay (IC50 uM) | |
| Example No. | h HSD1 | h HSD2 |
| 1 | 0.013 | 3-30 |
| 2 | 0.0054 | NA |
| 3 | 0.057 | NA |
| 4 | 0.046 | NA |
| 5 | 0.88 | NA |
| 6 | 0.56 | NA |

TABLE 1-continued

Enzyme inhibitory selectivity of human 11β-HSD1 and human 11β-HSD2

| Example No. | in vitro assay (IC50 uM) | |
|---|---|---|
| | h HSD1 | h HSD2 |
| 7 | 0.013 | NA |
| 8 | 0.066 | NA |
| 9 | 0.0050 | NA |
| 10 | 0.019 | NA |
| 11 | 0.26 | NA |
| 12 | 0.022 | NA |
| 13 | 0.051 | NA |
| 14 | 0.013 | NA |
| 15 | 0.031 | NA |
| 16 | 0.41 | NA |
| 18 | 0.029 | 30 |
| 20 | 0.057 | NA |
| 22 | 0.0095 | 15 |
| 23 | 0.010 | >30 |
| 24 | 0.011 | >30 |
| 25 | 0.020 | NA |
| 26 | 0.013 | >30 |
| 27 | 0.017 | 8.8 |
| 28 | 0.029 | NA |
| 29 | 0.011 | >30 |
| 30 | 0.016 | NA |
| 31 | 0.015 | NA |
| 32 | 0.024 | NA |
| 33 | 0.0067 | 6.7 |
| 34 | 0.012 | 30 |
| 35 | 0.053 | >30 |
| 36 | 0.091 | NA |
| 37 | 0.026 | 14 |
| 38 | 0.079 | 3-30 |
| 39 | 0.0034 | 3-30 |
| 40 | 0.0059 | >30 |
| 41 | 0.0087 | 3-30 |
| 42 | 0.006 | NA |
| 43 | 0.025 | NA |
| 44 | 0.0055 | 3-30 |
| 45 | 0.0081 | NA |
| 46 | 0.0081 | 30 |
| 47 | 0.0075 | NA |
| 48 | 0.0088 | NA |
| 49 | 0.10 | NA |
| 51 | 0.080 | NA |
| 52 | 0.0046 | NA |
| 53 | 0.0039 | 30 |
| 54 | 0.91 | NA |
| 55 | 0.0039 | NA |
| 56 | 0.0079 | >30 |
| 67 | 0.065 | 30 |
| 68 | 0.026 | 3-30 |
| 69 | 0.020 | 0.28 |
| 70 | 0.110 | 4.1 |
| 71 | 0.059 | 4.3 |

As it is shown in Table 1, it has been confirmed that the compound of the present invention has an activity to strongly and selectively inhibit human 11β-HSD1.

TABLE 2

Enzyme inhibitory activity of human HSD1 and mouse HSD1

| Example No. | in vitro assay (IC50 uM) | |
|---|---|---|
| | h HSD1 | m HSD1 |
| 1 | 0.013 | 0.077 |
| 2 | 0.0054 | 0.054 |
| 3 | 0.057 | 0.31 |
| 4 | 0.046 | 0.34 |
| 5 | 0.88 | 0.66 |
| 6 | 0.56 | 0.87 |
| 7 | 0.013 | 0.25 |
| 9 | 0.0050 | 0.035 |
| 10 | 0.019 | 0.034 |
| 11 | 0.26 | 0.42 |
| 12 | 0.022 | 0.023 |
| 13 | 0.051 | 0.24 |
| 14 | 0.013 | 0.0095 |
| 15 | 0.031 | 0.031 |
| 18 | 0.029 | 0.074 |
| 20 | 0.057 | 0.053 |
| 22 | 0.0095 | 0.66 |
| 24 | 0.011 | 0.10 |
| 25 | 0.020 | 0.18 |
| 26 | 0.013 | 0.46 |
| 28 | 0.029 | 0.16 |
| 29 | 0.011 | 0.59 |
| 30 | 0.016 | 0.13 |
| 31 | 0.015 | 0.076 |
| 33 | 0.0067 | 0.072 |
| 34 | 0.012 | 0.031 |
| 35 | 0.053 | 0.61 |
| 39 | 0.0034 | 0.055 |
| 40 | 0.0059 | 0.34 |
| 41 | 0.0087 | 0.079 |
| 42 | 0.0060 | 0.69 |
| 44 | 0.0055 | 0.076 |
| 45 | 0.0081 | 0.0035 |
| 46 | 0.0081 | 0.029 |
| 47 | 0.0075 | 0.0056 |
| 48 | 0.0088 | 0.33 |
| 52 | 0.0046 | 0.027 |
| 53 | 0.0039 | 0.025 |
| 55 | 0.0039 | 0.87 |
| 56 | 0.0079 | 0.46 |
| 67 | 0.065 | 0.029 |
| 68 | 0.026 | 0.020 |
| 69 | 0.020 | 0.0051 |
| 70 | 0.110 | 0.0078 |
| 71 | 0.059 | 0.0061 |

For medicine development, it is required to make a dosage selection for clinical experiments by extrapolating data which have been accumulated with animal models to human. Sometimes, the difference of enzyme species becomes an issue for evaluating an inhibitor targeting a certain enzyme, such as the compound of the present invention. Specifically, as rodents such as mouse are generally used as an animal model, a compound having an inhibitory activity to mouse type enzyme as well as human type enzyme, has an advantageous property for evaluating usefulness as medicine. As it is shown in Table 2, the compound of the present invention has been confirmed to have an inhibitory effect to mouse 11β-HSD1 as well.

The invention claimed is:

1. An 1-adamantyl azetidin-2-one derivative represented by the following general formula (1) or salt thereof:

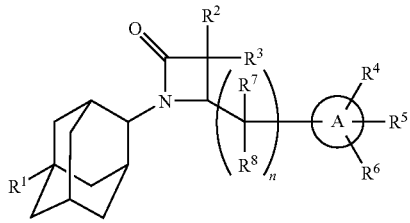

(1)

wherein ring A is a $C_{6-10}$ aryl group or a 5- to 14-membered heteroaryl group, wherein $R^1$ is a hydrogen atom, a halogen atom, a $C_{1-6}$ alkoxycarbonyl group, a mono($C_{1-8}$ alkyl)aminocarbonyl group optionally substituted with a $C_{6-10}$ aryl group, a carboxyl group or a $C_{1-6}$ alkoxycarbonyl group, a di($C_{1-8}$ alkyl)aminocarbonyl group, a $C_{3-6}$ cycloalkyl aminocarbonyl group, a $C_{2-6}$ alkanoyl group, a formyl group, a hydroxyl group, a carboxyl group or a carbamoyl group;

wherein $R^2$ and $R^3$ are the same or different and are a $C_{1-6}$ alkyl group;

wherein $R^4$, $R^5$, and $R^6$ are same or different, and are a hydrogen atom, a halogen atom, a $C_{1-6}$ alkyl group, a halo $C_{1-6}$ alkyl group, a $C_{1-6}$ alkoxy group, a halo $C_{1-6}$ alkoxy group, a $C_{1-6}$ alkylthio group, a $C_{1-6}$ alkylsulfinyl group, a $C_{1-6}$ alkylsulfonyl group, an amino group, a $C_{6-10}$ aryl group, a mono($C_{1-8}$ alkyl)amino group, a di($C_{1-8}$ alkyl)amino group, a $C_{2-6}$ alkanoylamino group or a formylamino group, or $R^4$ and $R^5$, or $R^5$ and $R^6$ together with the atom to which these are attached form a $C_{1-3}$ alkylenedioxy group, wherein $R^7$ and $R^8$ are the same or different and are a hydrogen atom or a $C_{1-6}$ alkyl group, or together with the atom to which these are attached form a $C_{3-6}$ cyclic hydrocarbon group, and wherein n represents an integer of 0 or 1.

2. The 1-adamantyl azetidin-2-one derivative according to claim 1, wherein the 1-adamantyl azetidin-2-one derivative is selected from the group consisting of:

1-(adamantan-2-yl)-3,3-dimethyl-4-phenylazetidin-2-one,
1-(adamantan-2-yl)-3,3-dimethyl-4-(2,3-dichlorophenyl)azetidin-2-one,
trans-1-(5-chloroadamantan-2-yl)-3,3-dimethyl-4-(2,3-dichlorophenyl)azetidin-2-one,
cis-1-(5-chloroadamantan-2-yl)-3,3-dimethyl-4-(2,3-dichlorophenyl)azetidin-2-one,
trans-1-(5-chloroadamantan-2-yl)-3,3-dimethyl-4-(naphthalen-1-yl)azetidin-2-one,
cis-1-(5-chloroadamantan-2-yl)-3,3-dimethyl-4-(naphthalen-1-yl)azetidin-2-one,
methyl trans-4-[2-(2,3-dichlorophenyl)-3,3-dimethyl-4-oxoazetidin-1-yl]-1-adamantane carboxylate,
trans-4-[2-(2,3-dichlorophenyl)-3,3-dimethyl-4-oxoazetidin-1-yl]-1-adamantane carboxylic acid,
trans-4-[2-(2,3-dichlorophenyl)-3,3-dimethyl-4-oxoazetidin-1-yl]-1-adamantane carboxyamide,
methyl trans-4-[2-(naphthalen-1-yl)-3,3-dimethyl-4-oxoazetidin-1-yl]-1-adamantane carboxylate,
trans-4-[2-(naphthalen-1-yl)-3,3-dimethyl-4-oxoazetidin-1-yl]-1-adamantane carboxylic acid,
trans-4-[2-(naphthalen-1-yl)-3,3-dimethyl-4-oxoazetidin-1-yl]-1-adamantane carboxyamide,
methyl trans-4-[2-(benzo[d][1,3]dioxol-4-yl)-3,3-dimethyl-4-oxoazetidin-1-yl]-1-adamantane carboxylate,
trans-4-[2-(benzo[d][1,3]dioxol-4-yl)-3,3-dimethyl-4-oxoazetidin-1-yl]-1-adamantane carboxylic acid,
trans-4-[2-(benzo[d][1,3]dioxol-4-yl)-3,3-dimethyl-4-oxoazetidin-1-yl]-1-adamantane carboxyamide,
trans-4-[2-(isoquinolin-5-yl)-3,3-dimethyl-4-oxoazetidin-1-yl]-1-adamantane carboxyamide,
trans-4-[2-(quinolin-5-yl)-3,3-dimethyl-4-oxoazetidin-1-yl]-1-adamantane carboxylic acid,
methyl trans-4-[2-(quinolin-8-yl)-3,3-dimethyl-4-oxoazetidin-1-yl]-1-adamantane carboxylate,
trans-4-[2-(quinolin-8-yl)-3,3-dimethyl-4-oxoazetidin-1-yl]-1-adamantane carboxylic acid,
trans-4-[2-(quinolin-8-yl)-3,3-dimethyl-4-oxoazetidin-1-yl]-1-adamantane carboxyamide,
1-(adamantan-2-yl)-3,3-dimethyl-4-(2,3-dimethoxyphenyl)azetidin-2-one,
1-(adamantan-2-yl)-3,3-dimethyl-4-(4-chlorophenyl)azetidin-2-one,
1-(adamantan-2-yl)-3,3-dimethyl-4-(4-methoxyphenyl)azetidin-2-one,
1-(adamantan-2-yl)-3,3-dimethyl-4-(2,3-difluorophenyl)azetidin-2-one,
1-(adamantan-2-yl)-3,3-dimethyl-4-(3-chloro-2-fluorophenyl)azetidin-2-one,
1-(adamantan-2-yl)-3,3-dimethyl-4-(3,4-dichlorophenyl)azetidin-2-one,
1-(adamantan-2-yl)-3,3-dimethyl-4-(3,4-difluorophenyl)azetidin-2-one,
1-(adamantan-2-yl)-3,3-dimethyl-4-(2-fluoro-3-trifluoromethylphenyl)azetidin-2-one,
1-(adamantan-2-yl)-3,3-dimethyl-4-(3-chloro-4-fluorophenyl)azetidin-2-one,
1-(adamantan-2-yl)-3,3-dimethyl-4-(2-chloro-3-trifluoromethylphenyl)azetidin-2-one,
1-(adamantan-2-yl)-3,3-dimethyl-4-(3,5-dichlorophenyl)azetidin-2-one,
1-(adamantan-2-yl)-3,3-dimethyl-4-(4-fluoro-3-trifluoromethylphenyl)azetidin-2-one,
1-(adamantan-2-yl)-3,3-dimethyl-4-(2-methoxyphenyl)azetidin-2-one,
1-(adamantan-2-yl)-3,3-dimethyl-4-(3-methoxyphenyl)azetidin-2-one,
1-(adamantan-2-yl)-3,3-dimethyl-4-(2,3,5-trifluorophenyl)azetidin-2-one,
1-(adamantan-2-yl)-3,3-dimethyl-4-(3,4,5-trifluorophenyl)azetidin-2-one,
1-(adamantan-2-yl)-3,3-dimethyl-4-(4-isopropylphenyl)azetidin-2-one,
1-(adamantan-2-yl)-3,3-dimethyl-4-(4-t-butylphenyl)azetidin-2-one,
1-(adamantan-2-yl)-3,3-dimethyl-4-(2-fluorophenyl)azetidin-2-one,
1-(adamantan-2-yl)-3,3-dimethyl-4-(2-fluoro-4-methoxyphenyl)azetidin-2-one,
1-(adamantan-2-yl)-3,3-dimethyl-4-(2-trifluoromethylphenyl)azetidin-2-one,
1-(adamantan-2-yl)-3,3-dimethyl-4-(4-trifluoromethoxyphenyl)azetidin-2-one,
1-(adamantan-2-yl)-3,3-dimethyl-4-(4-bromophenyl)azetidin-2-one, 1-(adamantan-2-yl)-3,3-dimethyl-4-(2-chlorophenyl)azetidin-2-one,
1-(adamantan-2-yl)-3,3-dimethyl-4-(naphthalen-1-yl)azetidin-2-one,
trans-1-(5-hydroxyadamantan-2-yl)-3,3-dimethyl-4-(2,3-dichlorophenyl)azetidin-2-one,
trans-1-(5-hydroxyadamantan-2-yl)-3,3-dimethyl-4-(naphthalen-1-yl)azetidin-2-one,
trans-1-(5-hydroxyadamantan-2-yl)-3,3-dimethyl-4-(4-methoxynaphthalen-1-yl)azetidin-2-one,
methyl trans-4-[2-(quinolin-4-yl)-3,3-dimethyl-4-oxoazetidin-1-yl]-1-adamantane carboxylate,
trans-4-[2-(quinolin-4-yl)-3,3-dimethyl-4-oxoazetidin-1-yl]-1-adamantane carboxylic acid,
trans-4-[2-(quinolin-4-yl)-3,3-dimethyl-4-oxoazetidin-1-yl]-1-adamantane carboxyamide,
trans-1-(5-fluoroadamantan-2-yl)-3,3-dimethyl-4-(2,3-dichlorophenyl)azetidin-2-one,
1-(adamantan-2-yl)-3,3-dimethyl-4-(3-chlorophenyl)azetidin-2-one,
1-(adamantan-2-yl)-3,3-dimethyl-4-[3,5-bis(trifluoromethyl)phenyl]azetidin-2-one,
1-(adamantan-2-yl)-3,3-dimethyl-4-[4-(methylthio)phenyl]azetidin-2-one,
1-(adamantan-2-yl)-3,3-dimethyl-4-(4-methoxy-2-methylphenyl)azetidin-2-one,
trans-4-[2-(benzo[d][1,3]dioxol-4-yl)-3,3-dimethyl-4-oxoazetidin-1-yl]-N-methyl-1-adamantane carboxyamide,
trans-4-[2-(benzo[d][1,3]dioxol-4-yl)-3,3-dimethyl-4-oxoazetidin-1-yl]-N-ethyl-1-adamantane carboxyamide,
trans-4-[2-(benzo[d][1,3]dioxol-4-yl)-3,3-dimethyl-4-oxoazetidin-1-yl]-N-propyl-1-adamantane carboxyamide,
trans-4-[2-(benzo[d][1,3]dioxol-4-yl)-3,3-dimethyl-4-oxoazetidin-1-yl]-N-hexyl-1-adamantane carboxyamide,
trans-4-[2-(benzo[d][1,3]dioxol-4-yl)-3,3-dimethyl-4-oxoazetidin-1-yl]-N-octyl-1-adamantane carboxyamide,
trans-4-[2-(benzo[d][1,3]dioxol-4-yl)-3,3-dimethyl-4-oxoazetidin-1-yl]-N-cyclopropyl-1-adamantane carboxyamide,
trans-4-[2-(benzo[d][1,3]dioxol-4-yl)-3,3-dimethyl-4-oxoazetidin-1-yl]-N-cyclohexyl-1-adamantane carboxyamide,
trans-4-[2-(benzo[d][1,3]dioxol-4-yl)-3,3-dimethyl-4-oxoazetidin-1-yl]-N-benzyl-1-adamantane carboxyamide,
methyl trans-2-[4-(2-(benzo[d][1,3]dioxol-4-yl)-3,3-dimethyl-4-oxoazetidin-1-yl)-1-adamantane carboxyamide]acetate,
trans-2-[4-(2-(benzo[d][1,3]dioxol-4-yl)-3,3-dimethyl-4-oxoazetidin-1-yl)-1-adamantane carboxyamide]acetic acid,
1-(adamantan-2-yl)-4-(2,5-dihydrobenzo[b]oxepin-9-yl)-3,3-dimethylazetidin-2-one,
1-(adamantan-2-yl)-3,3-dimethyl-4-(benzo[b]oxepan-9-yl)azetidin-2-one,
4-benzyl-1-(adamantan-2-yl)-3,3-dimethylazetidin-2-one,
4-[1-(4-chlorophenyl)cyclopropyl]-1-(adamantan-2-yl)-3,3-dimethylazetidin-2-one,
1-(adamantan-2-yl)-3,3-dimethyl-4-(1-phenylcyclopropyl)azetidin-2-one,
1-(adamantan-2-yl)-4-[1-(4-methoxyphenyl)cyclopropyl]-3,3-dimethylazetidin-2-one,
1-(adamantan-2-yl)-3,3-dimethyl-4-(1-p-tolylcyclopropyl)azetidin-2-one,
4-[1-(benzo[d][1,3]dioxol-5-yl)cyclopropyl]-1-(adamantan-2-yl)-3,3-dimethylazetidin-2-one,
4-[1-(4-bromophenyl)cyclopropyl]-1-(adamantan-2-yl)-3,3-dimethylazetidin-2-one,
1-(adamantan-2-yl)-3,3-dimethyl-4-[1-(pyridin-2-yl)cyclopropyl]azetidin-2-one,
4-[1-(2-chlorophenyl)cyclopropyl]-1-(adamantan-2-yl)-3,3-dimethylazetidin-2-one,
4-[1-(3-chlorophenyl)cyclopropyl]-1-(adamantan-2-yl)-3,3-dimethylazetidin-2-one,
4-[1-(biphenyl-4-yl)cyclopropyl]-1-(adamantan-2-yl)-3,3-dimethylazetidin-2-one,
methyl trans-4-{2-[1-(pyridin-2-yl)cyclopropyl]-3,3-dimethyl-4-oxoazetidin-1-yl}-1-adamantane carboxylate,
trans-4-{2-[1-(pyridin-2-yl)cyclopropyl]-3,3-dimethyl-4-oxoazetidin-1-yl}-1-adamantane carboxylic acid, and
trans-4-{2-[1-(pyridin-2-yl)cyclopropyl]-3,3-dimethyl-4-oxoazetidin-1-yl}-1-adamantane carboxyamide.

3. A pharmaceutical composition, comprising:
the 1-adamantyl azetidin-2-one derivative or salt thereof according to claim 1, and
a pharmaceutically acceptable carrier.

\* \* \* \* \*